(12) United States Patent
Childers et al.

(10) Patent No.: US 8,142,649 B2
(45) Date of Patent: *Mar. 27, 2012

(54) METHOD FOR OPTIMIZING TIDAL THERAPIES EMPLOYING ULTRAFILTRATE TRENDING

(75) Inventors: Robert W. Childers, Trinity, FL (US); Peter A. Hopping, Lutz, FL (US)

(73) Assignees: Baxter International Inc., Deerfield, IL (US); Baxter Healthcare S.A., Glattpark (Opfikon)

( * ) Notice: Subject to any disclaimer, the term of this patent is extended or adjusted under 35 U.S.C. 154(b) by 501 days.

This patent is subject to a terminal disclaimer.

(21) Appl. No.: 12/362,240

(22) Filed: Jan. 29, 2009

(65) Prior Publication Data

US 2010/0191180 A1 Jul. 29, 2010

(51) Int. Cl.
*B01D 61/32* (2006.01)
(52) U.S. Cl. ..... 210/87; 210/141; 210/143; 210/321.65; 210/645; 604/6.01; 604/6.09; 604/29; 604/67
(58) Field of Classification Search ............... 210/96.1, 210/96.2, 141, 143, 321.65, 637, 645–647, 210/739, 929, 85, 87, 482; 604/5.01, 6.01, 604/6.05, 6.09, 29, 65–67; 600/300; 702/19; 700/273; 705/2, 3; 706/45–48, 61, 924
See application file for complete search history.

(56) References Cited

U.S. PATENT DOCUMENTS

| | | | |
|---|---|---|---|
| 4,190,047 A * | 2/1980 | Jacobsen et al. ............. | 604/28 |
| 5,324,422 A * | 6/1994 | Colleran et al. ............. | 210/85 |
| 5,334,139 A | 8/1994 | Jeppsson et al. | |
| 5,421,823 A | 6/1995 | Kamen et al. | |
| 5,643,201 A | 7/1997 | Peabody et al. | |
| 6,074,359 A | 6/2000 | Keshaviah et al. | |
| 6,558,343 B1 * | 5/2003 | Neftel ............. | 604/28 |
| 6,592,542 B2 | 7/2003 | Childers et al. | |
| 6,691,047 B1 * | 2/2004 | Fredericks ............. | 702/47 |
| 6,976,973 B1 | 12/2005 | Ruddell et al. | |
| 7,029,456 B2 * | 4/2006 | Ware et al. ............. | 604/131 |
| 7,238,164 B2 | 7/2007 | Childers et al. | |
| 7,351,340 B2 * | 4/2008 | Connell et al. ............. | 210/645 |
| 2007/0215545 A1 * | 9/2007 | Bissler et al. ............. | 210/646 |

(Continued)

FOREIGN PATENT DOCUMENTS

JP 2003-047657 2/2003

(Continued)

OTHER PUBLICATIONS

James C. Brandes, et al., "Optimization of Dialysate Flow and Mass Transfer During Automated Peritoneal Dialysis," American Journal of Kidney Diseases, vol. 25, No. 4, Apr. 1995, 9 pages.

(Continued)

*Primary Examiner* — Joseph Drodge
(74) *Attorney, Agent, or Firm* — K&L Gates LLP

(57) ABSTRACT

A system and method for automatically adjusting a Continuous Cycling Peritoneal Dialysis ("CCPD") therapy to minimize the potential for excess intra-peritoneal volume. The adjustments are made at the end of the drain, just prior to the next fill. The adjustments short the next fill, if necessary, to limit the intra-peritoneal volume, add a cycle, if necessary, to use all of the available dialysis solution and will average the remaining dwell time to maximize the therapeutic benefit of the therapy in the allotted time. In another embodiment, a tidal therapy using trended patient UF data is provided.

18 Claims, 26 Drawing Sheets

U.S. PATENT DOCUMENTS

| | | | |
|---|---|---|---|
| 2008/0015493 A1* | 1/2008 | Childers et al. | 604/29 |
| 2008/0161751 A1* | 7/2008 | Plahey et al. | 604/29 |
| 2010/0010427 A1 | 1/2010 | Yu et al. | |

FOREIGN PATENT DOCUMENTS

| | | |
|---|---|---|
| WO | 99/06082 | 2/1999 |
| WO | 01/64236 | 9/2001 |
| WO | 2005/035023 | 4/2005 |

OTHER PUBLICATIONS

Bengt Rippe, et al., "Computer simulations of peritoneal fluid transport in CAPD," Kidney International, vol. 40, (1991), pp. 315-325.

Edward Vonesh, et al., "Net Fluid Absorption Membrane Transport Models of Peritoneal Dialysis," Blood Purif., 1992, vol. 10, pp. 209-226.

Serena brochure visualizing prescription software, 2 pages, author unknown.

International Preliminary Report on Patentability for International Application No. PCT/US2010/022370 mailed on Apr. 26, 2011.

International Search Report and Written Opinion for International Application No. PCT/US2010/022367 mailed on Jul. 20, 2010.

* cited by examiner

METHOD FOR OPTIMIZING TIDAL THERAPIES EMPLOYING ULTRAFILTRATE TRENDING

BACKGROUND

The present disclosure relates generally to peritoneal dialysis, and in particular to peritoneal dialysis systems useful in manipulating the number of cycles, drain volumes and fill volumes in a multi-cycle dialysis therapy. The calculations and manipulations are useful in assuring the use of all or nearly all a prescribed dialysis solution volume in treating a particular patient during a particular therapy.

Automated Peritoneal Dialysis ("APD") is a natural evolution of Continuous Ambulatory Peritoneal Dialysis ("CAPD"), in which the patient introduces the entire contents of a dialysate solution bag into his/her peritoneum and allows the volume to dwell for three to six hours. After the dwell period, the fluid is drained using gravity. The above process is typically repeated three or four times each day as necessary. Working adults may perform an exchange at home before leaving for work, one at work during their lunch hour, one when the patient arrives home from work and one just before the patient goes to bed. Some school-aged patients follow a similar routine except they perform their mid-day exchange at school.

APD machines (sometimes called "cyclers") perform sequential exchanges during the night when the patient is sleeping, making APD a more convenient therapy. Also, the treatment is carried out in the privacy of the patient's home, so that others do not have to know that the patient is on dialysis. It is no surprise that most patients would prefer APD over CAPD.

However, there are some important differences between CAPD and APD. CAPD is typically performed with the patient sitting upright in a chair, whereas APD is performed with the patient lying down. The patient's internal catheter may work its way down into the bottom of the patient's peritoneal cavity (pelvic area) during the day when the patient is up and about so that it is not in an optimum position for draining when the patient is in a prone or sleeping position. Even with the catheter in the correct position, a supine or sitting position is generally better for draining than is the prone or sleeping position. Thus APD treatments can experience incomplete drains.

Continuous Cycling Peritoneal Dialysis ("CCPD") is one popular APD therapy because it performs a full drain after every dwell, minimizing the potential for overfill due to the fluid that is ultrafiltered from the patient's body. CCPD can however present a challenge when a patient does not drain well. In a night therapy, the patient cannot be awakened every 1.5 hours, so that the patient can sit up and ensure a complete drain.

Accordingly, APD cyclers in some instances advance from drain to fill after a minimum percentage of the patient's previous fill volume has been drained, for example, when the drain flow rate has slowed down to a point that time is being wasted that could be used for therapeutic benefit. Alarms will typically be posted if the drain flow rate slows to a certain rate before the minimum drain percentage has been exceeded. The HomeChoice/Pro® APD cycler, provided by the assignee of the present disclosure, is considered one of the best draining cyclers on the market, producing fewer alarms when compared to its competitors. Even still, low drain volume alarms occur relatively frequently.

An APD cycler with improved drain control is needed accordingly.

SUMMARY

As discussed above, automated Peritoneal Dialysis ("APD") cyclers perform sequential exchanges during the night making APD a convenient dialysis therapy. An alternative PD therapy, continuous ambulatory peritoneal dialysis ("CAPD") is performed during the day, making CAPD more life intrusive. During CAPD, however, the patient is awake and can move around and sit up during drains, allowing drains to be performed completely.

At night, when the patient is performing APD, the patient is lying down. The patient's internal catheter may have shifted during the day, making the patient susceptible to an incomplete drain. The APD system of the present disclosure is programmed to advance to a fill if a drain flow rate slows to a certain point and a minimum drain volume has been achieved. If the drain has not reached this minimum volume, which is often based upon a certain percentage of the programmed fill, the system will alarm. When an alarm occurs, the patient is awakened, which is not desirable. The system of the present disclosure greatly reduces the number of low drain alarms.

Another therapy concern enhancing the low drain problem is a limit placed on how full the patient can be filled. Multiple incomplete drains leave an ever increasing residual volume of fluid in the patient. If the residual volume increases to a certain point, the next fill may push the patient's intra-peritoneal volume ("IPV") past an allowable limit. The subsequent fill may therefore be shorted to prevent overfilling, but this may cause the treatment not to use all of the fluid for treatment.

To remedy the above, in one embodiment, the system begins a CCPD treatment that attempts to drain the patient completely after each drain. When performed properly, the CCPD therapy is quite effective. The patient's initial drain (at night, just before bed) and final drain (in the morning, after waking) should be relatively if not totally complete because the patient can sit-up and move around to help move the patient's catheter into areas of his/her peritoneum that are pocketing fluid.

It is the intermediate drains that may be difficult to complete especially considering that the therapy needs to move along and cannot wait while a low drain flow rate occurs while attempting to drain the patient completely. When the low flow rate is sensed, the system determines that it is time to move to the next fill. If the previous drain was almost complete, e.g., 85% of prescribed, the system in one embodiment continues to provide the prescribed CCPD therapy. If all subsequent drains are complete, the final drain can remove the additional, e.g., 15%, fluid from the delinquent drain.

If multiple "almost complete" drains occur, the patient can begin to build a substantial residual volume due to the cumulative effects of the incomplete drains. If the system determines that a next fill will increase the patient's intra-peritoneal volume ("IPV") past an allowable volume, e.g., 1.9 times the prescribed fill volume, the system switches to a tidal therapy that reduces the prescribed drain to a tidal volume, increasing the likelihood of the system having a subsequent successful drain. The tidal therapy also reduces succeeding fills, such that the patient's IPV does not exceed the allowable limit.

The now tidal therapy may add one or more cycle if needed to use all of the prescribed fresh solution. A logic flow diagram is shown below with various equations for determining when the one or more additional cycle is needed. Whether or not a cycle is added, the system divides the remaining unused therapy fluid and the remaining therapy time evenly over the number of remaining cycles.

The switch to tidal therapy attempts to reduce low drain alarms that occur if the actual drain does not meet a threshold percentage, e.g., 85%, of the prescribed drain. The tidal therapy allows for a larger residual volume to reside within the patient at the end of a drain, increasing the likelihood that a flow rate at the end of the drain will be high and that the drain will not be ended early due to a low drain flow rate. The tidal therapy uses all of the remaining fresh dialysate, so that the patient is not deprived of any therapeutic benefit. The tidal therapy is also completed on time and ensures that the patient is not overfilled with dialysis fluid at any time.

In one embodiment, a dialysis system is provided, the dialysis system including at least one dialysis fluid pump configured to pump a dialysis fluid to and from a patient over a treatment, the dialysis system also including a logic implementer configured to control the dialysis fluid pumped by the at least one dialysis fluid pump to and from a patient over the treatment, the logic implementer configured to use at least one trended ultrafiltration ("UF") data point for the patient to determine an amount of effluent dialysis fluid to remove from the patient during at least one patient drain.

In another embodiment, the dialysis system includes at least one dialysis fluid pump to pump a dialysis fluid to and from a patient over a treatment, the dialysis system also including a logic implementer configured to control the dialysis fluid pumped by the at least one dialysis fluid pump to and from a patient over the treatment, the logic implementer configured to (i) store a trend of ultrafiltration data points for the patient, and (ii) use at least one of the UF data points to predict the patient's intra-peritoneal volume ("IPV") at an end of at least one dwell.

In yet another embodiment, a dialysis system includes at least one dialysis fluid pump configured to pump a dialysis fluid to and from a patient over a treatment, the system also including a logic implementer configured to control the dialysis fluid pumped by the at least one dialysis fluid pump to and from a patient over the treatment, the logic implementer configured to (i) store a trend of ultrafiltration data points for the patient, and (ii) use one of the UF data points in a tidal treatment to predict a residual volume of effluent fluid left in the patient's peritoneum after at least one drain.

In one embodiment, a tidal therapy is provided in which a predicted amount of patient UF for each cycle is obtained from a trend of a UF values for the patient, for the tidal therapy, and for a particular dialysate, having a particular osmotic agent or dextrose level. In this manner, UF can be predicted very accurately.

Knowing predicted UF accurately allows the system to predict the patient's intraperitoneal volume or IPV very accurately. For example, assuming that the patient's initial drain is a successful complete drain (patient awake), the patient is then filled to a known level. The subsequent dwell will remove an amount of UF from the patient that should closely approximate the predicted removal of UF. Thus the actual IPV at the end of the dwell should closely approach the actual fill amount (which is known) plus a predicted UF removed (which is based on trended UF).

The UF trend is stored and updated in one embodiment at the cycler or automated peritoneal dialysis ("APD") machine. The patient can recall the trend at any time to view same including historical trending data. The APD machine can be linked via a data network, such as an internet, so that a dialysis clinician or doctor can also view the patient's UF trend remotely. In an alternative embodiment, the UF trend is stored and updated on a remote server, which the patient can access via the data network.

The UF trend in one embodiment plots patient single day UF data. If the patient removes 2000 ml of UF on day X, 2000 ml is recorded for day X. And the daily UF in one embodiment is the UF removed over the nightly treatment, that is, the UF removed after the initial drain (from previous days last fill or from day exchange) and prior to the last fill, if provided. Here, the daily UF is that removed over the course of multiple tidal dwells. This total UF can be measured accurately because the patient is drained completely on the initial drain. The measured UF, which is entered into the trend is then the total amount of drained fluid, not including the initial drain, but including the last drain, which is typically a complete drain with the patient awake, less the total amount of fresh dialysis fluid pumped to the patient, but not including the final fill. The APD machine can measure each of these values accurately to provide a true UF data point.

In an alternative embodiment, the trended UF data is averaged UF data for a particular therapy using a particular dialysate glucose level. The average can for example be a rolling seven or thirty day average that averages the last seven or thirty day's UF entries, respectively, for each dialysate glucose solution used by the patient, to form a rolling average UF volume for such glucose level solution. Such averaging tends to smooth UF anomalies for treatments that may have undergone unusual events, such as alarms or other stoppage.

In view of the above embodiments, it is accordingly an advantage of the present disclosure to provide improved Continuous Cycling Peritoneal Dialysis ("CCPD") and tidal automated peritoneal dialysis ("APD") therapies.

Another advantage of the system of the present disclosure is to provide an APD therapy that tends to limit low drain alarms.

A further advantage of the system of the present disclosure is to provide an APD therapy that tends to limit patient overfilling.

Yet another advantage of the system of the present disclosure is to provide an APD therapy that tends use all available fresh dialysis fluid over the course of treatment.

A further advantage of the system of the present disclosure is to provide an APD therapy that adjusts to an incomplete drain to prevent a patient overfill.

Still another advantage of the system of the present disclosure is to provide an APD therapy that reacts to an incomplete drain to ensure that all available treatment fluid is used over the course of treatment.

Still a further advantage of the system of the present disclosure is to provide an APD therapy that employs ultrafiltration ("UF") trending to provide trending data that allows for accurate prediction of UF and overall intra-peritoneal volume ("IPV").

Additional features and advantages are described herein, and will be apparent from the following Detailed Description and the figures.

DETAILED DESCRIPTION

Dialysis System Generally

Figure 1:
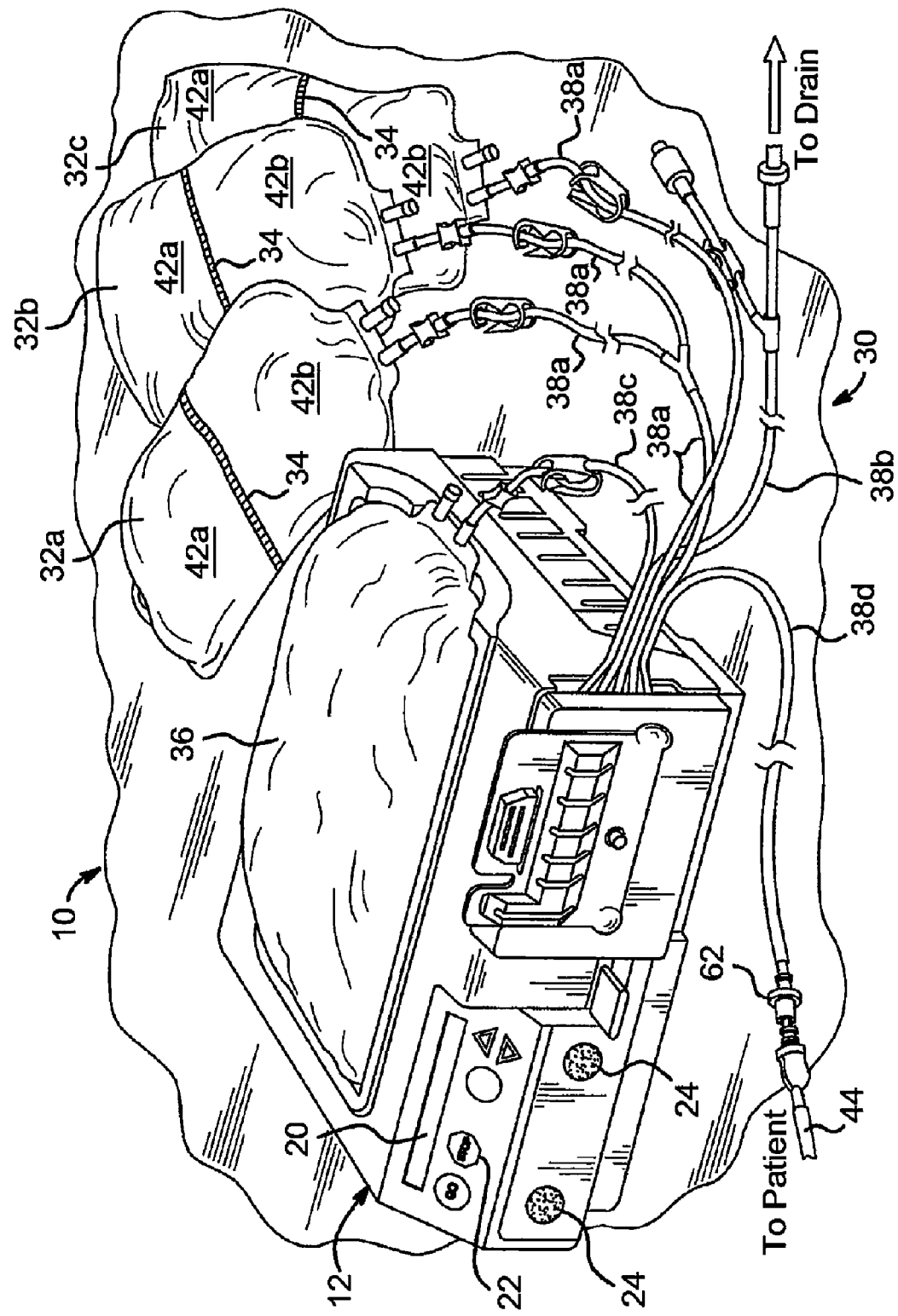
FIG. 1 is a perspective view of one embodiment of a dialysis system having a drain and fill sequence according to the present disclosure.
Figure 2:
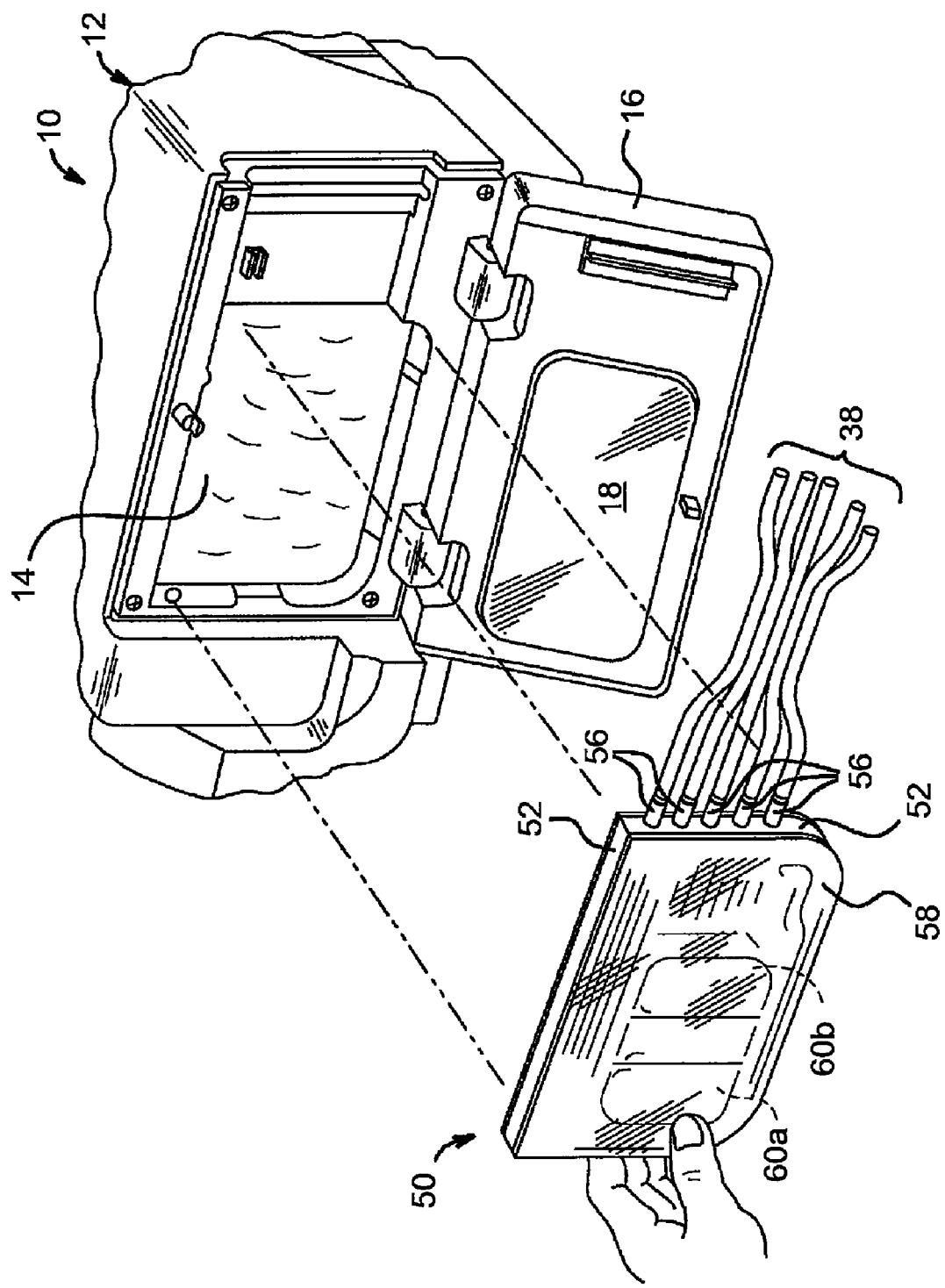
FIG. 2 is a perspective view of one embodiment of a disposable cassette operable with the dialysis system having a drain and fill sequence according to the present disclosure.

Referring now to the drawings and in particular to FIGS. 1 to 2, a renal failure therapy system 10 is provided. System 10 is applicable generally to any type of automated peritoneal dialysis ("APD") system. System 10 in the illustrated embodiment includes a dialysis instrument 12. Dialysis instrument 12 is configured for the type of APD therapy system provided. Dialysis instrument 12 includes a central processing unit ("CPU") and memory, and may include one or more additional processor and memory (e.g., safety, valve, heater, pump, video and audio (e.g., voice guidance) controllers) operable with the CPU, the totality of which may be called a logic implementer. The logic implementer operates with a user interface ("UI") such as a graphical user-machine interface ("GUI"), e.g., via a video controller component of the logic implementer. The GUI includes a video monitor 20 and one or more types of input devices 22, such as a touch screen or electromechanical input device (e.g., a membrane switch).

The logic implementer in cooperation with video monitor 20 provides therapy instructions and setup confirmation to the patient or caregiver visually via characters/graphics. For example, characters/graphics can be displayed to (i) provide instructions regarding placement of a distal end of the patient line onto instrument 12 (discussed below) for priming and/or (ii) inform the patient when the patient line has been primed fully. Additionally or alternatively, a voice guidance controller of the logic implementer in cooperation with speakers 24 provides (i) and/or (ii) listed above.

As seen in FIG. 1, dialysis instrument 12 accepts and operates with a disposable set 30. Disposable set 30 includes one or more supply bag 32a to 32c (referred to herein collectively as supply bags 32 or individually, generally as supply bag 32), shown here as dual-chamber supply bags separating two fluids via a peel or frangible seal 34. Disposable set 30 also includes a drain bag (not illustrated), a warmer bag 36, and patient tubes 38a to 38d, respectively (referred to herein collectively as tubing or tubes 38 or individually, generally as tube 38) and a disposable pumping/valve cassette 50 (FIG. 2).

Warmer bag 36 is used in a batch heating operation in which the top of instrument 12 batch heats fluid within bag 36. System 10 can also pump spent fluid to a house drain, such as a bathtub, a toilet or sink, instead of to a drain bag, in which case the drain bag is not needed.

While three supply bags 32 are shown, system 10 can employ any suitable number of supply bags. Supply bags 32 are shown having multiple chambers 42a and 42b, separated by frangible seal 34, which hold different solutions depending on the type of therapy employed. For example, chambers 42a and 42b can hold buffer and glucose for an overall PD dialysate having a desired glucose level. Supply bags 32 are alternatively single chamber bags, which hold a single premixed solution, such as premixed PD dialysate having a desired glucose level.

As seen in FIGS. 1 and 2, a disposable cassette 50 connects to supply bags 32, drain bag and warmer bag 36 via tubes 38a, 38b and 38c, respectively. Tube 38d runs from cassette 50 to a patient connection 44. Cassette 50 in one embodiment includes a rigid structure having rigid outer walls 52 and a middle, base wall (not shown) from which pump chambers (60a and 60b as shown in FIG. 2), valve chambers (e.g., volcano valve chambers) and rigid fluid pathways extend. Rigid fluid ports 56 extend from a side wall 52 and communicate fluidly with the rigid cassette pathways and connect sealingly to tubing 38. Tubing 38 can be fixed to ports 56, in which case the bags 32 are spiked to allow fluid from the bags to flow through tubing 38 into cassette 50. Alternatively, tubing 38 is fixed to bags 32, in which case ports 56 are spiked to allow fluid from the bags 32 and tubing 38 into cassette 50.

A pair of flexible membranes or sheets 58 (only one shown) is sealed to outer rigid walls 52 of the cassette. Cassette 50 is sealed within instrument 12 such that sheeting 58 forms the outer surfaces of the rigid fluid pathways of the cassette. One of the sheets is moved to pump fluid through pump chambers (60a and 60b) and to open and close the cassette valves.

Instrument 12 can actuate the pump and valve chambers of cassette 50 pneumatically, mechanically or both. The illustrated embodiment uses pneumatic actuation. The HomeChoice® APD system uses a pneumatic system described in U.S. Pat. No. 5,350,357 ("the '357 patent"), the entire contents of which are incorporated herein by reference. As seen in FIG. 2, instrument 12 includes a flexible membrane 14, which creates different sealed areas with cassette sheeting 58 at each of the pump and valve chambers of cassette 50. Membrane 14 moves with the sheeting 58 in those areas to either open/close a valve chamber or pump fluid through (into and out of) a pump chamber. An interface plate (not shown) is located behind membrane 14 and includes first and second chamber halves (not shown) that mate with chamber halves 60a and 60b of cassette 50 to form a pair of fixed volume pump chambers.

Instrument 12 in the illustrated embodiment includes a door 16, which closes against cassette 50. Door 16 includes a press plate 18, which can be operated mechanically (e.g., via the closing of the door) and/or pneumatically (e.g., via an inflatable bladder located in the door behind the press plate). Pressing plate 18 against cassette 50 in turn presses cassette 50 against pumping membrane 14, which cooperates with sheeting 58 of cassette 50 to pump fluid through chambers 60a and 60b and to open and close the cassette valve chambers.

The cassette interface plate is located behind membrane 14. Cassette interface plate is configured to apply positive or negative pressure to the cooperating membrane 14 and cassette sheeting 58 at the different valve and pump areas. For example, positive pressure is applied to membrane 14/sheeting 58 at areas of the membrane/sheeting located within the internal walls of cassette 50 that define pump chambers 60a and 60b to push fluid out of the pump chambers and within the chamber halves of the interface plate (not shown). Negative pressure is applied to membrane 14/sheeting 58 at those same areas to pull fluid into the pump chambers. Likewise, positive pressure is applied to membrane 14/sheeting 58 at areas of the sheeting within the internal walls of cassette 50 and the interface plate defining the valve chambers to close outlet ports of the valve chambers. Negative pressure is applied to membrane 14/sheeting 58 at those same areas to open the outlets of the valve chambers.

Figure 15:
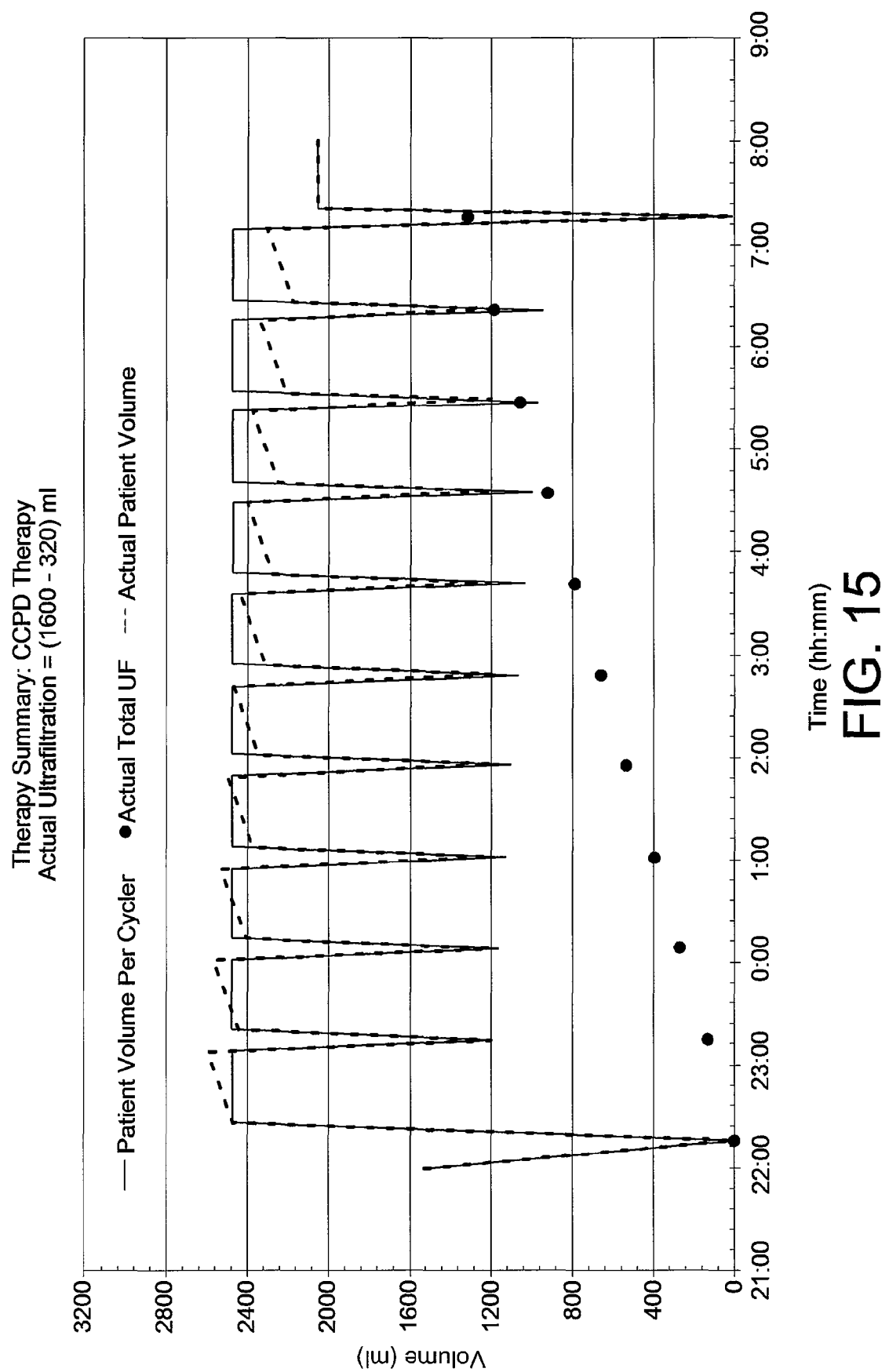

U.S. Pat. No. 6,814,547 ("the '547 patent") assigned to the assignee of the present disclosure, discloses a pumping mechanism in connection with FIGS. 17A and 17B and associated written description, incorporated herein by reference, which uses a combination of pneumatic and mechanical actuation. FIGS. 15, 16A and 16B of the '547 patent and associated written description, incorporated herein by reference, teach the use of mechanically actuated valves. One or both of these mechanisms can be used instead of the purely pneumatic system of the HomeChoice® machine.

The '357 patent and the '547 patent also teach different systems and methods, incorporated herein expressly by reference, of knowing and controlling the amount of fresh dialysate delivered to the patient, the amount of effluent dialysate removed from the patient, and thus the amount of additional fluid or ultrafiltrate ("UF") removed from the patient. UF is the blood water that the patient accumulates between treatments due to the patient's failed kidneys. The dialysis treatment removes this blood water as UF in an attempt to bring the patient back to his or her dry weight. Either of the systems and method of the '357 patent and the '547 patent can be used as described below for controlling the fill and drain volumes according to the methods of system 10.

Drain and Fill Logic for Automated Peritoneal Dialysis

Figure 3:
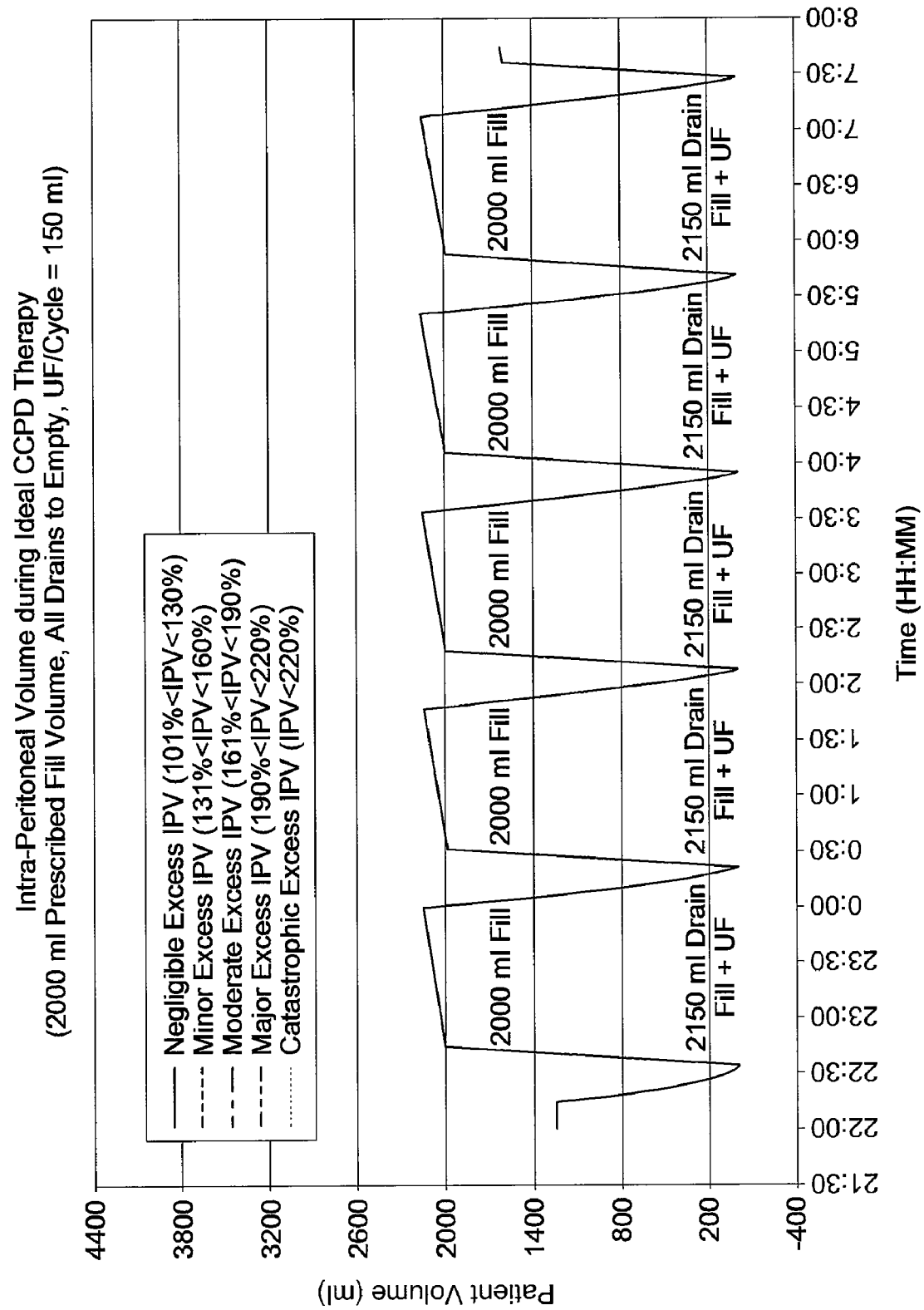
FIG. 3 is an intra-peritoneal volume ("IPV") versus time graph showing an example therapy in which a continuous cycling peritoneal dialysis ("CCPD") treatment is performed according to a prescribed therapy.

Referring now to FIG. 3, one example plot of the intra-peritoneal patient volume ("IPV") versus time over an ideal CCPD for system 10 is illustrated. Here, each drain empties completely the fluid from the patient's peritoneum, including the previous fill volume plus any UF that has occurred during the previous dwell period. As seen in FIG. 3, therapy starts with an initial drain to empty, followed by a number of identical cycles consisting of a fill to a prescribed volume, a dwell of a prescribed duration, and a drain that removes the original fill volume plus all of the UF that has been absorbed from the patient. FIG. 3 illustrates a five cycle therapy having a 2000 ml fill volume and 150 ml/cycle UF volume. The initial drain recovers all of the fluid from the previous day's last fill that has remained in the patient's peritoneal cavity throughout the day.

Patients sometimes pocket fluid so that a drain that is supposed to be to empty does not remove all of the previous fill volume. System 10 in one embodiment sets a minimum drain percentage that must be obtained when the fluid flow slows or stops. If the minimum drain volume is not met, system 10 posts a low drain volume alarm. In such a case, the therapy does not advance to fill, that is, if the drain volume is not equal to or greater than the minimum drain percentage. In FIG. 3, system 10 fills the patient to the prescribed fill volume in each fill because the minimum drain percentage for each drain has been met. One example minimum drain percentage for system 10 is about 85% of the fill volume.

System 10 in one embodiment calculates the amount of UF obtained at the end of the drain phase of each cycle as follows:

UF=sum of the volumes drained−sum of the volumes filled

The initial drain and last fills are not included in the UF calculation. Calculated UF will be positive as long as more spent fluid drained than fresh dialysis fluid filled. A zero UF value means that the volume drained after any number of cycles is equal to the volume filled during those cycles. A drain that does not recover all of the fluid that was delivered to the patient during the previous fill results in a negative UF determination. Unless the patient is absorbing fluid, a negative UF implies that the patient's intra-peritoneal volume is in excess of a prescribed fill volume.

It is normal for the intra-peritoneal volume to exceed the prescribed fill volume. The intra-peritoneal volume during a CCPD dwell phase consists of the following volumes: intra-peritoneal volume ("IPV")=prescribed fill volume+residual volume at end of a previous drain+UF from dwell. It is also not unusual for the residual volume in the patient's peritoneum to equal 5 to 10% of the prescribed fill volume at the end of a drain cycle.

The UF that has accumulated during a dwell will depend upon the osmotic gradient (a function of the dextrose level of the dialysate), the time in dwell and the transport characteristics of the patient's peritoneum. UF can range from zero to 25% of the prescribed fill volume. Thus, it is not unusual for the intra-peritoneal volume reach about 130% of the prescribed fill volume. In practice, it is expected that the IPV will vary between 100 and 130% of the prescribed fill volume.

When the residual volume at the end of drain increases, e.g., to more than five or ten percent of the prescribed fill volume, the patient's intra-peritoneal volume increases accordingly during the next fill and dwell. If system 10 sets an 85% minimum drain percentage limit, the increase in residual volume is limited to 15% per cycle plus the actual UF obtained during the cycle. Successive fill cycles after successive drains just meeting the 85% minimum drain percentage requirement will cause the patient's intra-peritoneal volume to increase at each successive cycle. System 10 also tracks cumulative UF and places a limit on the maximum negative UF value allowed. If this value is exceeded at any time during a therapy, system 10 will not advance from drain phase to the next fill phase even if the minimum drain percentage has been met when the drain ends. System 10 in one embodiment allows the patient or caregiver, in certain instances, to override the negative UF alarm and allow the therapy to advance to the next fill.

Figure 4:
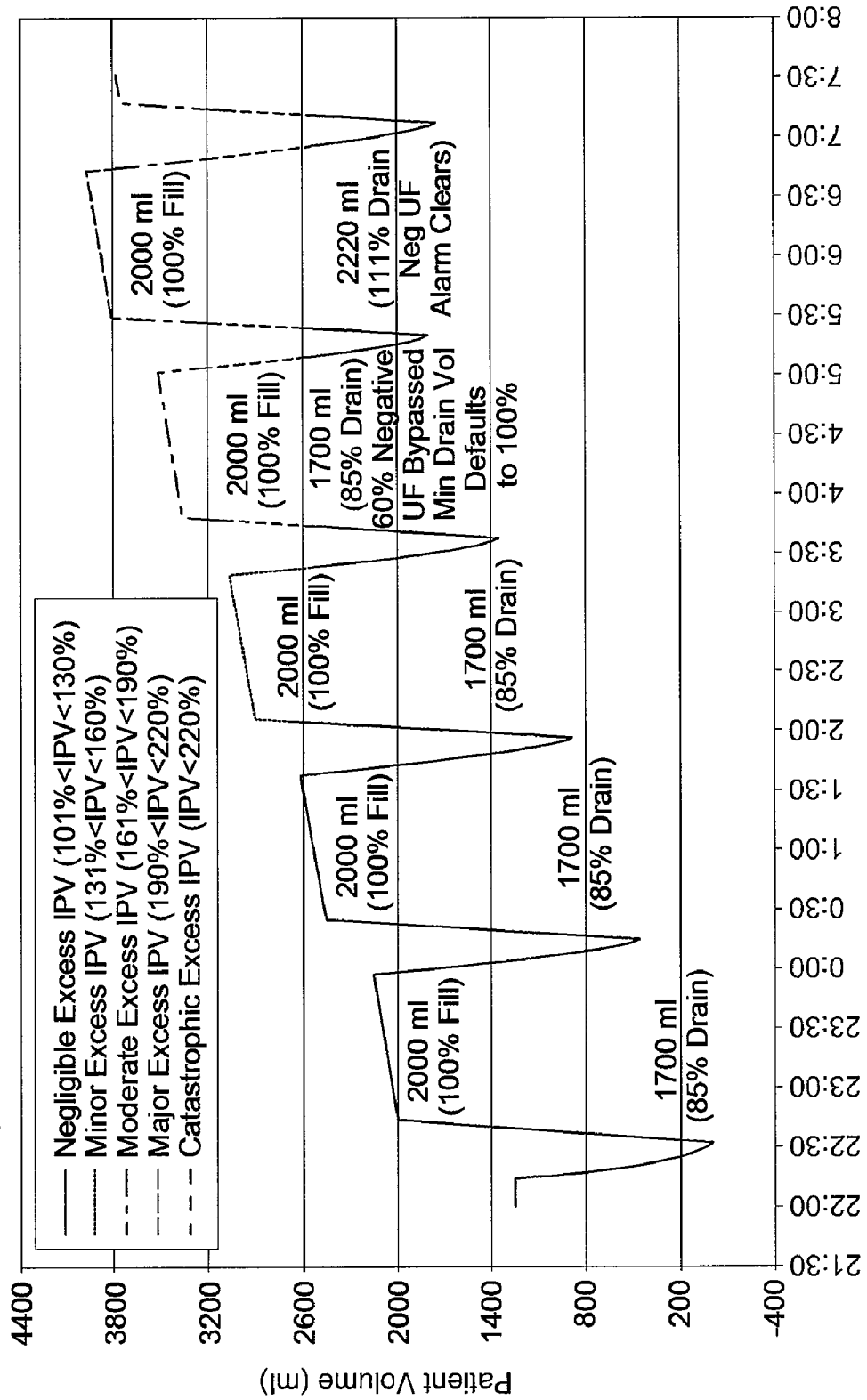
FIG. 4 is an IPV versus time graph showing an example therapy in which a continuous cycling peritoneal dialysis ("CCPD") treatment uses a total volume of dialysis fluid but accumulates a large IPV due to incomplete drains.

FIG. 4 illustrates a therapy in which successive drains just meet the minimum 85% drain volume and system 10 advances the therapy in each case to the next full fill. System 10 allows the intra-peritoneal volume to increase past the 130% of prescribed fill volume limit (2600 ml, after third fill), through the 160% of prescribed fill volume limit (3200 ml, after fourth fill) and into the 190% of prescribed fill volume limit (3800 ml, after fifth fill). The actual UF per cycle in the therapy of FIG. 4 is 150 ml per cycle which equals 7.5% of the 2000 ml fill volume.

System 10 in FIG. 4 posts a negative UF alarm when drain 4 ends with the minimum drain percentage just met because the cumulative negative UF has reached its limit, e.g., 1200 ml (four drains×15% of 2000 ml). The patient or caregiver in the illustrated example elects to bypass the negative UF alarm, so that system 10 advances to the fifth full fill, in which case the patient's intra-peritoneal volume exceeds a 190% of the fill volume limit (1.9×2000=3800 ml).

The therapy illustrated by FIG. 4 fills the patient with 2000 ml of fluid during each of the night fills using all 10,000 ml of solution available for use during therapy. However, during this therapy, the patient's IPV reaches 3950 ml, which is 197.5% of the prescribed fill volume. Furthermore, the patient encounters and has to address an alarm (negative UF) that interrupts his/her sleep.

Figure 5:
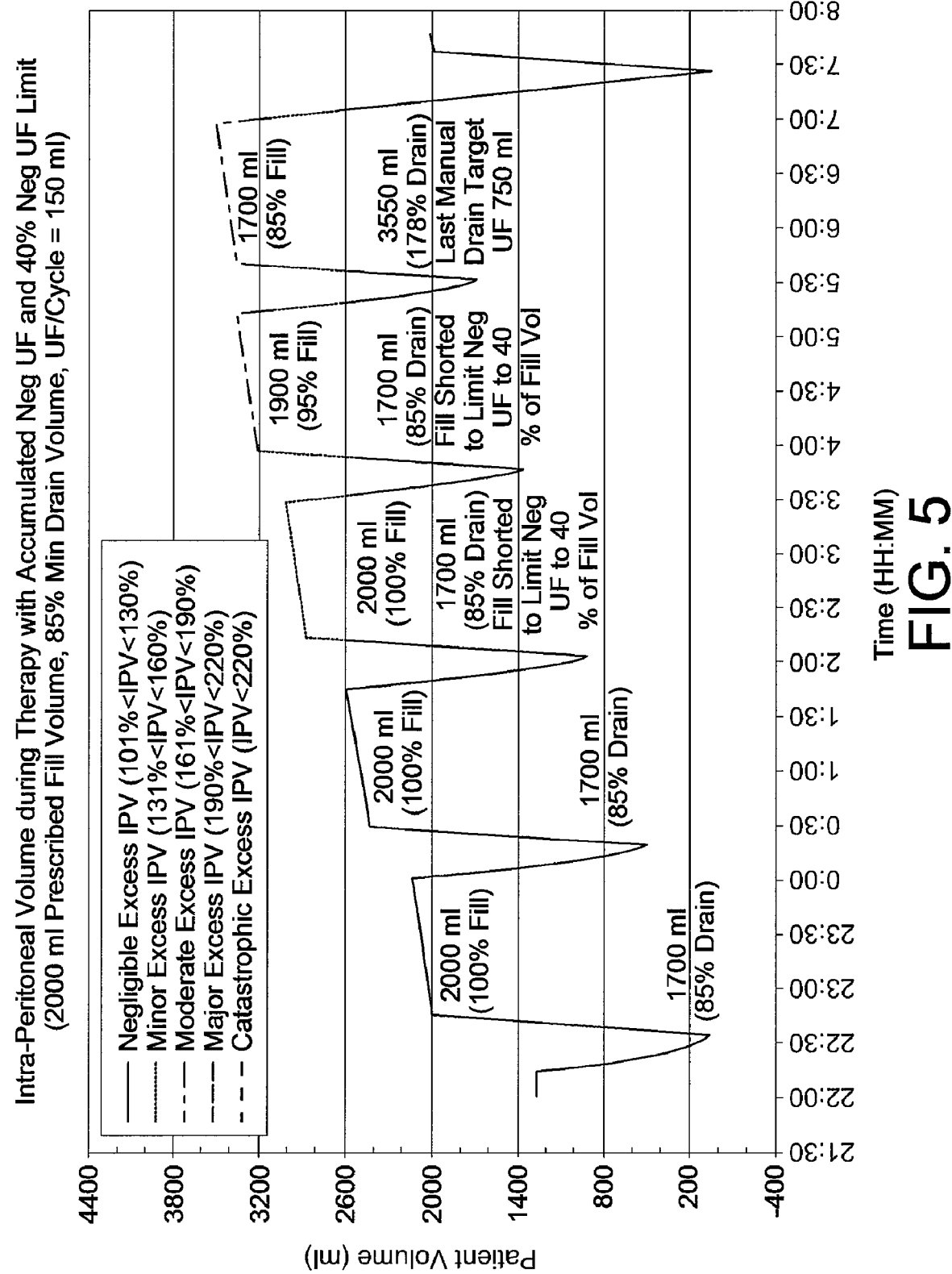
FIG. 5 is an IPV versus time graph showing an example therapy in which a continuous cycling peritoneal dialysis ("CCPD") treatment accumulates less IPV than the treatment of FIG. 4 but does not use a total volume of dialysis fluid.

FIG. 5 is illustrative of a therapy per the first step in an embodiment in which the patient volume stays below 190% of the prescribed fill volume. The patient does not encounter any alarms during the night. As seen, the therapy of FIG. 5 encounters the same drain issues as the therapy illustrated in FIG. 2. Drains 1 through 4 each end with only 85% of the preceding fill volume recovered. Cumulative negative UF increases in 15% steps to 45% at the end of drain 3.

System 10 in the example of FIG. 4 places a 40% limit on negative UF (as opposed to 60% (=1200/2000 in FIG. 4), so that system 10 causes Fill 4 to be shorted by 5%, limiting the negative UF at 40%. System 10 shorts Fill 5 by 15% because Drain 4 was also 15% short. The maximum value for the IPV is 3550 ml (177.5% of prescribed fill volume) during this therapy. The 40% negative UF limit could have been set to a lower value, such as 30%, limiting the maximum IPV to 3250 ml.

The therapy illustrated in FIG. 5 prevented the IPV from exceeding 190% of the prescribed fill volume but did allow the IPV to exceed 160% of the prescribed fill volume. The therapy of FIG. 5 used only 9,600 ml of the 10,000 ml of dialysis fluid that was available. Assuming the fluid could have been used to its maximum potential, the therapy illustrated in FIG. 3 was 96% effective in delivering the maximum possible therapeutic benefit. The therapies illustrated in FIGS. 3 and 4, on the other hand, were 100% effective.

The therapies illustrated in FIGS. 4 and 5 are considered to be CCPD therapies because all drains are prescribed to go to empty. The only drains that actually made it to empty, however, were the initial drain and the last drain in which the patient was awake and could move around, or sit up, to drain fully. The CCPD therapies are accordingly pseudo-tidal in nature. If they had been programmed as tidal therapies with a tidal percent of 85%, all of the drains in FIGS. 4 and 5 would have ended when 85% of the programmed fill volume plus expected UF had been drained. The following fills would have brought the patient volume back to 100% of the programmed fill volume.

Figure 6A:
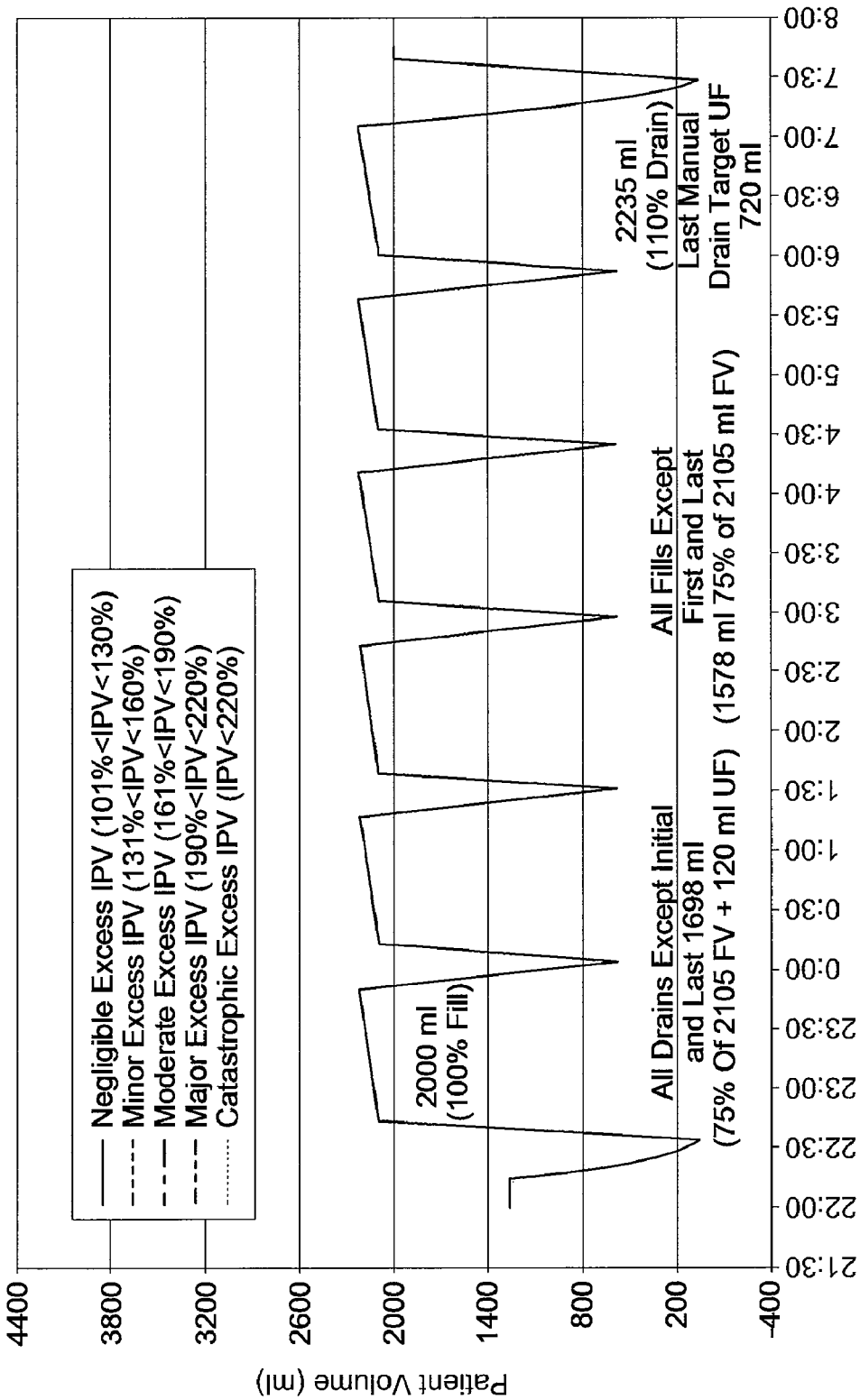
FIGS. 6A-6C are IPV versus time graphs showing two example therapy performed according to the principles of the present disclosure.
Figure 6B:
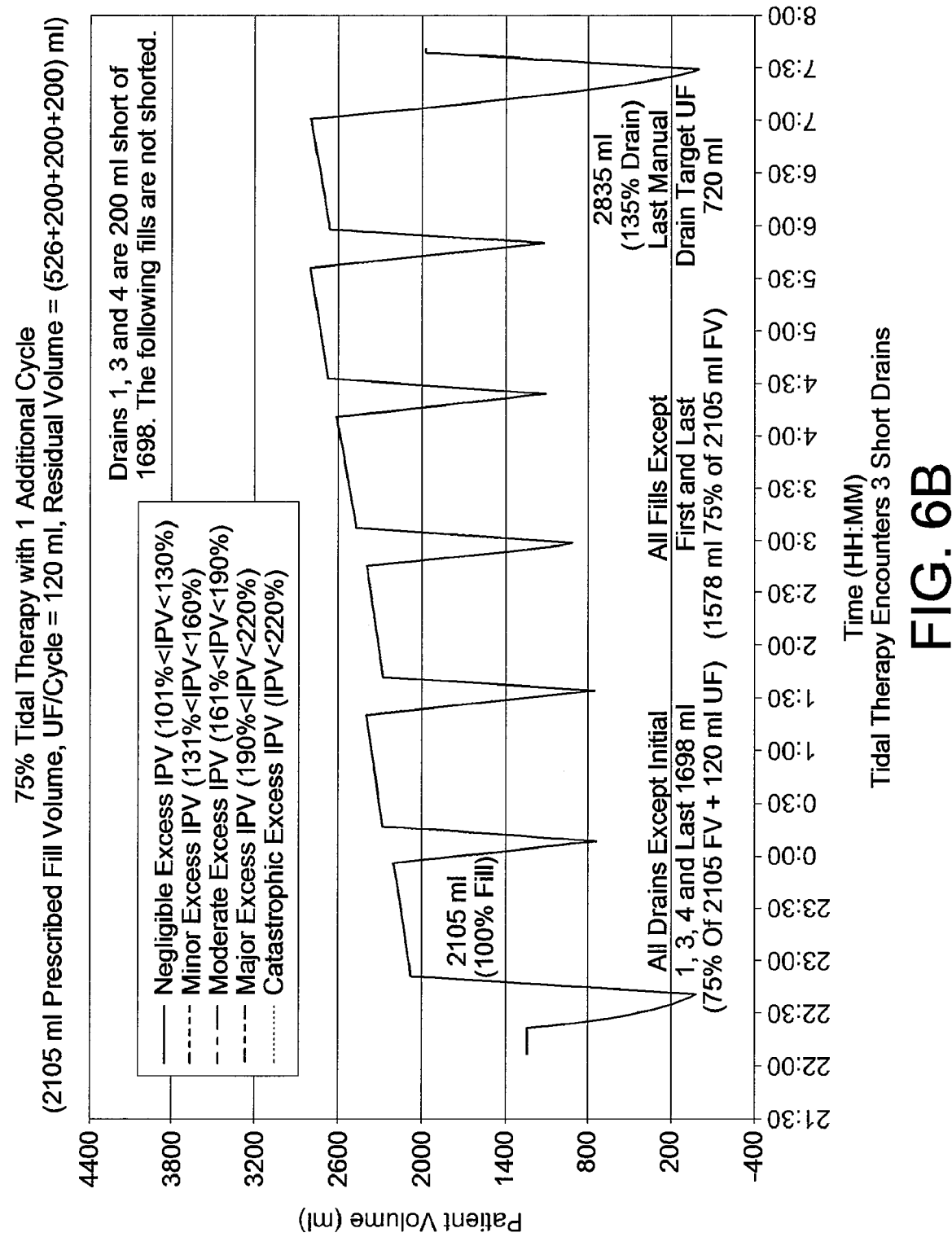
Figure 6C:
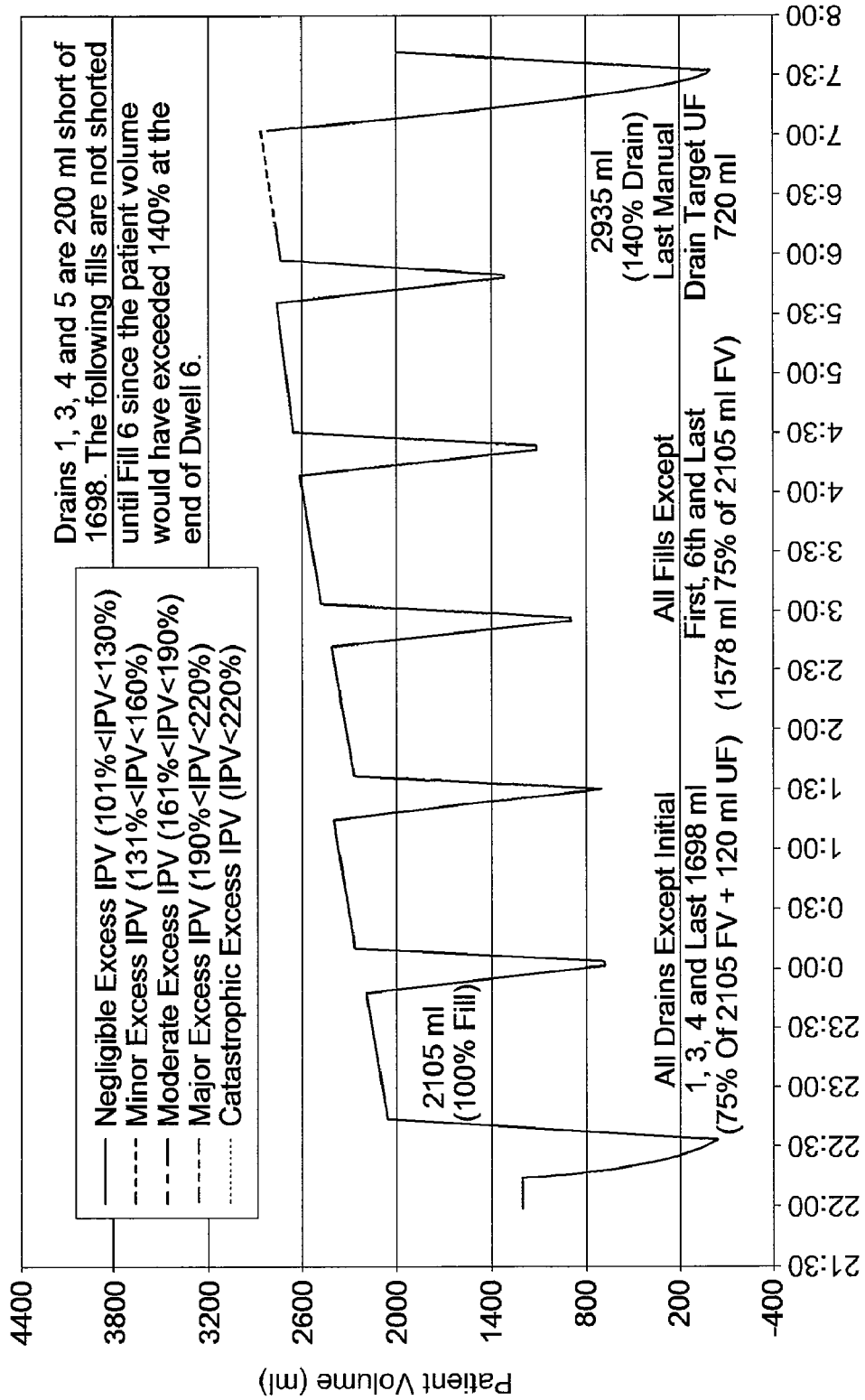

FIGS. 6A-6C and FIGS. 7A-7E demonstrate the operation of steps 2 and 3 of a method of one embodiment, with respectively, 75% and 65% tidal volumes, rather than the 85% discussed above with respect to FIG. 5. In FIGS. 6A-6C, the operation of a 75% tidal system is depicted, each with an additional cycle as compared to FIG. 5. In FIG. 6A, the system operates as intended, and in this case, an "ideal" patient responds as intended. In FIG. 6A, 2000 ml is used for the first, 100% fill, and all drains except the first and the last are about 1698 ml. This represents 75% of a 2105 ml fill volume and a calculated 120 ml UF. Note that 6 cycles with 120 ml of UF would remove a total of about 720 ml ultrafiltrate over the duration of the nocturnal therapy. The patient volume does not appear to reach even 2200 ml, i.e., does not even reach 10% over the initial patient volume (IPV). As seen in FIG. 6A, each cycle lasts about 1.5 hours and there are a total of six cycles, for a 9-hour therapy, from about 10:30 pm to about 7:30 the next morning.

In FIG. 6B, the same 2105 ml fill volume is used, but in this case, the patient does not drain as expected. The same drain volume, about 1698 ml, is expected, but does not occur in every drain cycle. In the first drain cycle, only about 1450 ml is drained. In addition, drains 3 and 4 are also short, as can be seen by observing the increasing patient volume fill. Even in this situation, however, the peak patient fill volume appears to reach about 2800 ml, i.e., about 140% of IPV, which is not ideal but is considerably less than the 161% required for a "moderate excess" intraperitoneal volume and is far less than the previous situation seen in FIG. 4 or FIG. 5.

The total prescribed therapy volume is also used in the therapy depicted in FIG. 6C. In FIG. 6C, cycles 1, 3, 4 and 5 have short drains, as seen by the increasing patient fill volume over the six cycles, rising to almost 3000 ml. The tidal therapy shown in FIG. 6C shorts the last fill by about 100 ml in order to limit the IPV to 140% of the prescribed fill volume. This reduces the effectiveness of the 10,000 ml night therapy by about 1% based upon the actual fluid volume used, (10000−100)/10000=99%. Note that no alarms were necessary in any of the therapies depicted in FIGS. 6A-6C.

Figure 7A:
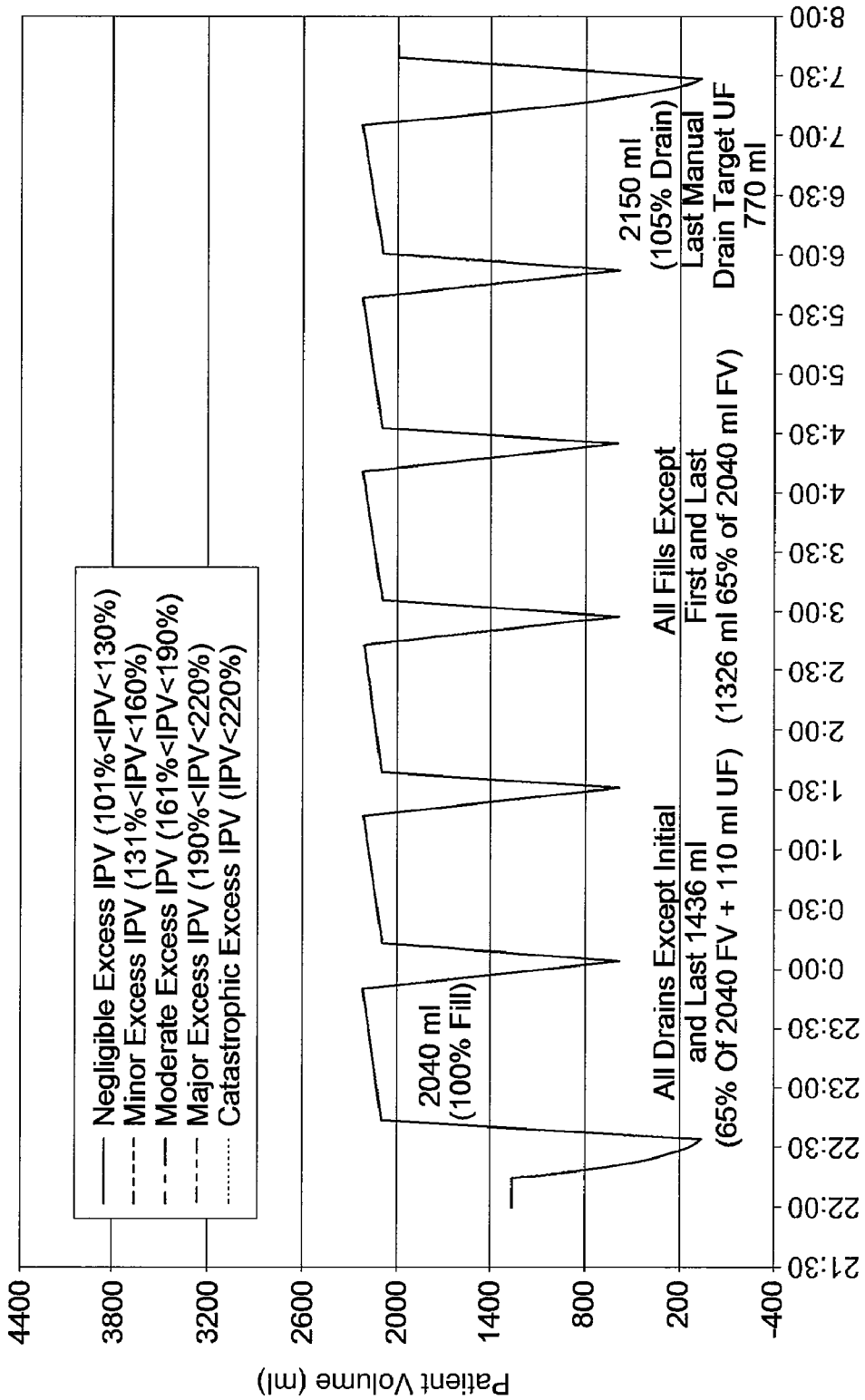
FIGS. 7A-7E are IPV versus time graphs showing additional example therapies performed according to the principles of the present disclosure.

If a fluid volume exceeding a predetermined limit remains unused nearly every day, a switch can be made from a 75% tidal therapy to a 65% tidal therapy allowing the based residual volume to increase by another 10%. FIGS. 7A-7E illustrate how such a therapy would limit the IPV while using all of the available fluid and maintaining the predicted dwell times. The patient would seldom get a low drain volume alarm or a negative UF alarm when the base therapy is assumed to be tidal instead of CCPD. In FIG. 7A, the therapy is now 65% tidal therapy, with 2 additional cycles over those of FIG. 5 required in order to use the total prescribed therapy volume. FIG. 7A depicts a relatively ideal situation, in which a patient has all drains, except the first and the last, at about 1436 ml, representing 65% of 2040 ml of fill volume and 110 ml UF (110 ml UF over 7 cycles would remove about 770 ml UF). Each cycle is now a little shorter, about 1 hour and 15 minutes, for a total therapy time of about 8 hours and 45 minutes. In this idealized situation, the patient fill volume does not exceed 2200 ml, that is, does not go over about 110% of the prescribed fill volume.

Figure 7B:
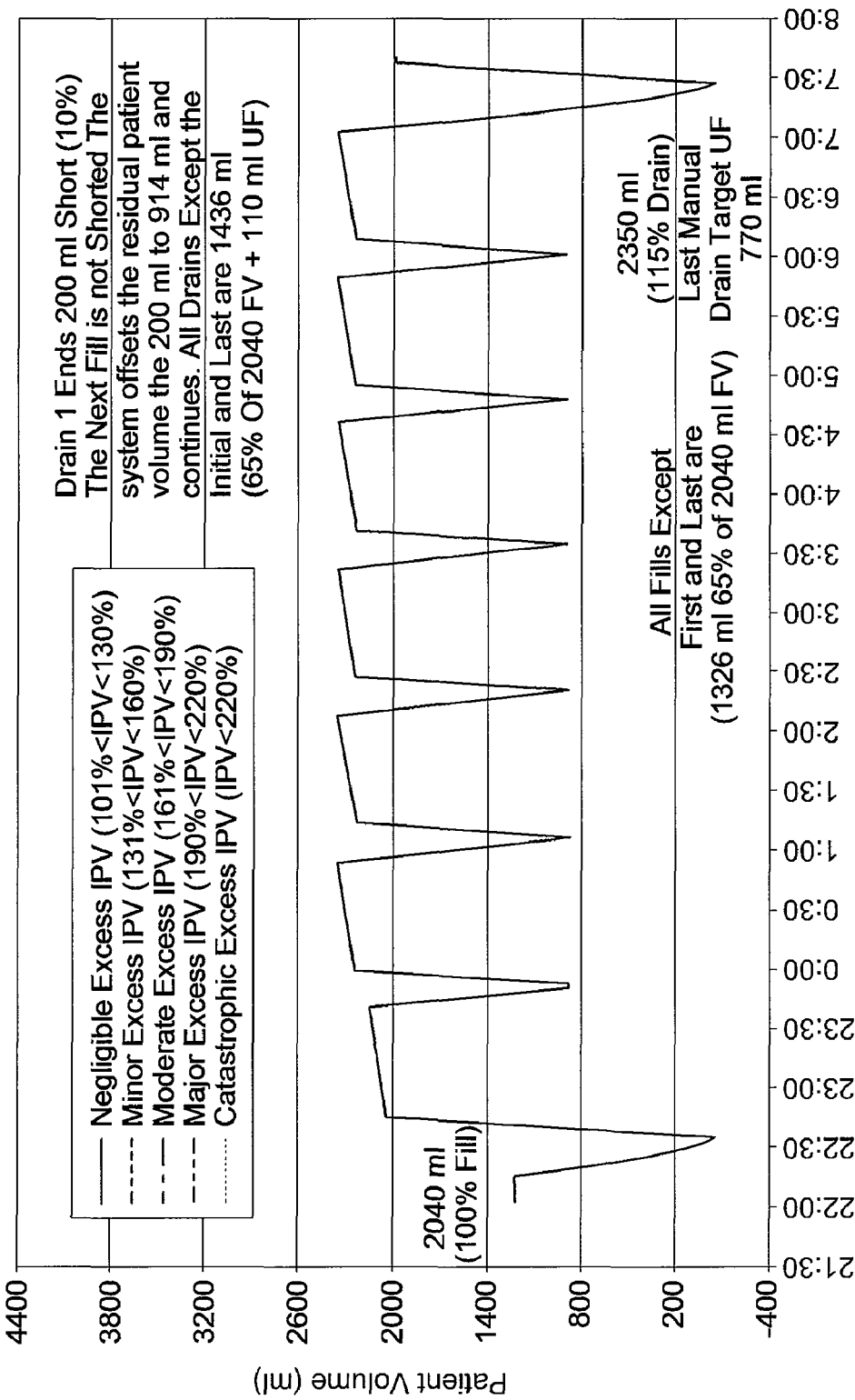
Figure 7C:
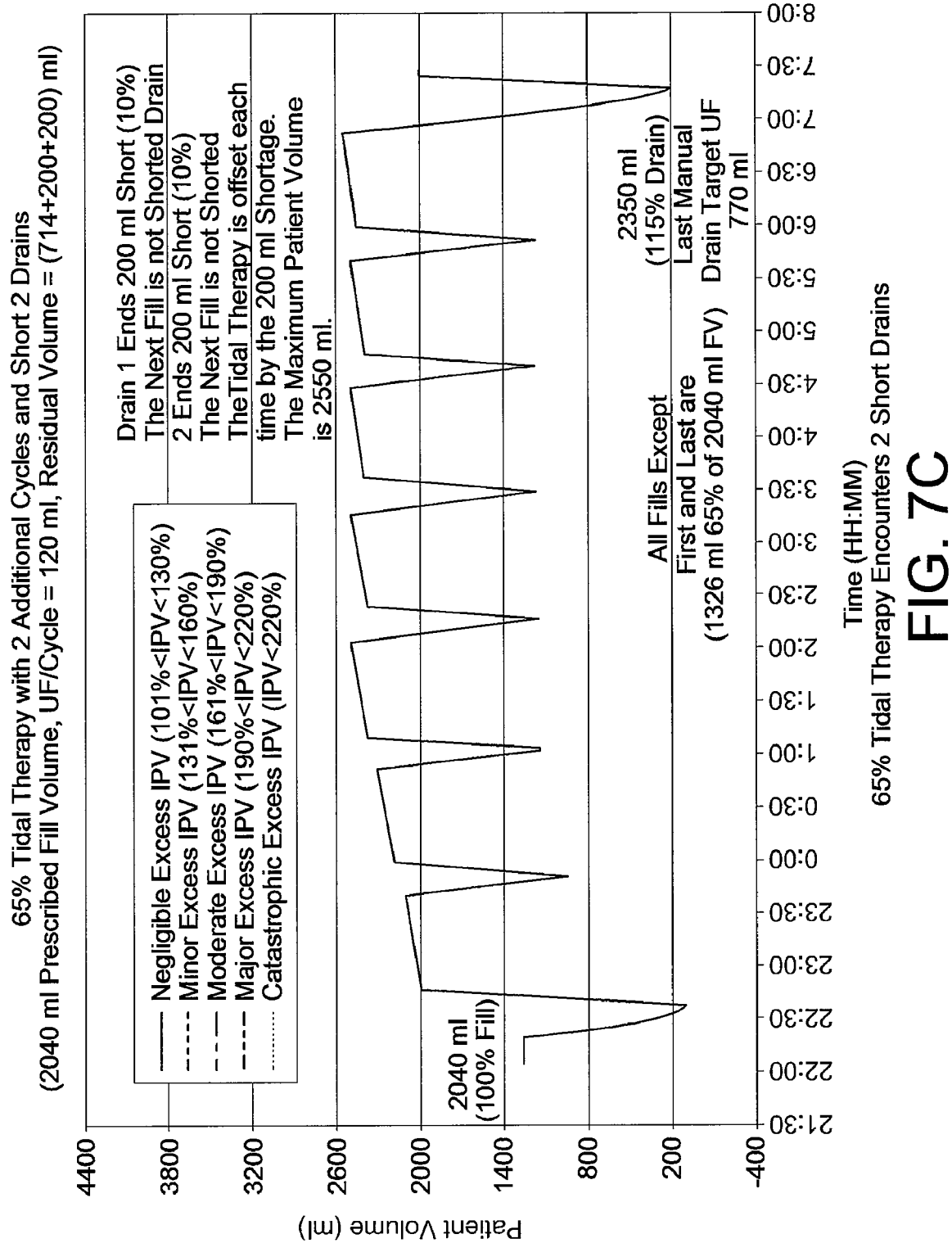

The patient response in FIG. 7B is somewhat less ideal, with the first drain about 200 ml short (about 10% less than expected). Each drain is expected to be about 1436 ml, with 65% of 2040 ml fill volume (1326 ml) and 110 ml UF. While the first drain is short, the remaining drains are on target until the last drain, which is about 2350 ml. This therapy is still very well-behaved, with no alarms and patient IPV not exceeding the negligible excess level (less than 130% IPV). In FIG. 7C, however, several drains are short, e.g., the first and second drains are about 200 ml short. The tidal therapy is offset each time by the 200 ml drain shortage, i.e., the tidal therapy volume increases by about 200 ml. Nevertheless, since the patient volume does not exceed the negligible excess level, the subsequent fills on cycles 2 and 3 are not shorted. Thus, the total therapy volume is used and the patient is still not upset by unnecessary alarms during the nocturnal therapy.

Of course, if the volume were to exceed one of the thresholds, the controls could be programmed to short one or more of the cycle fill volumes.

Figure 7D:
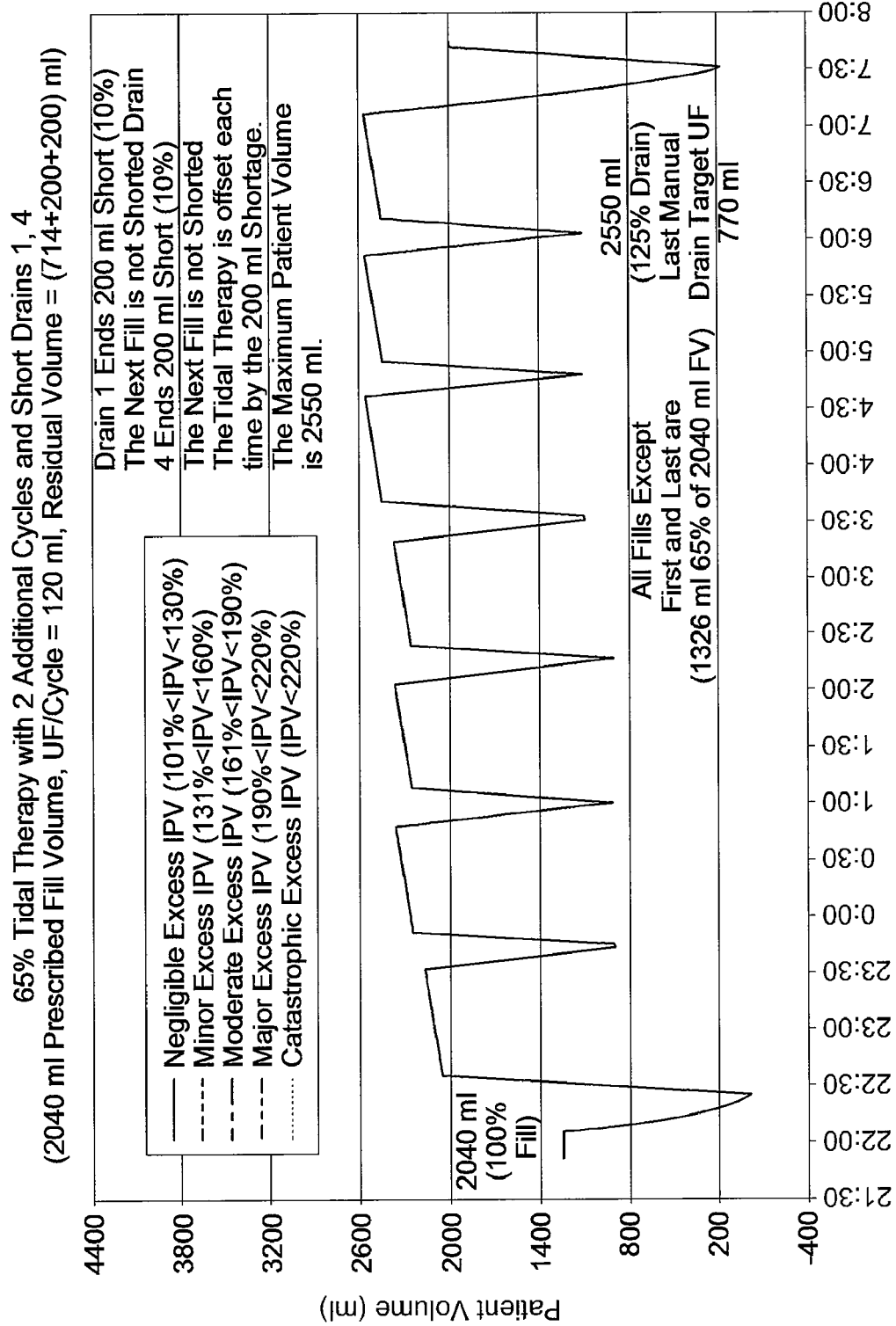
Figure 7E:
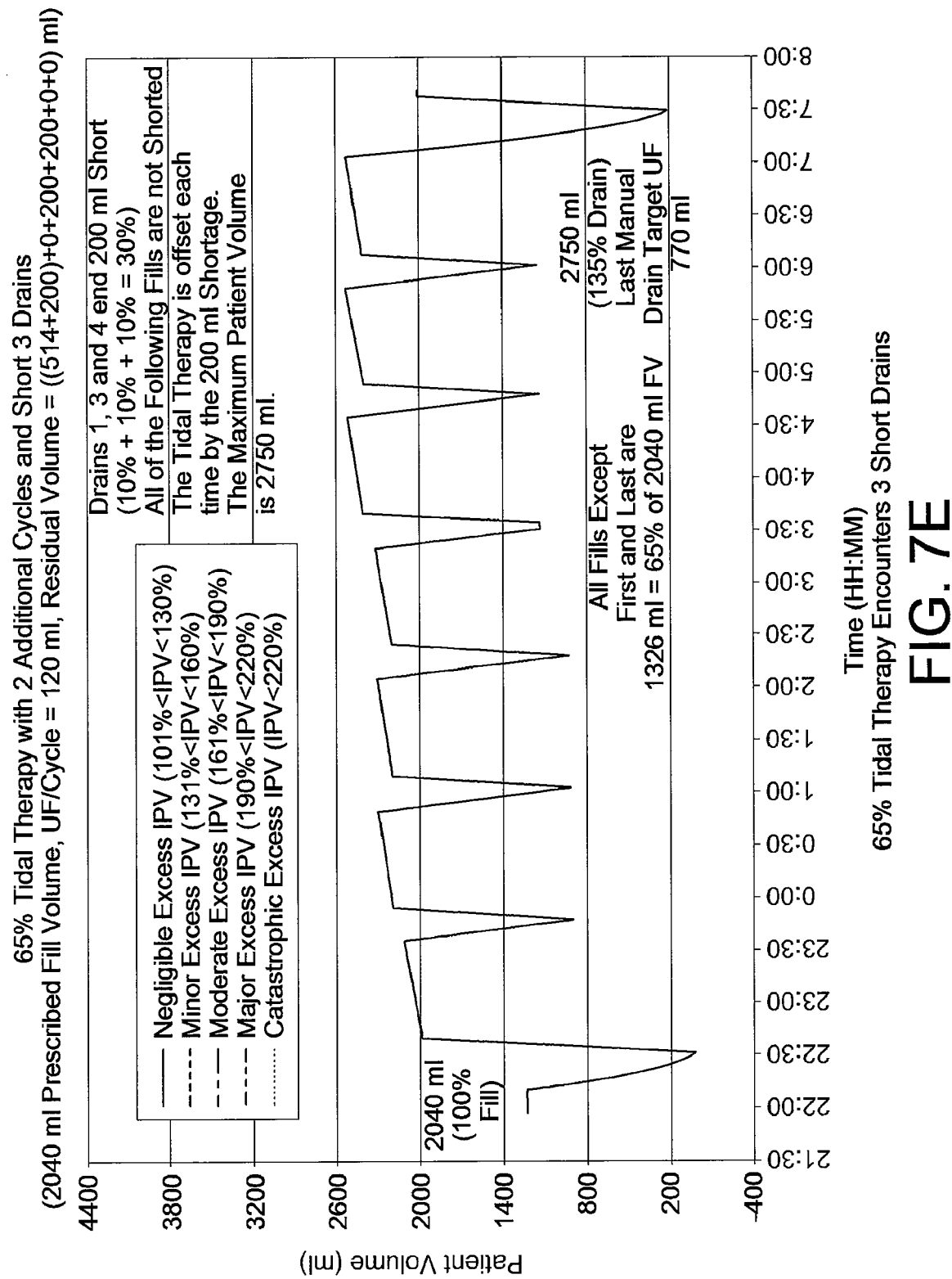

FIG. 7D depicts another patient therapy with some of the same shortcomings as FIG. 7C. As in FIG. 7C, there are two additional cycles and two short drains, drains 1 and 4, as seen by the increase in IPV at cycles 2 and 5. The negligible excess level is not exceeded, and as before, there are no alarms since the IPV level does not exceed the negligible excess level of less than 130% of patient volume. The total therapy volume is also used in this situation. FIG. 7E depicts another therapy performance. In this depiction, the first, second and fourth drains are each short by about 200 ml. Thus, the total patient volume rises by about 600 ml, which is still within the negligible excess IPV limit.

The therapies of FIGS. 6A-6C and FIGS. 7A-7E limit the maximum patient fill volume while using all the dialysis solution that is prescribed and available. At the same time, the therapy may be programmed to withhold therapy volume if the patient drain is much less than expected and the patient fill volume would cross an unacceptable threshold. Extra cycles may be added, each cycle an appropriate amount shorter, so that each fill is as effective as possible, the available solution is used, the available time is used, and alarms that disturb and disrupt a patient are kept to a minimum.

If drains continue to be shorted beyond the three shown in FIG. 7E, however, such that maximum IPV grows (or is predicted to grow) to 2650 ml or greater (thirty percent or greater than initial fill volume), system 10 will stop offsetting the base patient volume and will short the next fill. The offset of the base patient volume is limited to 30% of the initial fill volume less the expected UF per cycle. System 10 in one embodiment posts a low drain volume alarm if ending the drain would result in an IPV on the next fill that would exceed 130% of the programmed fill volume not including UF. In one embodiment, system 10 limits the maximum IPV to 130% of the programmed fill volume (initial fill volume for tidal therapies). The offset limit can be adjusted to a value other than 30% if necessary, for example from 20% to 40%. The offset limit with tidal is similar to the negative UF limit that was imposed on the CCPD Therapy.

The method disclosed herein may progress gradually from an 85% CCPD (pseudo tidal) therapy to a 75% tidal therapy to a 65% tidal therapy and even to a 55% tidal therapy as it seeks to use all of the available dialysis solution, minimize the increased intra peritoneal volume and minimize the number of low drain alarms. Patient volume offsets will be allowed as long as they do not exceed a predetermined programmable limit that will be defaulted to 30%. Cycles will be added each time the tidal percentage decreases so that all of the dialysis solution volume is used. The base patient fill volume may also be adjusted up or down 5-10% during this process so that no fluid volume is wasted.

As discussed in more detail below, in one embodiment, system 10 trends UF based upon the dialysis solution used. For example, for a particular patient, the expected UF per therapy might be 500 ml with 1.5% dextrose, 750 ml with 2.0% dextrose, 1000 ml with 2.5% dextrose and 1500 ml with 4.25% dextrose. System 10 in one embodiment is programmed to notify the patient if the programmed total UF at the beginning of treatment differs by more than 20% from the trended UF for the particular dextrose concentration being used.

It is believed that system 10 will encounter fewer low drain volume alarms and virtually no negative UF alarms when compared to current CCPD therapies. The system will consistently use the total dialysate volume available and will not allow the patient's IPV to exceed 160% of the programmed fill volume.

Figure 8:
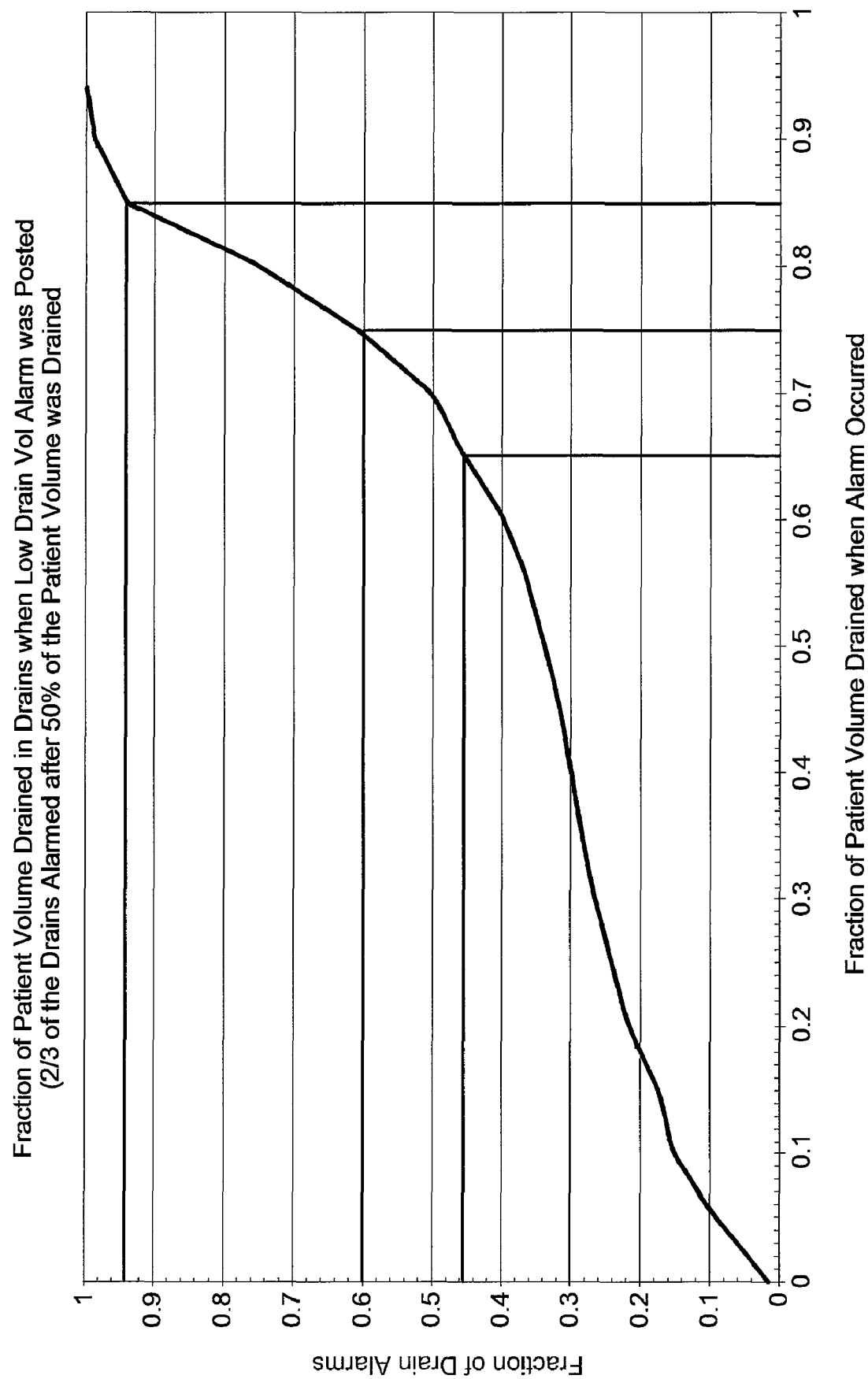
FIG. 8 is a chart showing percentages of when low drain alarms occur relative to how much fluid has been drained from the patient when the alarm occurs.

FIG. 8 shows that the occurrence of non-initial drain alarms that are posted during a therapy would be expected to decrease to less than half (0.450/0.94) its current number if the minimum drain percentage were decreased from 85% to 65%. The alarm decrease would be to about ⅝ (0.6/0.94) if the minimum drain percentage were decreased to 75% from 65%.

System 10 in one embodiment also averages both the per cycle fill volume and per cycle dwell time after manual drains or bypasses in fill that alter the volume of fluid remaining, as will be explained below for FIGS. 11A-11C. System 10 recalculates the therapy after such manual drain or bypass in fill that alters the volume of fluid remaining, calculating a revised average dwell time for each the remaining cycles. System 10 also calculates a revised (potentially) remaining number of cycles, which is calculated by dividing the total remaining therapy fluid volume less a "last fill" or "wet day" fill volume by the prescribed fill volume:

cycles remaining=(total remaining therapy volume−
last fill volume (if any))/programmed fill volume System 10 in one implementation rounds up a fractional portion of a cycle if it is greater than 0.4 and divides both the total remaining therapy volume and therapy time equally over the rounded-up number of cycles remaining. Otherwise, the calculated number of cycles is truncated, and system 10 divides both the total remaining therapy volume and therapy time equally over the truncated number of cycles remaining.

Figure 9:
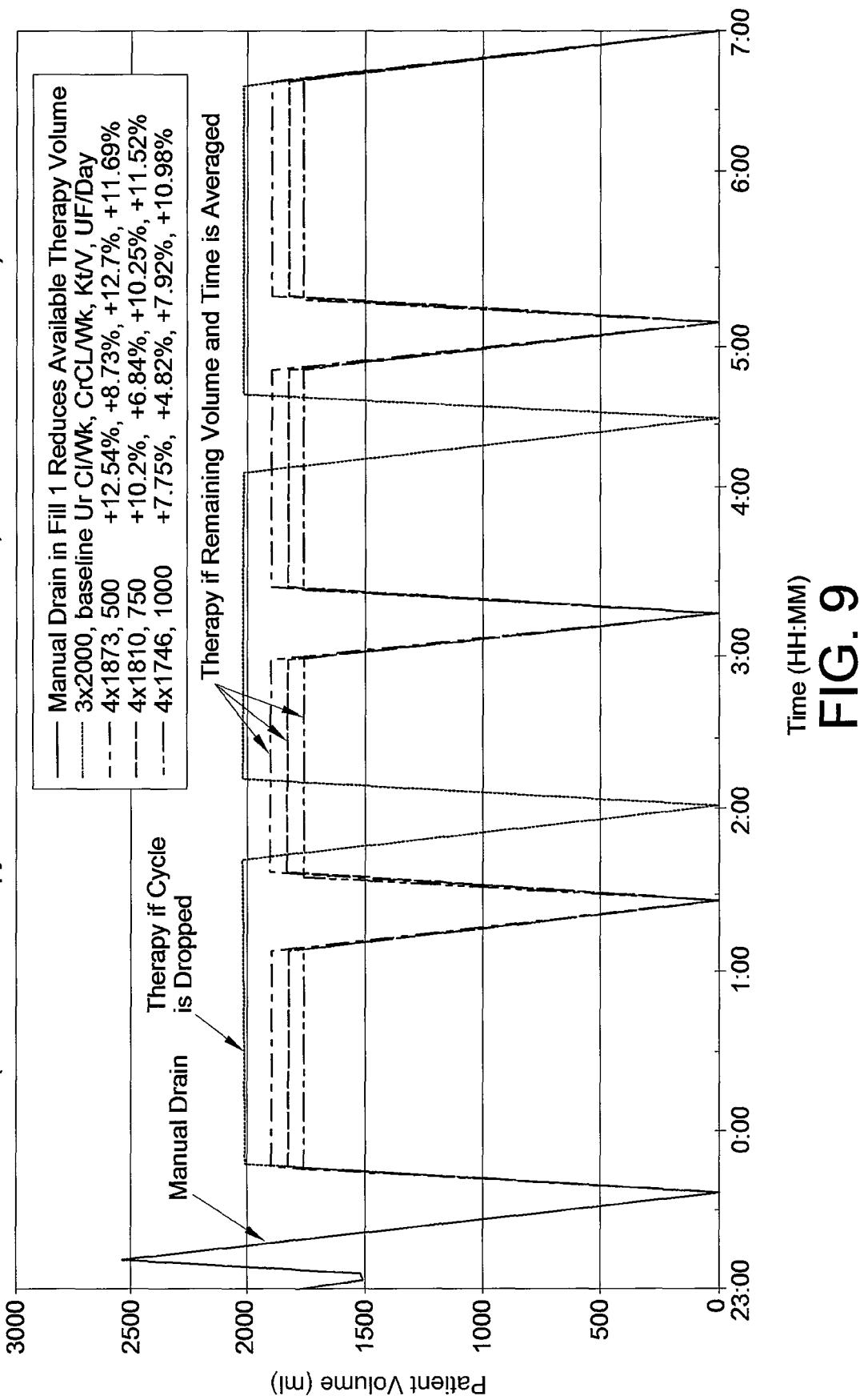
FIGS. 9 and 10 is an IPV versus time graph showing other example therapies performed after an occasion when a previous fill uses less than, more than, respectively, a prescribed amount of fresh dialysate.
Figure 10:
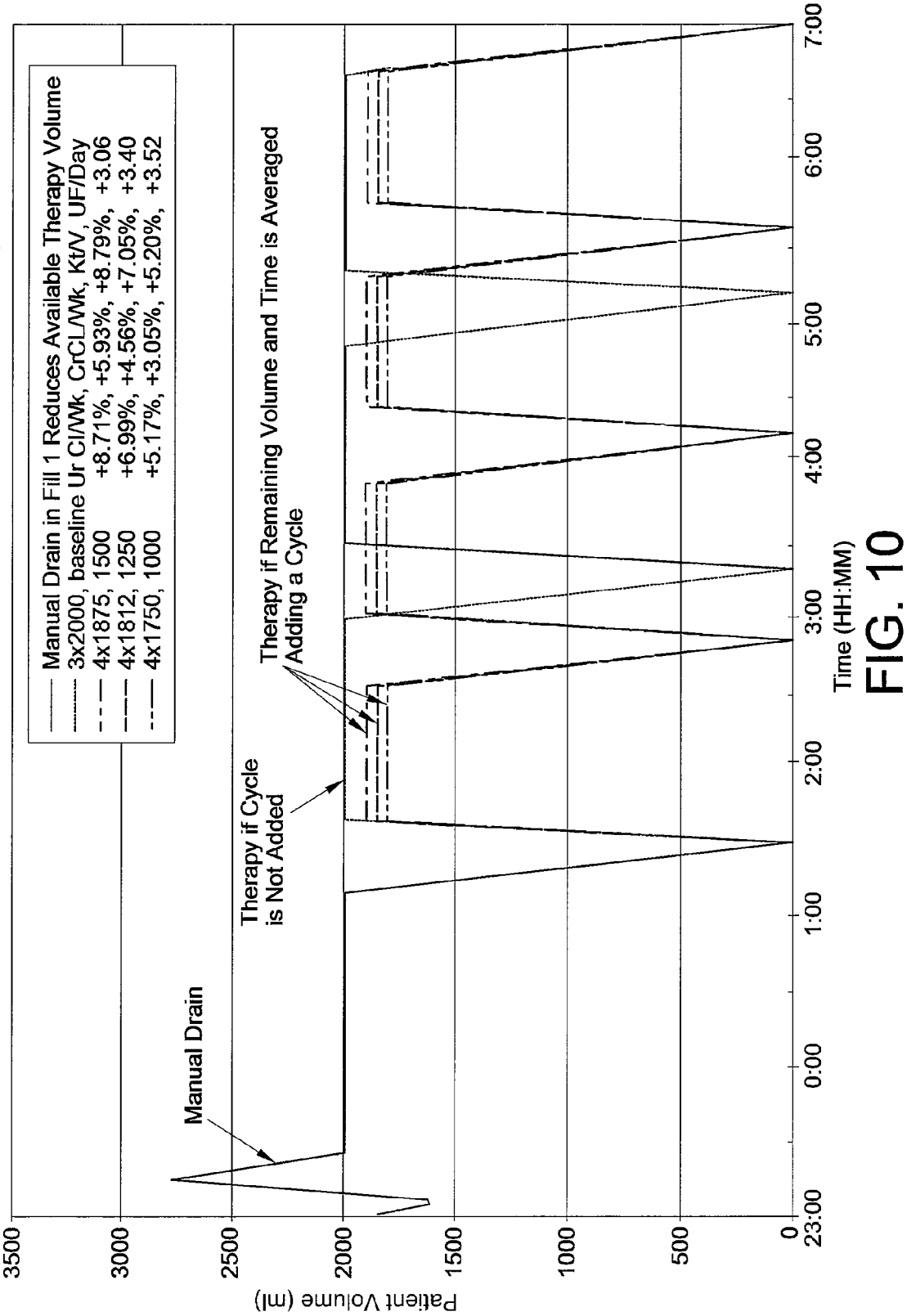

FIGS. 9-10 illustrate how cycles can be added or at least not dropped in order to use all of the available fluid. The same concept carries over into drains when cycles are added. The principle is to use as much fluid as possible so as to give the maximum benefit to the patient while wasting as little fluid as possible.

FIG. 9 illustrates a treatment in which the first fill uses less fluid than normal because of a bypass of the fill. For example, if a user feels full and uses a manual drain or does not use a full fill. As a result, 500, 750 or 1000 ml of fluid (out of 2000 ml) was used in the first fill. System 10 spreads the remaining volume evenly over the remaining cycles, which are increased in FIG. 8 from three to four. If the full 2000 ml is used in the first fill then the top or highest fill line shows that the therapy proceeds with three additional 2000 ml fills for total of 8000 ml. If only 500 ml is used in the first fill then the second or next highest fill line shows that the four fills at about 1875 ml are performed to use the total 8000 ml. If only 750 ml is used in the first fill then the third line shows that the four fills of about 1810 ml are performed to use the total 8000 ml. If only 1000 ml is used in the first fill then the lowest of the four fill lines shows that the four fills at about 1746 ml are performed to use the total 8000 ml. The result again is a more effective therapy.

FIG. 10 illustrates a scenario in which the first fill uses more fluid than normal because of a manual drain in the first fill. Here, system 10 averages the remaining therapy volume over the remaining four cycles instead of dropping a cycle and retaining the original fill volume. The result again is a more effective therapy.

Figure 11A:
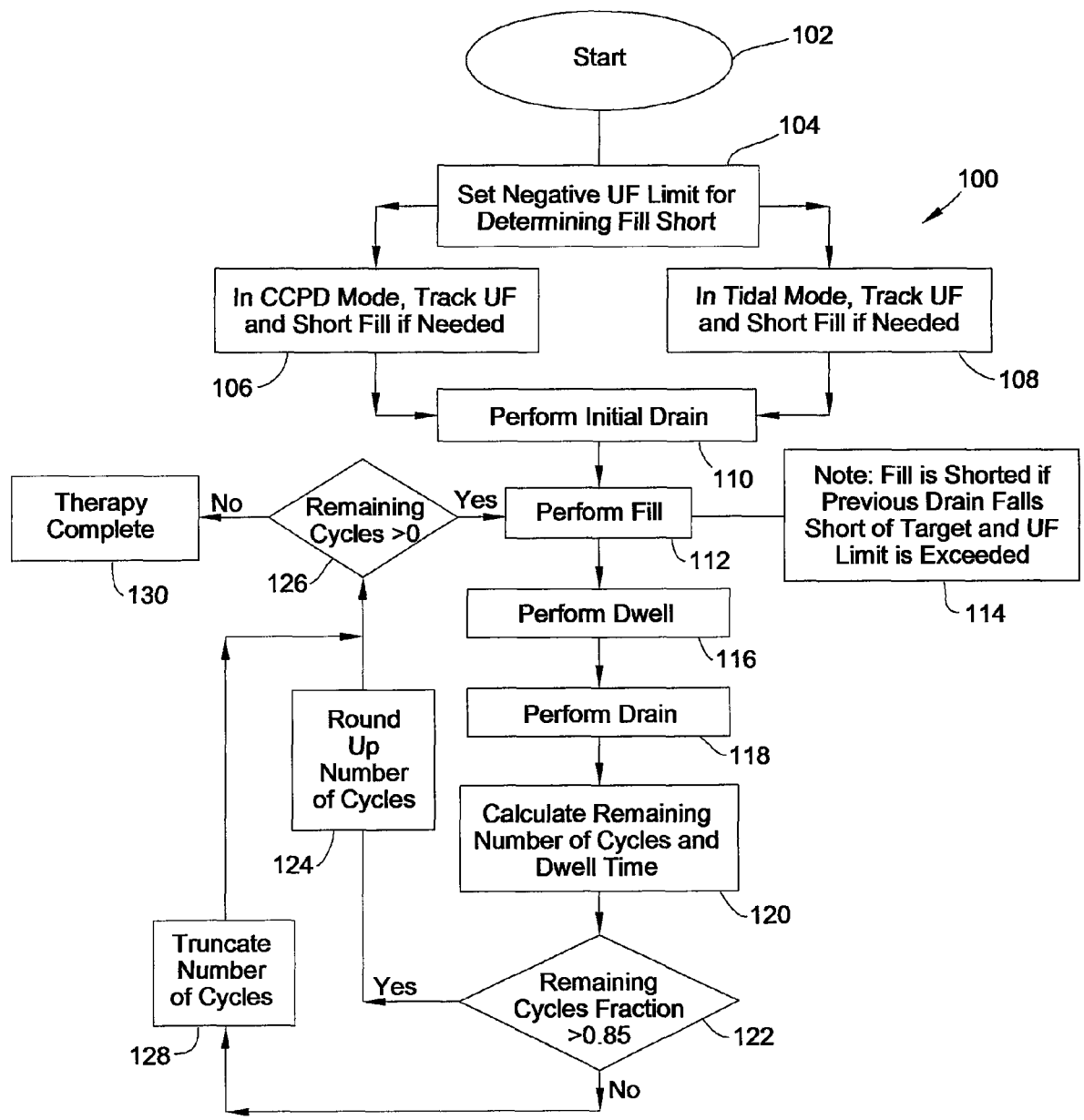
FIGS. 11A-11C are logic flow diagram illustrating embodiments of methods performed by the system of the present disclosure.

Referring now to FIG. 11A, flow diagram 100 illustrates one embodiment of a system 10 which may be used in either CCPD or tidal mode. The method begins at oval 102. At block 104, the user sets a programmable negative UF limit that is used to determine when to use shorter fill volumes after one or more incomplete drains when running a CCPD therapy or a Tidal therapy. As seen in blocks 106, 108, the system 10 tracks UF and calls for a short fill if needed, in both CCPD mode and in Tidal mode.

At block 110, system 10 performs an initial drain, followed by block 112 with a fill. Per block 114, for drains after the initial drain, a shorter fill volume will be used, i.e., the fill is shorted, if the previous drain falls short of the target volume and the UF limit is exceeded. After the fill, a dwell at block 116 is performed, the dwell calculated as discussed below. After the dwell, a drain is performed at block 118. Based on the drain, the number of remaining cycles and the dwell time is calculated at block 120. The dwell time is calculated at block 120 to use all the allocated therapy time. In both the CCPD and tidal modes, system 10 tracks UF, offsets the residual patient volume and maintains the tidal fill volume if a tidal drain is incomplete as long as the sum of the increases in residual patient volume and expected UF do not exceed the negative UF Limit.

For CCPD therapies, system 10 calculates the remaining number of CCPD cycles using the equation: Cycles Remaining=(total remaining therapy volume−last fill volume (if any))/(programmed fill volume)

For Tidal therapies after an incomplete tidal drain, or after a complete full drain, system 10 calculates the remaining number of tidal cycles using the equation: Cycles Remaining=1+(Remaining Therapy Volume−Fill Volume−Last Fill Volume)/(Tidal PerCent*Fill Volume).

For Tidal therapies after a complete tidal drain, system 10 calculates the remaining number of tidal cycles using the equation: Cycles Remaining=(Remaining Therapy Volume−Last Fill Volume)/(Tidal PerCent*Fill Volume).

At diamond 122, if the fractional number of cycles exceeds 0.85, the number of cycles is rounded up to the nearest integer, per block 124. For example, if the fractional number of cycles remaining is 4.9, the number of cycles remaining is rounded up to 5; if the number of cycles remaining is 0.9, the number of cycles remaining is rounded up to 1. At diamond 126, system 10 compares the number of remaining cycles to zero. If the number of cycles remaining is greater than zero, the next fill is performed, per block 112 and the process is repeated. If the number of cycles is zero, the therapy is complete, per block 130.

Returning to diamond 122, if the fractional number of cycles is less than 0.85, the path moves to block 128, where the number of cycles is rounded down or truncated. At the next step, at diamond 126, system 10 compares the number of remaining cycles to zero. If the number of cycles remaining is greater than zero, the next fill is performed, per block 112 and the process is repeated. If the number of cycles is zero, the therapy is complete, per block 130.

Figure 11B:
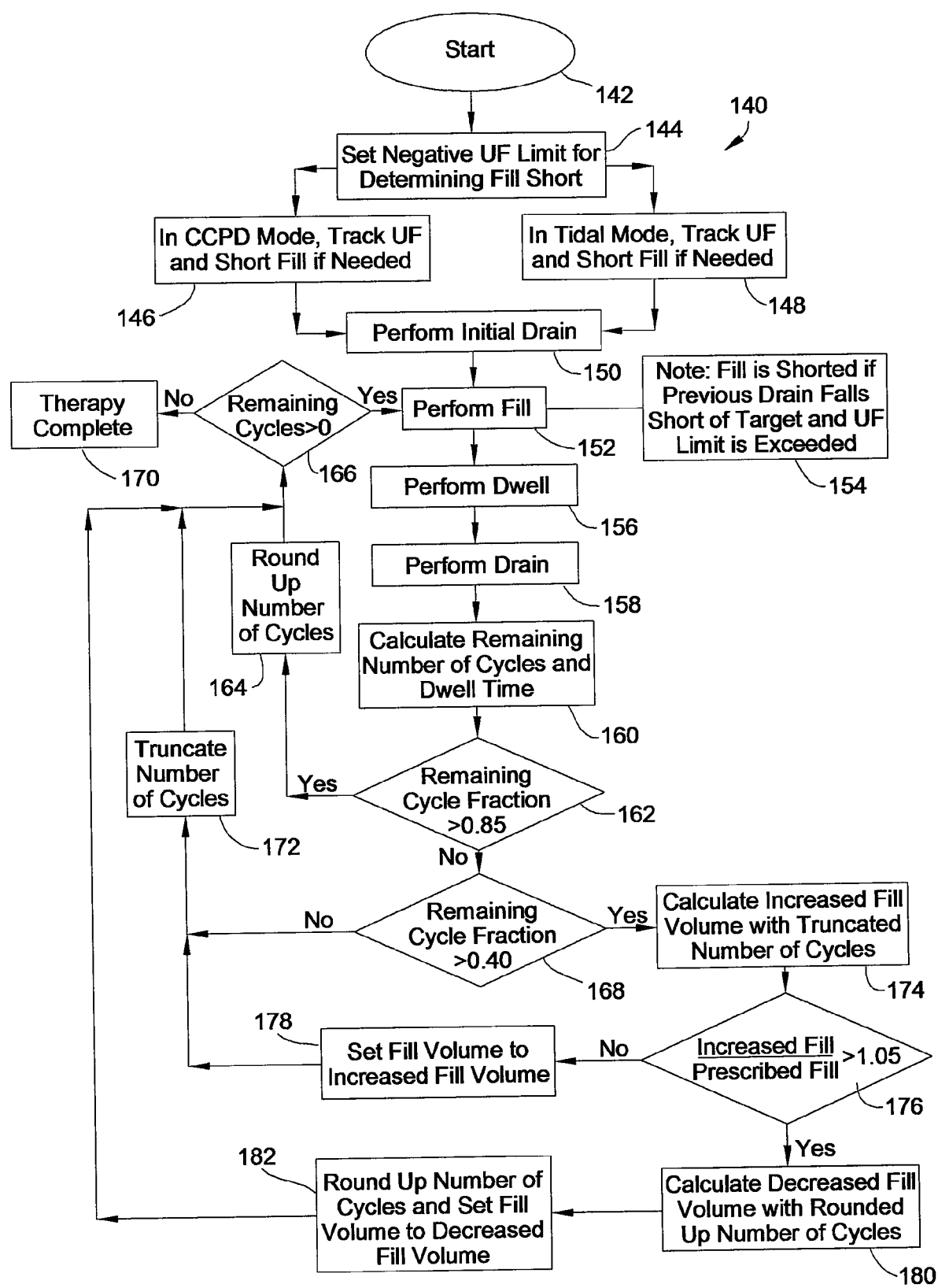

Referring now to FIG. 11B, flow diagram 140 illustrates one embodiment of a system 10 which may be used in either CCPD or tidal mode. The method begins at oval 142. At block 144, the user sets a programmable negative UF limit that is used to determine when to use shorter fill volumes after one or more incomplete drains when running a CCPD therapy or a Tidal therapy. As seen in blocks 146, 148, the system 10 tracks UF and calls for a short fill if needed, in both CCPD mode and in Tidal mode.

At block 150, system 10 performs an initial drain, followed by a fill at block 152. If the previous drain falls short of the target volume and the UF limit is exceeded, then per block 154, for drains after the initial drain, a shorter fill volume will be used, i.e., the fill is shorted. After the fill, a dwell at block 156 is performed, the dwell calculated as discussed below. After the dwell, a drain is performed at block 158. Based on the drain, the number of remaining cycles and the dwell time is calculated at block 160 in order to use all of the allocated therapy time. In both the CCPD and tidal modes, system 10 tracks UF, offsets the residual patient volume and maintains the tidal fill volume if a tidal drain is incomplete, as long as the sum of the increases in residual patient volume and expected UF do not exceed the negative UF Limit.

For CCPD therapies, system 10 calculates the remaining number of CCPD cycles using the equation: Cycles Remaining=(total remaining therapy volume−last fill volume (if any))/(programmed fill volume).

For Tidal therapies after a tidal drain that ends prematurely due to an empty patient, or after a tidal full drain, system 10 calculates the remaining number of tidal cycles using the equation: Cycles Remaining=1+(Remaining Therapy Volume−Fill Volume−Last Fill Volume)/(Tidal PerCent*Fill Volume).

For Tidal therapies after a normal tidal drain, system 10 calculates the remaining number of tidal cycles using the equation: Cycles Remaining=(Remaining Therapy Volume−Last Fill Volume)/(Tidal PerCent*Fill Volume).

At diamond 162, if the fractional number of cycles exceeds 0.85, the number of cycles is rounded up to the nearest integer, per block 164. For example, if the fractional number of cycles remaining is 4.9, the number of cycles remaining is rounded up to 5. At diamond 166, system 10 compares the number of remaining cycles to zero. If the number of cycles remaining is greater than zero, the next fill is performed, per block 152 and the process is repeated. If the number of cycles is zero, the therapy is complete, per block 170.

Returning to diamond 162, if the fractional number of cycles is less than 0.85, the process path moves to diamond 168. At this point, the fractional number of cycles is compared to 0.40 (40% of a cycle). If the fractional number remaining is less than 0.40, the number of cycles is rounded down, or truncated at block 172 and the process moves to diamond 166, where the remaining number of cycles is compared to zero. If the number of cycles remaining is greater than zero, the next fill is performed, per block 152 and the process is repeated. If the number of cycles is zero, the therapy is complete, per block 170.

Returning to diamond 168, if the fractional number of cycles is greater than 0.40, a new higher fill volume is calculated with a truncated number of cycles at block 174. At diamond 176, the ratio of Increased Fill to Prescribed Fill is calculated. If the ratio is not greater than 1.05, i.e., the volume increase is less than 5%, the increased fill volume is taken as the new set point at block 178. The number of cycles is truncated at block 172, and the number of remaining cycles is then compared to zero at diamond 166. If no cycles remain, the therapy is completed at block 170. If 1 or more cycles remains, the process advances to block 152 and is repeated.

Returning to diamond 176, if the increase is greater than 5%, a decreased fill volume is calculated, based on a rounded-up number of cycles at block 180. The number of cycles is rounded up at block 182 and the set fill volume is reset to a decreased fill volume. The process then returns to diamond 166 for another cycle if appropriate.

Example for Patient A: Tables 1, 2, 3 and 4 contain system 10 drain volume/fill volume (DV/FV) ratios, UF/fill (UF/FV) volume and ratios of unused fluid volume/fill (Unused Fluid/FV) volume ratios for CCPD therapies for Patient A with the negative UF limits set to 40%, 30%, 25% and 20%, respectively. The average drain volume/fill volume ratio in Drain 5 of 5 decreases as the fraction of unused fluid volume increases when the negative UF limit decreases from 40% to 20%. The maximum drain/fill volume (DV/FV) ratio decreases from 1.69 to 1.45.

TABLE 1

5 × 2 Liter CCPD Therapy with Negative UF Limit Set to 40%
Patient A

| | DV/FV | | | | | | | UF/FV | | | | | | | Unused Fluid/FV | | | | | | |
|---|---|---|---|---|---|---|---|---|---|---|---|---|---|---|---|---|---|---|---|---|---|
| Day | 1 | 2 | 3 | 4 | 5 | 6 | 7 | 1 | 2 | 3 | 4 | 5 | 6 | 7 | 1 | 2 | 3 | 4 | 5 | 6 | 7 |
| 1 | 0.85 | 0.89 | 0.93 | 1.02 | 1.71 | | | −0.15 | −0.26 | −0.33 | −0.31 | 0.40 | | | 0 | 0 | 0 | 0 | 0 | | |
| 2 | 0.85 | 0.87 | 0.97 | 0.96 | 1.75 | | | −0.15 | −0.28 | −0.31 | −0.35 | 0.40 | | | 0 | 0 | 0 | 0 | 0 | | |
| 3 | 0.87 | 0.89 | 0.94 | 0.95 | 1.75 | | | −0.13 | −0.24 | −0.3 | −0.35 | 0.40 | | | 0 | 0 | 0 | 0 | 0 | | |
| 4 | 0.87 | 0.9 | 0.99 | 1.04 | 1.6 | | | −0.13 | −0.23 | −0.24 | −0.2 | 0.40 | | | 0 | 0 | 0 | 0 | 0 | | |
| 5 | 0.86 | 0.9 | 0.94 | 1.04 | 1.66 | | | −0.14 | −0.24 | −0.3 | −0.26 | 0.40 | | | 0 | 0 | 0 | 0 | 0 | | |
| 6 | 0.85 | 0.9 | 0.93 | 0.97 | 1.75 | | | −0.15 | −0.25 | −0.32 | −0.35 | 0.40 | | | 0 | 0 | 0 | 0 | 0 | | |
| 7 | 0.85 | 0.91 | 0.99 | 0.97 | 1.68 | | | −0.15 | −0.24 | −0.25 | −0.28 | 0.40 | | | 0 | 0 | 0 | 0 | 0 | | |
| 8 | 0.85 | 0.89 | 0.98 | 1.04 | 1.64 | | | −0.15 | −0.26 | −0.28 | −0.24 | 0.40 | | | 0 | 0 | 0 | 0 | 0 | | |
| 9 | 0.86 | 0.87 | 0.98 | 1.05 | 1.64 | | | −0.14 | −0.27 | −0.29 | −0.24 | 0.40 | | | 0 | 0 | 0 | 0 | 0 | | |
| 10 | 0.85 | 0.87 | 0.94 | 0.95 | 1.79 | | | −0.15 | −0.28 | −0.34 | −0.39 | 0.40 | | | 0 | 0 | 0 | 0 | 0 | | |
| 11 | 0.87 | 0.87 | 0.95 | 0.98 | 1.73 | | | −0.13 | −0.26 | −0.31 | −0.33 | 0.40 | | | 0 | 0 | 0 | 0 | 0 | | |
| 12 | 0.85 | 0.89 | 0.97 | 1 | 1.69 | | | −0.15 | −0.26 | −0.29 | −0.29 | 0.40 | | | 0 | 0 | 0 | 0 | 0 | | |
| 13 | 0.85 | 0.89 | 0.98 | 1.04 | 1.64 | | | −0.15 | −0.26 | −0.28 | −0.24 | 0.40 | | | 0 | 0 | 0 | 0 | 0 | | |
| 14 | 0.87 | 0.89 | 0.99 | 1.02 | 1.63 | | | −0.13 | −0.24 | −0.25 | −0.23 | 0.40 | | | 0 | 0 | 0 | 0 | 0 | | |
| 15 | 0.87 | 0.87 | 0.95 | 0.99 | 1.72 | | | −0.13 | −0.26 | −0.31 | −0.32 | 0.40 | | | 0 | 0 | 0 | 0 | 0 | | |
| 16 | 0.87 | 0.88 | 0.94 | 1.05 | 1.66 | | | −0.13 | −0.25 | −0.31 | −0.26 | 0.40 | | | 0 | 0 | 0 | 0 | 0 | | |
| 17 | 0.85 | 0.9 | 0.95 | 1.04 | 1.66 | | | −0.15 | −0.25 | −0.3 | −0.26 | 0.40 | | | 0 | 0 | 0 | 0 | 0 | | |
| 18 | 0.85 | 0.88 | 0.94 | 1 | 1.73 | | | −0.15 | −0.27 | −0.33 | −0.33 | 0.40 | | | 0 | 0 | 0 | 0 | 0 | | |
| 19 | 0.87 | 0.91 | 0.92 | 1.02 | 1.68 | | | −0.13 | −0.22 | −0.3 | −0.28 | 0.40 | | | 0 | 0 | 0 | 0 | 0 | | |
| 20 | 0.86 | 0.9 | 0.93 | 0.99 | 1.72 | | | −0.14 | −0.24 | −0.31 | −0.32 | 0.40 | | | 0 | 0 | 0 | 0 | 0 | | |
| AVE | 0.86 | 0.89 | 0.96 | 1.01 | 1.69 | | | −0.14 | −0.25 | −0.30 | −0.29 | 0.40 | | | 0.00 | 0.00 | 0.00 | 0.00 | 0.00 | | |

TABLE 2

5 × 2 Liter CCPD Therapy with Negative UF Limit Set to 30%
Patient A

| | DV/FV | | | | | | | UF/FV | | | | | | | Unused Fluid/FV | | | | | | |
|---|---|---|---|---|---|---|---|---|---|---|---|---|---|---|---|---|---|---|---|---|---|
| Day | 1 | 2 | 3 | 4 | 5 | 6 | 7 | 1 | 2 | 3 | 4 | 5 | 6 | 7 | 1 | 2 | 3 | 4 | 5 | 6 | 7 |
| 1 | 0.86 | 0.88 | 0.96 | 1 | 1.7 | | | −0.14 | −0.26 | −0.3 | −0.3 | 0.40 | | | 0 | 0 | 0 | 0 | 0 | | |
| 2 | 0.85 | 0.91 | 0.96 | 0.95 | 1.7 | | | −0.15 | −0.24 | −0.28 | −0.33 | 0.37 | | | 0 | 0 | 0 | −0.03 | −0.03 | | |
| 3 | 0.87 | 0.89 | 0.93 | 0.98 | 1.69 | | | −0.13 | −0.24 | −0.31 | −0.33 | 0.36 | | | 0 | 0 | −0.01 | −0.04 | −0.04 | | |
| 4 | 0.86 | 0.91 | 0.93 | 1.02 | 1.68 | | | −0.14 | −0.23 | −0.3 | −0.28 | 0.40 | | | 0 | 0 | 0 | 0 | 0 | | |
| 5 | 0.85 | 0.87 | 0.92 | 0.98 | 1.64 | | | −0.15 | −0.28 | −0.36 | −0.38 | 0.26 | | | 0 | 0 | −0.06 | −0.14 | −0.14 | | |
| 6 | 0.86 | 0.89 | 0.92 | 1.01 | 1.67 | | | −0.14 | −0.25 | −0.33 | −0.32 | 0.35 | | | 0 | 0 | −0.03 | −0.05 | −0.05 | | |
| 7 | 0.85 | 0.9 | 0.98 | 1 | 1.67 | | | −0.15 | −0.25 | −0.27 | −0.27 | 0.40 | | | 0 | 0 | 0 | 0 | 0 | | |
| 8 | 0.86 | 0.9 | 0.95 | 1.05 | 1.64 | | | −0.14 | −0.24 | −0.29 | −0.24 | 0.40 | | | 0 | 0 | 0 | 0 | 0 | | |
| 9 | 0.87 | 0.88 | 0.92 | 1.04 | 1.66 | | | −0.13 | −0.25 | −0.33 | −0.29 | 0.37 | | | 0 | 0 | −0.03 | −0.03 | −0.03 | | |
| 10 | 0.85 | 0.91 | 0.95 | 1.04 | 1.65 | | | −0.15 | −0.24 | −0.29 | −0.25 | 0.40 | | | 0 | 0 | 0 | 0 | 0 | | |
| 11 | 0.85 | 0.9 | 0.99 | 1.02 | 1.64 | | | −0.15 | −0.25 | −0.26 | −0.24 | 0.40 | | | 0 | 0 | 0 | 0 | 0 | | |
| 12 | 0.85 | 0.87 | 0.91 | 0.97 | 1.63 | | | −0.15 | −0.28 | −0.37 | −0.4 | 0.23 | | | 0 | 0 | −0.07 | −0.17 | −0.17 | | |
| 13 | 0.87 | 0.89 | 0.93 | 0.99 | 1.69 | | | −0.13 | −0.24 | −0.31 | −0.32 | 0.37 | | | 0 | 0 | −0.01 | −0.03 | −0.03 | | |
| 14 | 0.87 | 0.89 | 0.95 | 0.95 | 1.7 | | | −0.13 | −0.24 | −0.29 | −0.34 | 0.36 | | | 0 | 0 | 0 | −0.04 | −0.04 | | |
| 15 | 0.86 | 0.9 | 0.96 | 0.98 | 1.7 | | | −0.14 | −0.24 | −0.28 | −0.3 | 0.40 | | | 0 | 0 | 0 | 0 | 0 | | |
| 16 | 0.85 | 0.87 | 0.93 | 0.96 | 1.65 | | | −0.15 | −0.28 | −0.35 | −0.39 | 0.26 | | | 0 | 0 | −0.05 | −0.14 | −0.14 | | |
| 17 | 0.85 | 0.91 | 0.97 | 1.03 | 1.64 | | | −0.15 | −0.24 | −0.27 | −0.24 | 0.40 | | | 0 | 0 | 0 | 0 | 0 | | |
| 18 | 0.86 | 0.91 | 0.91 | 1.04 | 1.66 | | | −0.14 | −0.23 | −0.32 | −0.28 | 0.38 | | | 0 | 0 | −0.02 | −0.02 | −0.02 | | |
| 19 | 0.87 | 0.91 | 0.95 | 1.01 | 1.66 | | | −0.13 | −0.22 | −0.27 | −0.26 | 0.40 | | | 0 | 0 | 0 | 0 | 0 | | |
| 20 | 0.87 | 0.89 | 0.99 | 0.99 | 1.66 | | | −0.13 | −0.24 | −0.25 | −0.26 | 0.40 | | | 0 | 0 | 0 | 0 | 0 | | |
| AVE | 0.86 | 0.89 | 0.95 | 1.00 | 1.67 | | | −0.14 | −0.25 | −0.30 | −0.30 | 0.37 | | | 0.00 | 0.00 | −0.01 | −0.03 | −0.03 | | |

TABLE 3

5 × 2 Liter CCPD Therapy with Negative UF Limit Set to 25%
Patient A

| | DV/FV | | | | | | | UF/FV | | | | | | | Unused Fluid/FV | | | | | | |
|---|---|---|---|---|---|---|---|---|---|---|---|---|---|---|---|---|---|---|---|---|---|
| Day | 1 | 2 | 3 | 4 | 5 | 6 | 7 | 1 | 2 | 3 | 4 | 5 | 6 | 7 | 1 | 2 | 3 | 4 | 5 | 6 | 7 |
| 1 | 0.87 | 0.9 | 0.95 | 0.95 | 1.62 | | | −0.13 | −0.23 | −0.28 | −0.33 | 0.29 | | | 0 | 0 | −0.03 | −0.11 | −0.11 | | |
| 2 | 0.87 | 0.89 | 0.92 | 1.04 | 1.58 | | | −0.13 | −0.24 | −0.32 | −0.28 | 0.30 | | | 0 | 0 | −0.07 | −0.1 | −0.1 | | |
| 3 | 0.86 | 0.91 | 0.91 | 1 | 1.58 | | | −0.14 | −0.23 | −0.32 | −0.32 | 0.26 | | | 0 | 0 | −0.07 | −0.14 | −0.14 | | |
| 4 | 0.86 | 0.89 | 0.93 | 0.98 | 1.58 | | | −0.14 | −0.25 | −0.32 | −0.34 | 0.24 | | | 0 | 0 | −0.07 | −0.16 | −0.16 | | |
| 5 | 0.86 | 0.88 | 0.95 | 1.05 | 1.58 | | | −0.14 | −0.26 | −0.31 | −0.26 | 0.32 | | | 0 | −0.01 | −0.07 | −0.08 | −0.08 | | |
| 6 | 0.86 | 0.91 | 0.91 | 1.02 | 1.58 | | | −0.14 | −0.23 | −0.32 | −0.3 | 0.28 | | | 0 | 0 | −0.07 | −0.12 | −0.12 | | |

TABLE 3-continued

5 × 2 Liter CCPD Therapy with Negative UF Limit Set to 25%
Patient A

| Day | DV/FV | | | | | | | UF/FV | | | | | | | Unused Fluid/FV | | | | | | |
|---|---|---|---|---|---|---|---|---|---|---|---|---|---|---|---|---|---|---|---|---|---|
| | 1 | 2 | 3 | 4 | 5 | 6 | 7 | 1 | 2 | 3 | 4 | 5 | 6 | 7 | 1 | 2 | 3 | 4 | 5 | 6 | 7 |
| 7 | 0.87 | 0.89 | 0.93 | 0.99 | 1.59 | | | −0.13 | −0.24 | −0.31 | −0.32 | 0.27 | | | 0 | 0 | −0.06 | −0.13 | −0.13 | | |
| 8 | 0.85 | 0.89 | 0.99 | 0.95 | 1.62 | | | −0.15 | −0.26 | −0.27 | −0.32 | 0.30 | | | 0 | −0.01 | −0.03 | −0.1 | −0.1 | | |
| 9 | 0.87 | 0.89 | 0.99 | 1.02 | 1.63 | | | −0.13 | −0.24 | −0.25 | −0.23 | 0.40 | | | 0 | 0 | 0 | 0 | 0 | | |
| 10 | 0.86 | 0.89 | 0.98 | 0.97 | 1.63 | | | −0.14 | −0.25 | −0.27 | −0.3 | 0.33 | | | 0 | 0 | −0.02 | −0.07 | −0.07 | | |
| 11 | 0.86 | 0.91 | 0.96 | 0.98 | 1.63 | | | −0.14 | −0.23 | −0.27 | −0.29 | 0.34 | | | 0 | 0 | −0.02 | −0.06 | −0.06 | | |
| 12 | 0.85 | 0.89 | 0.95 | 1.01 | 1.58 | | | −0.15 | −0.26 | −0.31 | −0.3 | 0.28 | | | 0 | −0.01 | −0.07 | −0.12 | −0.12 | | |
| 13 | 0.87 | 0.87 | 0.99 | 0.99 | 1.62 | | | −0.13 | −0.26 | −0.27 | −0.28 | 0.34 | | | 0 | −0.01 | −0.03 | −0.06 | −0.06 | | |
| 14 | 0.85 | 0.87 | 0.99 | 1.04 | 1.58 | | | −0.15 | −0.28 | −0.29 | −0.25 | 0.33 | | | 0 | −0.03 | −0.07 | −0.07 | −0.07 | | |
| 15 | 0.87 | 0.89 | 0.94 | 1.03 | 1.6 | | | −0.13 | −0.24 | −0.3 | −0.27 | 0.33 | | | 0 | 0 | −0.05 | −0.07 | −0.07 | | |
| 16 | 0.85 | 0.87 | 0.96 | 1.02 | 1.55 | | | −0.15 | −0.28 | −0.32 | −0.3 | 0.25 | | | 0 | −0.03 | −0.1 | −0.15 | −0.15 | | |
| 17 | 0.85 | 0.89 | 0.98 | 0.99 | 1.61 | | | −0.15 | −0.26 | −0.28 | −0.29 | 0.32 | | | 0 | −0.01 | −0.04 | −0.08 | −0.08 | | |
| 18 | 0.86 | 0.91 | 0.97 | 0.96 | 1.64 | | | −0.14 | −0.23 | −0.26 | −0.3 | 0.34 | | | 0 | 0 | −0.01 | −0.06 | −0.06 | | |
| 19 | 0.87 | 0.89 | 0.92 | 1.04 | 1.58 | | | −0.13 | −0.24 | −0.32 | −0.28 | 0.30 | | | 0 | 0 | −0.07 | −0.1 | −0.1 | | |
| 20 | 0.86 | 0.88 | 0.97 | 0.95 | 1.6 | | | −0.14 | −0.26 | −0.29 | −0.34 | 0.26 | | | 0 | −0.01 | −0.05 | −0.14 | −0.14 | | |
| AVE | 0.86 | 0.89 | 0.95 | 1.00 | 1.60 | | | −0.14 | −0.25 | −0.29 | −0.30 | 0.30 | | | 0.00 | −0.01 | −0.05 | −0.10 | −0.1 | | |

TABLE 4

5 × 2 Liter CCPD Therapy with Negative UF Limit Set to 20%
Patient A

| Day | DV/FV | | | | | | | UF/FV | | | | | | | Unused Fluid/FV | | | | | | |
|---|---|---|---|---|---|---|---|---|---|---|---|---|---|---|---|---|---|---|---|---|---|
| | 1 | 2 | 3 | 4 | 5 | 6 | 7 | 1 | 2 | 3 | 4 | 5 | 6 | 7 | 1 | 2 | 3 | 4 | 5 | 6 | 7 |
| 1 | 0.86 | 0.9 | 0.96 | 0.95 | 1.48 | | | −0.14 | −0.24 | −0.28 | −0.33 | 0.15 | | | 0 | −0.04 | −0.12 | −0.25 | −0.25 | | |
| 2 | 0.87 | 0.87 | 0.93 | 0.98 | 1.41 | | | −0.13 | −0.26 | −0.33 | −0.35 | 0.06 | | | 0 | −0.06 | −0.19 | −0.34 | −0.34 | | |
| 3 | 0.85 | 0.89 | 0.97 | 1 | 1.45 | | | −0.15 | −0.26 | −0.29 | −0.29 | 0.16 | | | 0 | −0.06 | −0.15 | −0.24 | −0.24 | | |
| 4 | 0.87 | 0.89 | 0.94 | 1.02 | 1.46 | | | −0.13 | −0.24 | −0.3 | −0.28 | 0.18 | | | 0 | −0.04 | −0.14 | −0.22 | −0.22 | | |
| 5 | 0.85 | 0.91 | 0.99 | 1 | 1.51 | | | −0.15 | −0.24 | −0.25 | −0.25 | 0.26 | | | 0 | −0.04 | −0.09 | −0.14 | −0.14 | | |
| 6 | 0.87 | 0.89 | 0.96 | 0.95 | 1.48 | | | −0.13 | −0.24 | −0.28 | −0.33 | 0.15 | | | 0 | −0.04 | −0.12 | −0.25 | −0.25 | | |
| 7 | 0.85 | 0.89 | 0.96 | 0.96 | 1.44 | | | −0.15 | −0.26 | −0.3 | −0.34 | 0.10 | | | 0 | −0.06 | −0.16 | −0.3 | −0.3 | | |
| 8 | 0.86 | 0.88 | 0.96 | 1.05 | 1.44 | | | −0.14 | −0.26 | −0.3 | −0.25 | 0.19 | | | 0 | −0.06 | −0.16 | −0.21 | −0.21 | | |
| 9 | 0.85 | 0.88 | 0.96 | 1.04 | 1.42 | | | −0.15 | −0.27 | −0.31 | −0.27 | 0.15 | | | 0 | −0.07 | −0.18 | −0.25 | −0.25 | | |
| 10 | 0.86 | 0.91 | 0.92 | 1 | 1.46 | | | −0.14 | −0.23 | −0.31 | −0.31 | 0.15 | | | 0 | −0.03 | −0.14 | −0.25 | −0.25 | | |
| 11 | 0.86 | 0.87 | 0.95 | 0.97 | 1.41 | | | −0.14 | −0.27 | −0.32 | −0.35 | 0.06 | | | 0 | −0.07 | −0.19 | −0.34 | −0.34 | | |
| 12 | 0.87 | 0.9 | 0.91 | 1.05 | 1.45 | | | −0.13 | −0.23 | −0.32 | −0.27 | 0.18 | | | 0 | −0.03 | −0.15 | −0.22 | −0.22 | | |
| 13 | 0.85 | 0.88 | 0.96 | 0.96 | 1.42 | | | −0.15 | −0.27 | −0.31 | −0.35 | 0.07 | | | 0 | −0.07 | −0.18 | −0.33 | −0.33 | | |
| 14 | 0.87 | 0.89 | 0.93 | 1.03 | 1.45 | | | −0.13 | −0.24 | −0.31 | −0.28 | 0.17 | | | 0 | −0.04 | −0.15 | −0.23 | −0.23 | | |
| 15 | 0.87 | 0.88 | 0.98 | 0.96 | 1.48 | | | −0.13 | −0.25 | −0.27 | −0.31 | 0.17 | | | 0 | −0.05 | −0.12 | −0.23 | −0.23 | | |
| 16 | 0.85 | 0.87 | 0.94 | 0.98 | 1.38 | | | −0.15 | −0.28 | −0.34 | −0.36 | 0.02 | | | 0 | −0.08 | −0.22 | −0.38 | −0.38 | | |
| 17 | 0.87 | 0.91 | 0.91 | 0.99 | 1.47 | | | −0.13 | −0.27 | −0.31 | −0.32 | 0.15 | | | 0 | −0.02 | −0.13 | −0.25 | −0.25 | | |
| 18 | 0.87 | 0.91 | 0.94 | 1.04 | 1.5 | | | −0.13 | −0.22 | −0.28 | −0.24 | 0.26 | | | 0 | −0.02 | −0.1 | −0.14 | −0.14 | | |
| 19 | 0.85 | 0.9 | 0.92 | 1.02 | 1.42 | | | −0.15 | −0.25 | −0.33 | −0.31 | 0.11 | | | 0 | −0.05 | −0.18 | −0.29 | −0.29 | | |
| 20 | 0.86 | 0.91 | 0.96 | 1.03 | 1.5 | | | −0.14 | −0.23 | −0.27 | −0.24 | 0.26 | | | 0 | −0.03 | −0.1 | −0.14 | −0.14 | | |
| AVE | 0.86 | 0.89 | 0.95 | 1.00 | 1.45 | | | −0.14 | −0.25 | −0.30 | −0.30 | 0.15 | | | 0.00 | −0.05 | −0.15 | −0.25 | −0.25 | | |

Example for Patient B: Tables 5, 6, 7 and 8 contain system 10 drain volume/fill volume ratios, UF/fill volume ratios and unused fluid volume/fill volume ratios for CCPD therapies for Patient B with the negative UF limits set to 40%, 30%, 25% and 20%, respectively. The average drain volume/fill volume (DV/FV) ratio in Drain 5 of 5 decreases as the fraction of unused fluid volume increases when the negative UF Limit decreases from 40% to 20%. The maximum DV/FV ratio decreases from 1.67 to 1.43, as seen in FIG. 5-8.

TABLE 5

5 × 2 Liter CCPD Therapy with Negative UF Limit Set to 40%
Patient B

| Day | DV/FV | | | | | | | UF/FV | | | | | | | Unused Fluid/FV | | | | | | |
|---|---|---|---|---|---|---|---|---|---|---|---|---|---|---|---|---|---|---|---|---|---|
| | 1 | 2 | 3 | 4 | 5 | 6 | 7 | 1 | 2 | 3 | 4 | 5 | 6 | 7 | 1 | 2 | 3 | 4 | 5 | 6 | 7 |
| 1 | 0.87 | 0.89 | 0.96 | 1.14 | 1.54 | | | −0.13 | −0.24 | −0.28 | −0.14 | 0.40 | | | 0 | 0 | 0 | 0 | 0 | | |
| 2 | 0.86 | 0.93 | 1.05 | 1.03 | 1.53 | | | −0.14 | −0.21 | −0.16 | −0.13 | 0.40 | | | 0 | 0 | 0 | 0 | 0 | | |
| 3 | 0.87 | 0.87 | 0.85 | 0.98 | 1.79 | | | −0.13 | −0.26 | −0.41 | −0.43 | 0.36 | | | 0 | 0 | −0.01 | −0.04 | −0.04 | | |
| 4 | 0.87 | 0.9 | 0.87 | 1.03 | 1.73 | | | −0.13 | −0.23 | −0.36 | −0.33 | 0.40 | | | 0 | 0 | 0 | 0 | 0 | | |
| 5 | 0.85 | 0.86 | 1.05 | 0.94 | 1.7 | | | −0.15 | −0.29 | −0.24 | −0.3 | 0.40 | | | 0 | 0 | 0 | 0 | 0 | | |

TABLE 5-continued

5 × 2 Liter CCPD Therapy with Negative UF Limit Set to 40%
Patient B

| | DV/FV | | | | | | | UF/FV | | | | | | | Unused Fluid/FV | | | | | | |
|---|---|---|---|---|---|---|---|---|---|---|---|---|---|---|---|---|---|---|---|---|---|
| Day | 1 | 2 | 3 | 4 | 5 | 6 | 7 | 1 | 2 | 3 | 4 | 5 | 6 | 7 | 1 | 2 | 3 | 4 | 5 | 6 | 7 |
| 6 | 0.85 | 0.89 | 0.99 | 1.09 | 1.58 | | | −0.15 | −0.26 | −0.27 | −0.18 | 0.40 | | | 0 | 0 | 0 | 0 | 0 | | |
| 7 | 0.85 | 0.87 | 0.98 | 0.91 | 1.79 | | | −0.15 | −0.28 | −0.3 | −0.39 | 0.40 | | | 0 | 0 | 0 | 0 | 0 | | |
| 8 | 0.85 | 0.93 | 0.88 | 0.89 | 1.8 | | | −0.15 | −0.22 | −0.34 | −0.45 | 0.35 | | | 0 | 0 | 0 | −0.05 | −0.05 | | |
| 9 | 0.86 | 0.89 | 0.95 | 1.15 | 1.55 | | | −0.14 | −0.25 | −0.3 | −0.15 | 0.40 | | | 0 | 0 | 0 | 0 | 0 | | |
| 10 | 0.85 | 0.87 | 0.87 | 0.94 | 1.79 | | | −0.15 | −0.28 | −0.41 | −0.47 | 0.32 | | | 0 | 0 | −0.01 | −0.08 | −0.08 | | |
| 11 | 0.86 | 0.91 | 0.85 | 1 | 1.78 | | | −0.14 | −0.23 | −0.38 | −0.38 | 0.40 | | | 0 | 0 | 0 | 0 | 0 | | |
| 12 | 0.86 | 0.89 | 1.03 | 1 | 1.62 | | | −0.14 | −0.25 | −0.22 | −0.22 | 0.40 | | | 0 | 0 | 0 | 0 | 0 | | |
| 13 | 0.85 | 0.87 | 1.03 | 0.96 | 1.69 | | | −0.15 | −0.28 | −0.25 | −0.29 | 0.40 | | | 0 | 0 | 0 | 0 | 0 | | |
| 14 | 0.86 | 0.93 | 1.04 | 1.05 | 1.52 | | | −0.14 | −0.21 | −0.17 | −0.12 | 0.40 | | | 0 | 0 | 0 | 0 | 0 | | |
| 15 | 0.87 | 0.91 | 1.01 | 0.94 | 1.67 | | | −0.13 | −0.22 | −0.21 | −0.27 | 0.40 | | | 0 | 0 | 0 | 0 | 0 | | |
| 16 | 0.87 | 0.9 | 0.93 | 0.87 | 1.8 | | | −0.13 | −0.23 | −0.3 | −0.43 | 0.37 | | | 0 | 0 | 0 | −0.03 | −0.03 | | |
| 17 | 0.87 | 0.85 | 0.86 | 1.15 | 1.65 | | | −0.13 | −0.28 | −0.42 | −0.27 | 0.38 | | | 0 | 0 | −0.02 | −0.02 | −0.02 | | |
| 18 | 0.85 | 0.88 | 1.04 | 1.07 | 1.56 | | | −0.15 | −0.27 | −0.23 | −0.16 | 0.40 | | | 0 | 0 | 0 | 0 | 0 | | |
| 19 | 0.87 | 0.92 | 0.91 | 1.09 | 1.61 | | | −0.13 | −0.21 | −0.3 | −0.21 | 0.40 | | | 0 | 0 | 0 | 0 | 0 | | |
| 20 | 0.87 | 0.89 | 1.04 | 1 | 1.6 | | | −0.13 | −0.24 | −0.2 | −0.2 | 0.40 | | | 0 | 0 | 0 | 0 | 0 | | |
| AVE | 0.86 | 0.89 | 0.96 | 1.01 | 1.67 | | | −0.14 | −0.25 | −0.29 | −0.28 | 0.39 | | | 0.00 | 0.00 | 0.00 | −0.01 | −0.01 | | |

TABLE 6

5 × 2 Liter CCPD Therapy with Negative UF Limit Set to 30%
Patient B

| | DV/FV | | | | | | | UF/FV | | | | | | | Unused Fluid/FV | | | | | | |
|---|---|---|---|---|---|---|---|---|---|---|---|---|---|---|---|---|---|---|---|---|---|
| Day | 1 | 2 | 3 | 4 | 5 | 6 | 7 | 1 | 2 | 3 | 4 | 5 | 6 | 7 | 1 | 2 | 3 | 4 | 5 | 6 | 7 |
| 1 | 0.87 | 0.93 | 0.94 | 0.98 | 1.68 | | | −0.13 | −0.2 | −0.26 | −0.28 | 0.40 | | | 0 | 0 | 0 | 0 | 0 | | |
| 2 | 0.87 | 0.85 | 0.92 | 1.08 | 1.62 | | | −0.13 | −0.28 | −0.36 | −0.28 | 0.34 | | | 0 | 0 | −0.06 | −0.06 | −0.06 | | |
| 3 | 0.85 | 0.93 | 1.05 | 1.08 | 1.49 | | | −0.15 | −0.22 | −0.17 | −0.09 | 0.40 | | | 0 | 0 | 0 | 0 | 0 | | |
| 4 | 0.87 | 0.9 | 0.91 | 1.1 | 1.6 | | | −0.13 | −0.23 | −0.32 | −0.22 | 0.38 | | | 0 | 0 | −0.02 | −0.02 | −0.02 | | |
| 5 | 0.86 | 0.91 | 0.95 | 0.93 | 1.7 | | | −0.14 | −0.23 | −0.28 | −0.35 | 0.35 | | | 0 | 0 | 0 | −0.05 | −0.05 | | |
| 6 | 0.87 | 0.85 | 1.03 | 0.9 | 1.7 | | | −0.13 | −0.28 | −0.25 | −0.35 | 0.35 | | | 0 | 0 | 0 | −0.05 | −0.05 | | |
| 7 | 0.86 | 0.91 | 0.93 | 0.92 | 1.7 | | | −0.14 | −0.23 | −0.3 | −0.38 | 0.32 | | | 0 | 0 | 0 | −0.08 | −0.08 | | |
| 8 | 0.87 | 0.88 | 0.99 | 0.12 | 1.54 | | | −0.13 | −0.25 | −0.26 | −0.14 | 0.40 | | | 0 | 0 | 0 | 0 | 0 | | |
| 9 | 0.87 | 0.89 | 0.91 | 1.06 | 1.64 | | | −0.13 | −0.24 | −0.33 | −0.27 | 0.37 | | | 0 | 0 | −0.03 | −0.03 | −0.03 | | |
| 10 | 0.86 | 0.85 | 1.05 | 1.13 | 1.51 | | | −0.14 | −0.29 | −0.24 | −0.11 | 0.40 | | | 0 | 0 | 0 | 0 | 0 | | |
| 11 | 0.85 | 0.9 | 0.91 | 1.1 | 1.6 | | | −0.15 | −0.25 | −0.34 | −0.24 | 0.36 | | | 0 | 0 | −0.04 | −0.04 | −0.04 | | |
| 12 | 0.86 | 0.91 | 1.02 | 1.11 | 1.5 | | | −0.14 | −0.23 | −0.21 | −0.1 | 0.40 | | | 0 | 0 | 0 | 0 | 0 | | |
| 13 | 0.85 | 0.85 | 1.05 | 1.14 | 1.51 | | | −0.15 | −0.3 | −0.25 | −0.11 | 0.40 | | | 0 | 0 | 0 | 0 | 0 | | |
| 14 | 0.85 | 0.9 | 1.05 | 1 | 1.6 | | | −0.15 | −0.25 | −0.2 | −0.2 | 0.40 | | | 0 | 0 | 0 | 0 | 0 | | |
| 15 | 0.86 | 0.93 | 0.87 | 0.97 | 1.66 | | | −0.14 | −0.21 | −0.34 | −0.37 | 0.29 | | | 0 | 0 | −0.04 | −0.11 | −0.11 | | |
| 16 | 0.85 | 0.85 | 0.97 | 1.15 | 1.55 | | | −0.15 | −0.3 | −0.33 | −0.18 | 0.37 | | | 0 | 0 | −0.03 | −0.03 | −0.03 | | |
| 17 | 0.87 | 0.87 | 0.92 | 0.95 | 1.66 | | | −0.13 | −0.26 | −0.34 | −0.39 | 0.27 | | | 0 | 0 | −0.04 | −0.13 | −0.13 | | |
| 18 | 0.87 | 0.93 | 0.94 | 1.05 | 1.61 | | | −0.13 | −0.2 | −0.26 | −0.21 | 0.40 | | | 0 | 0 | 0 | 0 | 0 | | |
| 19 | 0.85 | 0.93 | 0.85 | 1.01 | 1.63 | | | −0.15 | −0.22 | −0.37 | −0.36 | 0.27 | | | 0 | 0 | −0.07 | −0.13 | −0.13 | | |
| 20 | 0.87 | 0.9 | 1.05 | 1.05 | 1.53 | | | −0.13 | −0.23 | −0.18 | −0.13 | 0.40 | | | 0 | 0 | 0 | 0 | 0 | | |
| AVE | 0.86 | 0.89 | 0.97 | 1.04 | 1.60 | | | −0.14 | −0.25 | −0.28 | −0.24 | 0.36 | | | 0.00 | 0.00 | −0.02 | −0.04 | −0.04 | | |

TABLE 7

5 × 2 Liter CCPD Therapy with Negative UF Limit Set to 25%
Patient B

| | DV/FV | | | | | | | UF/FV | | | | | | | Unused Fluid/FV | | | | | | |
|---|---|---|---|---|---|---|---|---|---|---|---|---|---|---|---|---|---|---|---|---|---|
| Day | 1 | 2 | 3 | 4 | 5 | 6 | 7 | 1 | 2 | 3 | 4 | 5 | 6 | 7 | 1 | 2 | 3 | 4 | 5 | 6 | 7 |
| 1 | 0.87 | 0.93 | 1.03 | 0.97 | 1.6 | | | −0.13 | −0.2 | −0.17 | −0.2 | 0.40 | | | 0 | 0 | 0 | 0 | 0 | | |
| 2 | 0.86 | 0.88 | 1 | 1.1 | 1.54 | | | −0.14 | −0.26 | −0.26 | −0.16 | 0.38 | | | 0 | −0.01 | −0.02 | −0.02 | −0.02 | | |
| 3 | 0.87 | 0.89 | 0.91 | 1.1 | 1.55 | | | −0.13 | −0.24 | −0.33 | −0.23 | 0.32 | | | 0 | 0 | −0.08 | −0.08 | −0.08 | | |
| 4 | 0.87 | 0.93 | 0.97 | 0.87 | 1.65 | | | −0.13 | −0.2 | −0.23 | −0.36 | 0.29 | | | 0 | 0 | 0 | −0.11 | −0.11 | | |
| 5 | 0.86 | 0.89 | 1 | 1.01 | 1.64 | | | −0.14 | −0.25 | −0.25 | −0.24 | 0.40 | | | 0 | 0 | 0 | 0 | 0 | | |
| 6 | 0.87 | 0.92 | 0.88 | 0.88 | 1.57 | | | −0.13 | −0.21 | −0.33 | −0.45 | 0.12 | | | 0 | 0 | −0.08 | −0.28 | −0.28 | | |
| 7 | 0.86 | 0.87 | 0.93 | 0.94 | 1.54 | | | −0.14 | −0.27 | −0.34 | −0.4 | 0.14 | | | 0 | −0.02 | −0.11 | −0.26 | −0.26 | | |
| 8 | 0.86 | 0.93 | 0.89 | 1.09 | 1.56 | | | −0.14 | −0.21 | −0.32 | −0.23 | 0.33 | | | 0 | 0 | −0.07 | −0.07 | −0.07 | | |
| 9 | 0.87 | 0.87 | 0.91 | 0.89 | 1.54 | | | −0.13 | −0.26 | −0.35 | −0.46 | 0.08 | | | 0 | −0.01 | −0.11 | −0.32 | −0.32 | | |
| 10 | 0.85 | 0.85 | 1.04 | 0.94 | 1.59 | | | −0.15 | −0.3 | −0.26 | −0.32 | 0.27 | | | 0 | −0.05 | −0.06 | −0.13 | −0.13 | | |
| 11 | 0.85 | 0.86 | 0.91 | 1.14 | 1.47 | | | −0.15 | −0.29 | −0.38 | −0.24 | 0.23 | | | 0 | −0.04 | −0.17 | −0.17 | −0.17 | | |

TABLE 7-continued

5 × 2 Liter CCPD Therapy with Negative UF Limit Set to 25%
Patient B

| Day | DV/FV | | | | | | | UF/FV | | | | | | | Unused Fluid/FV | | | | | | |
| --- | --- | --- | --- | --- | --- | --- | --- | --- | --- | --- | --- | --- | --- | --- | --- | --- | --- | --- | --- | --- | --- |
|  | 1 | 2 | 3 | 4 | 5 | 6 | 7 | 1 | 2 | 3 | 4 | 5 | 6 | 7 | 1 | 2 | 3 | 4 | 5 | 6 | 7 |
| 12 | 0.87 | 0.86 | 0.88 | 0.87 | 1.49 | | | −0.13 | −0.27 | −0.39 | −0.52 | −0.03 | | | 0 | −0.02 | −0.16 | −0.43 | −0.43 | | |
| 13 | 0.86 | 0.9 | 0.94 | 1.06 | 1.59 | | | −0.14 | −0.24 | −0.3 | −0.24 | 0.35 | | | 0 | 0 | −0.05 | −0.05 | −0.05 | | |
| 14 | 0.85 | 0.92 | 0.87 | 1.14 | 1.51 | | | −0.15 | −0.23 | −0.36 | −0.22 | 0.29 | | | 0 | 0 | −0.11 | −0.11 | −0.11 | | |
| 15 | 0.87 | 0.88 | 0.87 | 0.98 | 1.52 | | | −0.13 | −0.25 | −0.38 | −0.4 | 0.12 | | | 0 | 0 | −0.13 | −0.28 | −0.28 | | |
| 16 | 0.87 | 0.92 | 0.91 | 0.9 | 1.6 | | | −0.13 | −0.21 | −0.3 | −0.4 | 0.20 | | | 0 | 0 | −0.05 | −0.2 | −0.2 | | |
| 17 | 0.87 | 0.86 | 1.04 | 1.14 | 1.47 | | | −0.13 | −0.27 | −0.23 | −0.09 | 0.38 | | | 0 | −0.02 | −0.02 | −0.02 | −0.02 | | |
| 18 | 0.86 | 0.89 | 0.98 | 1.04 | 1.61 | | | −0.14 | −0.25 | −0.27 | −0.23 | 0.38 | | | 0 | 0 | −0.02 | −0.02 | −0.02 | | |
| 19 | 0.85 | 0.85 | 0.88 | 1.1 | 1.43 | | | −0.15 | −0.3 | −0.42 | −0.32 | 0.11 | | | 0 | −0.05 | −0.22 | −0.29 | −0.29 | | |
| 20 | 0.87 | 0.85 | 1.05 | 1.07 | 1.53 | | | −0.13 | −0.28 | −0.23 | −0.16 | 0.37 | | | 0 | −0.03 | −0.03 | −0.03 | −0.03 | | |
| AVE | 0.86 | 0.89 | 0.94 | 1.01 | 1.55 | | | −0.14 | −0.25 | −0.31 | −0.29 | 0.26 | | | 0.00 | −0.01 | −0.07 | −0.14 | −0.14 | | |

TABLE 8

5 × 2 Liter CCPD Therapy with Negative UF Limit Set to 20%
Patient B

| Day | DV/FV | | | | | | | UF/FV | | | | | | | Unused Fluid/FV | | | | | | |
| --- | --- | --- | --- | --- | --- | --- | --- | --- | --- | --- | --- | --- | --- | --- | --- | --- | --- | --- | --- | --- | --- |
|  | 1 | 2 | 3 | 4 | 5 | 6 | 7 | 1 | 2 | 3 | 4 | 5 | 6 | 7 | 1 | 2 | 3 | 4 | 5 | 6 | 7 |
| 1 | 0.85 | 0.85 | 0.92 | 0.97 | 1.32 | | | −0.15 | −0.3 | −0.38 | −0.41 | −0.09 | | | 0 | −0.1 | −0.28 | −0.49 | −0.49 | | |
| 2 | 0.85 | 0.89 | 1.03 | 0.93 | 1.51 | | | −0.15 | −0.26 | −0.23 | −0.3 | 0.21 | | | 0 | −0.06 | −0.09 | −0.19 | −0.19 | | |
| 3 | 0.87 | 0.91 | 0.92 | 1.1 | 1.48 | | | −0.13 | −0.22 | −0.3 | −0.2 | 0.28 | | | 0 | −0.02 | −0.12 | −0.12 | −0.12 | | |
| 4 | 0.85 | 0.9 | 1.02 | 0.87 | 1.52 | | | −0.15 | −0.25 | −0.23 | −0.36 | 0.16 | | | 0 | −0.05 | −0.08 | −0.24 | −0.24 | | |
| 5 | 0.87 | 0.86 | 0.97 | 0.94 | 1.43 | | | −0.13 | −0.27 | −0.3 | −0.36 | 0.07 | | | 0 | −0.07 | −0.17 | −0.33 | −0.33 | | |
| 6 | 0.87 | 0.89 | 0.89 | 0.91 | 1.41 | | | −0.13 | −0.24 | −0.35 | −0.44 | −0.03 | | | 0 | −0.04 | −0.19 | −0.43 | −0.43 | | |
| 7 | 0.86 | 0.92 | 0.99 | 1.04 | 1.54 | | | −0.14 | −0.22 | −0.23 | −0.19 | 0.35 | | | 0 | −0.02 | −0.05 | −0.05 | −0.05 | | |
| 8 | 0.85 | 0.86 | 0.97 | 1.14 | 1.37 | | | −0.15 | −0.29 | −0.32 | −0.18 | 0.19 | | | 0 | −0.09 | −0.21 | −0.21 | −0.21 | | |
| 9 | 0.87 | 0.93 | 0.88 | 0.91 | 1.48 | | | −0.13 | −0.2 | −0.32 | −0.41 | 0.07 | | | 0 | 0 | −0.12 | −0.33 | −0.33 | | |
| 10 | 0.86 | 0.85 | 0.92 | 0.92 | 1.34 | | | −0.14 | −0.29 | −0.37 | −0.45 | −0.11 | | | 0 | −0.09 | −0.26 | −0.51 | −0.51 | | |
| 11 | 0.85 | 0.89 | 0.91 | 0.85 | 1.39 | | | −0.15 | −0.26 | −0.35 | −0.5 | −0.11 | | | 0 | −0.06 | −0.21 | −0.51 | −0.51 | | |
| 12 | 0.86 | 0.92 | 0.87 | 1.14 | 1.43 | | | −0.14 | −0.22 | −0.35 | −0.21 | 0.22 | | | 0 | −0.02 | −0.17 | −0.18 | −0.18 | | |
| 13 | 0.85 | 0.87 | 0.9 | 1.01 | 1.34 | | | −0.15 | −0.28 | −0.38 | −0.37 | −0.33 | | | 0 | −0.08 | −0.26 | −0.43 | −0.43 | | |
| 14 | 0.85 | 0.89 | 0.98 | 0.97 | 1.46 | | | −0.15 | −0.26 | −0.28 | −0.31 | 0.15 | | | 0 | −0.06 | −0.14 | −0.25 | −0.25 | | |
| 15 | 0.87 | 0.9 | 1 | 0.93 | 1.54 | | | −0.13 | −0.23 | −0.23 | −0.3 | 0.24 | | | 0 | −0.03 | −0.06 | −0.16 | −0.16 | | |
| 16 | 0.87 | 0.85 | 0.86 | 0.94 | 1.3 | | | −0.13 | −0.28 | −0.42 | −0.48 | −0.18 | | | 0 | −0.08 | −0.3 | −0.58 | −0.58 | | |
| 17 | 0.87 | 0.9 | 1.01 | 0.95 | 1.55 | | | −0.13 | −0.23 | −0.22 | −0.27 | 0.28 | | | 0 | −0.03 | −0.05 | −0.12 | −0.12 | | |
| 18 | 0.87 | 0.88 | 0.86 | 1.07 | 1.36 | | | −0.13 | −0.25 | −0.39 | −0.32 | 0.04 | | | 0 | −0.05 | −0.24 | −0.36 | −0.36 | | |
| 19 | 0.86 | 0.93 | 1 | 1.12 | 1.47 | | | −0.14 | −0.21 | −0.21 | −0.09 | 0.38 | | | 0 | −0.01 | −0.02 | −0.02 | −0.02 | | |
| 20 | 0.87 | 0.85 | 0.96 | 0.94 | 1.4 | | | −0.13 | −0.28 | −0.32 | −0.38 | 0.02 | | | 0 | −0.08 | −0.2 | −0.38 | −0.38 | | |
| AVE | 0.86 | 0.89 | 0.94 | 0.98 | 1.43 | | | −0.14 | −0.25 | −0.31 | −0.33 | 0.11 | | | 0.00 | −0.05 | −0.16 | −0.29 | −0.29 | | |

With the negative UF Limit set at 20%, neither Patient A nor Patient B encounters a drain/fill volume ratio that exceeds 1.6 during the course of the twenty therapies comprising data contained in Tables 4 and 8, each therapy including five cycles. The unused fluid/fill volume ratio with the 20% negative UF limit in Tables 4 and 8 averages 25% and 29%, which means that 25% and 29% of 2000 ml (500 ml to 580 ml) of dialysis solution is unused. Thus, system 10, using the negative UF limit to determine when to short fill volumes without increasing the number of cycles, would reduce the effectiveness of the 10,000 ml therapy by around 5% (500/10,000=5%, to 580/10,000=5.8%).

Figure 11C:
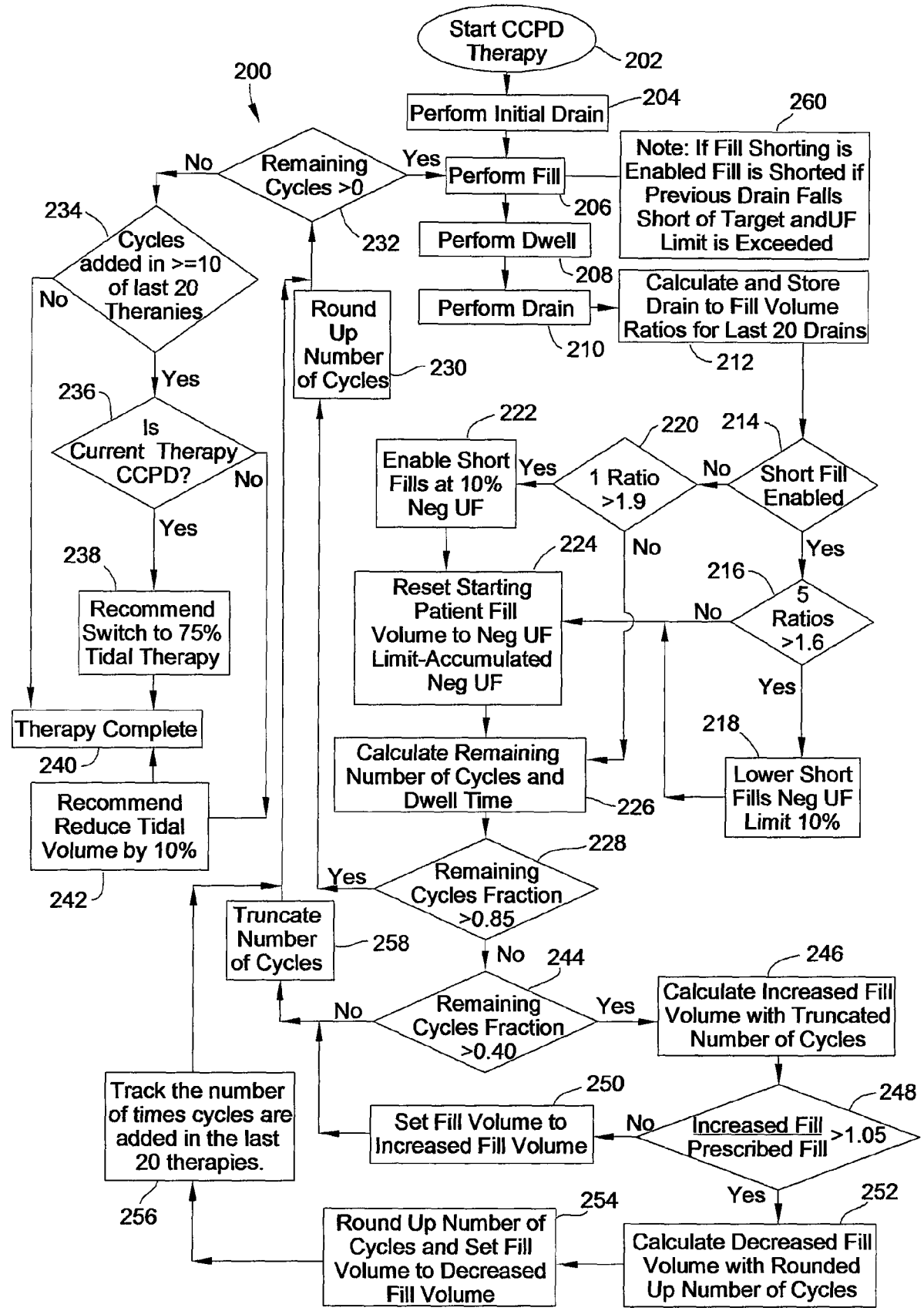

Referring now to FIG. 11C, flow diagram 200 illustrates one embodiment of a system 10 in which CCPD therapy is intended and begun. In this embodiment, the therapy may be switched to tidal therapy if the drains are incomplete or if too much dialysis fluid is not being used. The method begins at oval 202. At block 204, the system 10 performs an initial drain, followed by block 206 with a fill. Per block 260, for drains after the initial drain, a shorter fill volume will be used, i.e., the fill is shorted, if the previous drain falls short of the target volume and the UF limit is exceeded. The user sets a programmable negative UF limit, such as 40% negative UF, that is used to determine when to use shorter fill volumes after one or more incomplete drains when running a CCPD therapy, or if a switch has been made, when running a Tidal therapy. Other limits may be used, as mentioned above for the processes of FIGS. 11A and 11B.

After the fill, a dwell at block 208 is performed, the dwell calculated as previously discussed. After the dwell, a drain is performed at block 210. Based on the drain, the ratio of the drain volume to fill volume is calculated, and the ratio for the last twenty drains is calculated and stored at block 212. At diamond 214, the system questions whether a short fill was enabled for the previous cycle. If not, the ratio for the previous twenty cycles is compared to determine whether any of the cycles had a ratio greater than 1.9 at diamond 220. If not, the process continues to block 226 where the number of remaining cycles and the dwell time is calculated. If any of the previous twenty cycles had a ratio greater than 1.9, then the process enables short fills at the set limit for negative UF, such as 40% UF, at block 222, and then proceeds to block 224.

Returning to diamond 214, if a short fill was enabled for a previous cycle, the process continues to diamond 216. At this point, the ratios are analyzed to determine whether the ratio exceeded 1.6 for five of the twenty previous cycles. Other embodiments may use other benchmarks than five of the previous twenty cycles, for example, four or six of the previous ten cycles. If yes, the negative UF limit may be reset or lowered 10% and the process continued to block 224. If not, the process also continues to block 224. At block 224, the patient fill volume is reset to the negative UF limit minus the accumulated negative UF. For all the eventualities from blocks 222 and 224, and diamonds 214, 216 and 220, the next step is block 226, at which the remaining number of cycles and the dwell time for each is calculated.

For CCPD therapies, system 10 calculates the remaining number of CCPD cycles using the equation: Cycles Remaining=(total remaining therapy volume−last fill volume (if any))/(programmed fill volume). For Tidal therapies after an incomplete tidal drain, or after a complete full drain, system 10 calculates the remaining number of tidal cycles using the equation: Cycles Remaining=1+(Remaining Therapy Volume−Fill Volume−Last Fill Volume)/(Tidal PerCent*Fill Volume). For Tidal therapies after a complete tidal drain, system 10 calculates the remaining number of tidal cycles using the equation: Cycles Remaining=(Remaining Therapy Volume−Last Fill Volume)/(Tidal PerCent*Fill Volume).

At diamond 228 if the fractional number of cycles exceeds 0.85, the number of cycles is rounded up to the nearest integer, per block 230. At diamond 232, system 10 compares the number of remaining cycles to zero. If the number of cycles remaining is greater than zero, the next fill is performed, per block 206 and the process is repeated. If the number of cycles is zero, the decision tree proceeds to diamond 234. If no additional cycles were required in ten or more of the previous twenty therapies, the therapy is complete, per block 240. If additional cycles were required in ten or more of the previous twenty therapies, diamond 236 asks whether the current therapy is tidal (not CCPD). If the current therapy is tidal and is not CCPD, a recommendation is made for the next therapy to reduce the tidal volume by 10% in block 242. Therapy is adjudged complete for this particular therapy at block 240. Returning to block 236, if the patient is presently using CCPD therapy, and additional cycles were required in ten or more (half of more) of the previous twenty therapies, a switch to 75% tidal therapy is recommended for the next therapy, after which the present therapy is complete.

Returning to diamond 228, if the fractional number of cycles is less than 0.85, the process moves to diamond 244, and the number of fractional cycles is compared to 0.40. If the fractional number of cycles is less than 0.40, the remaining number of cycles is truncated at block 258 and the truncated or rounded down number of cycles is compared to zero at block 232. If the number of remaining cycles is zero, the process follows the decision tree discussed above for diamond 234. If the number of remaining cycles is an integer of 1 or more, the next fill is performed, per block 206.

Returning to diamond 244, if the fractional cycle remaining exceeds 0.4, a truncated number or rounded down number of cycles is used to calculate an increased fill volume at block 246. At block 248, the increased fill volume based on the lower number of cycles is compared with the fill volume based on the present prescription. The fill volume is calculated to use the total therapy volume in the rounded down or truncated number of cycles. The volumes are calculated as follows:

higher fill volume=(remaining therapy volume−last fill volume)/rounded down number of cycles.

If the ratio of the increased fill volume to prescribed fill volume based on the lower number cycles is less than 1.05 (i.e., the increase is less than 5%), as seen at diamond 248, system 10 resets the fill volume for the next fill to the calculated increased fill volume at block 250. The system then uses the truncated number of cycles, per block 258, and returns through comparison diamond 232 to the next fill at block 206 or the decision tree at block 234. The ratio at block 248 may be greater than 1.05, reflecting a significant increase in the fill volume of the next cycle compared with the most recent. In order to avoid such abrupt changes, the system 10 at block 252 then rounds up the previously-truncated number of cycles (from block 246) and then calculates a decreased fill volume using the higher number of cycles. The calculation used is:

lower fill volume=(remaining therapy volume−last fill volume)/rounded up number of cycles.

The system 10 then uses this rounded-up number and a decreased fill volume at block 254 for the next cycle. This decreased fill volume is noted and is tracked at block 256 as an added cycle. The added cycle is noted in comparison diamond 234.

Example for Patient C, per Table 9 and FIG. 11C: The negative UF limit may be combined with the Unused fluid volume limit to better control the operation of system 10, as seen in FIG. 11C. Table 9 contains four sub-tables, three similar to the others discussed above, and a fourth sub-table that depicts the actual fill volume/programmed fill volume (Actual FV/Programmed FV). This fourth sub-table demonstrates that the increased fill volume due to incomplete drains, in this case, does not exceed 20% of the programmed fill volume, as was the case above in the Example for Patient A and Patient B. However, in this case, a cycle is added any time the Unused Fluid/Fill Volume ratio in any of columns 3 through 5 goes more negative than −0.40. In fifteen of the 20 therapies all of the available fluid is used (see column 6, "0" unused fluid/FV ratio).

TABLE 9

5 × 2 Therapy Changes to 2 × 2 + 3 shorted + 1 with new fill volume (remainder of fluid)
CCPD Therapy with Negative UF Limit Set to 20%
Patient C

| | DV/FV | | | | | | UF/FV | | | | | | Unused Fluid/FV | | | | | |
|---|---|---|---|---|---|---|---|---|---|---|---|---|---|---|---|---|---|---|
| Day | 1 | 2 | 3 | 4 | 5 | 6 | 1 | 2 | 3 | 4 | 5 | 6 | 1 | 2 | 3 | 4 | 5 | 6 |
| 1 | 0.86 | 0.87 | 0.85 | 0.9 | 0.96 | 1.59 | −0.14 | −0.27 | −0.42 | −0.52 | −0.56 | 0.03 | 0 | 0 | −0.07 | −0.29 | −0.61 | 0 |
| 2 | 0.86 | 0.87 | 0.94 | 0.94 | 1.4 | | −0.14 | −0.27 | −0.33 | −0.39 | 0.01 | | 0 | 0 | −0.07 | −0.2 | −0.39 | |
| 3 | 0.85 | 0.87 | 0.94 | 0.93 | 1.38 | 1.4 | −0.15 | −0.28 | −0.34 | −0.41 | −0.03 | 0.37 | 0 | 0 | −0.08 | −0.22 | −0.43 | 0 |
| 4 | 0.85 | 0.85 | 0.86 | 0.9 | 0.91 | 1.67 | −0.15 | −0.3 | −0.44 | −0.54 | −0.63 | 0.04 | 0 | 0 | −0.1 | −0.34 | −0.68 | 0 |
| 5 | 0.85 | 0.87 | 0.87 | 1 | 1.31 | 1.3 | −0.15 | −0.28 | −0.41 | −0.41 | −0.1 | 0.20 | 0 | 0 | −0.08 | −0.29 | −0.5 | 0 |
| 6 | 0.87 | 0.87 | 0.95 | 0.93 | 1.43 | | −0.13 | −0.26 | −0.31 | −0.38 | 0.05 | | 0 | 0 | −0.06 | −0.17 | −0.35 | |
| 7 | 0.87 | 0.87 | 0.91 | 1.01 | 1.39 | | −0.13 | −0.26 | −0.35 | −0.34 | 0.05 | | 0 | 0 | −0.06 | −0.21 | −0.35 | |
| 8 | 0.86 | 0.86 | 0.95 | 0.91 | 1.39 | 1.4 | −0.14 | −0.28 | −0.33 | −0.42 | −0.03 | 0.37 | 0 | 0 | −0.08 | −0.21 | −0.43 | 0 |
| 9 | 0.85 | 0.86 | 0.85 | 0.93 | 1.05 | 1.5 | −0.15 | −0.29 | −0.44 | −0.51 | −0.46 | 0.04 | 0 | 0 | −0.09 | −0.33 | −0.64 | 0 |
| 10 | 0.85 | 0.85 | 0.91 | 0.91 | 0.99 | 1.6 | −0.15 | −0.3 | −0.39 | −0.48 | −0.49 | 0.11 | 0 | 0 | −0.1 | −0.29 | −0.57 | 0 |
| 11 | 0.87 | 0.85 | 0.94 | 1 | 1.38 | | −0.13 | −0.28 | −0.34 | −0.34 | 0.04 | | 0 | 0 | −0.08 | −0.22 | −0.36 | |

TABLE 9-continued

5 × 2 Therapy Changes to 2 × 2 + 3 shorted + 1 with new fill volume (remainder of fluid)
CCPD Therapy with Negative UF Limit Set to 20%
Patient C

| 12 | 0.87 | 0.86 | 0.86 | 0.92 | 0.92 | 1.62 | −0.13 | −0.27 | −0.41 | −0.49 | −0.57 | 0.05 | 0 | 0 | −0.07 | −0.28 | −0.57 | 0 |
|---|---|---|---|---|---|---|---|---|---|---|---|---|---|---|---|---|---|---|
| 13 | 0.85 | 0.87 | 0.86 | 1.03 | 1.3 | 1.5 | −0.15 | −0.28 | −0.42 | −0.39 | −0.09 | 0.41 | 0 | 0 | −0.08 | −0.3 | −0.49 | 0 |
| 14 | 0.85 | 0.85 | 0.88 | 1.04 | 1.28 | 1.45 | −0.15 | −0.3 | −0.42 | −0.38 | −0.1 | 0.35 | 0 | 0 | −0.1 | −0.32 | −0.5 | 0 |
| 15 | 0.85 | 0.87 | 0.88 | 0.9 | 0.9 | 1.63 | −0.15 | −0.28 | −0.4 | −0.5 | −0.6 | 0.03 | 0 | 0 | −0.08 | −0.28 | −0.58 | 0 |
| 16 | 0.87 | 0.86 | 0.88 | 1.01 | 1.34 | 1.3 | −0.13 | −0.27 | −0.39 | −0.38 | −0.04 | 0.26 | 0 | 0 | −0.07 | −0.26 | −0.44 | 0 |
| 17 | 0.85 | 0.85 | 0.94 | 0.92 | 1.34 | 1.45 | −0.15 | −0.3 | −0.36 | −0.44 | −0.1 | 0.35 | 0 | 0 | −0.1 | −0.26 | −0.5 | 0 |
| 18 | 0.86 | 0.86 | 0.88 | 0.85 | 0.9 | 1.7 | −0.14 | −0.28 | −0.4 | −0.55 | −0.65 | 0.05 | 0 | 0 | −0.08 | −0.28 | −0.63 | 0 |
| 19 | 0.87 | 0.86 | 0.86 | 1.05 | 1.32 | 1.36 | −0.13 | −0.27 | −0.41 | −0.36 | −0.04 | 0.32 | 0 | 0 | −0.07 | −0.28 | −0.44 | 0 |
| 20 | 0.87 | 0.87 | 0.89 | 1 | 1.37 | | −0.13 | −0.26 | −0.37 | −0.37 | 0 | | 0 | 0 | −0.06 | −0.23 | −0.4 | |
| AVE | 0.86 | 0.89 | 1.00 | 1.37 | 1.21 | 1.50 | −0.14 | −0.28 | −0.38 | −0.43 | −0.22 | 0.28 | 0.00 | 0.00 | −0.08 | −0.26 | −0.49 | 0.00 |

| | Actual FV/Programmed FV | | | | | |
|---|---|---|---|---|---|---|
| Day | 1 | 2 | 3 | 4 | 5 | 6 |
| 1 | 1.00 | 1.14 | 1.20 | 1.20 | 0.81 | 0.81 |
| 2 | 1.00 | 1.14 | 1.20 | 1.20 | 1.20 | 1.20 |
| 3 | 1.00 | 1.15 | 1.20 | 1.20 | 0.72 | 0.72 |
| 4 | 1.00 | 1.15 | 1.20 | 1.20 | 0.84 | 0.84 |
| 5 | 1.00 | 1.15 | 1.20 | 1.20 | 0.75 | 0.75 |
| 6 | 1.00 | 1.13 | 1.20 | 1.20 | 1.20 | 1.20 |
| 7 | 1.00 | 1.13 | 1.20 | 1.20 | 1.20 | 1.20 |
| 8 | 1.00 | 1.14 | 1.20 | 1.20 | 0.72 | 0.72 |
| 9 | 1.00 | 1.15 | 1.20 | 1.20 | 0.82 | 0.82 |
| 10 | 1.00 | 1.15 | 1.20 | 1.20 | 0.79 | 0.79 |
| 11 | 1.00 | 1.13 | 1.20 | 1.20 | 1.20 | 1.20 |
| 12 | 1.00 | 1.13 | 1.20 | 1.20 | 0.79 | 0.79 |
| 13 | 1.00 | 1.15 | 1.20 | 1.20 | 0.75 | 0.75 |
| 14 | 1.00 | 1.15 | 1.20 | 1.20 | 0.75 | 0.75 |
| 15 | 1.00 | 1.15 | 1.20 | 1.20 | 0.79 | 0.79 |
| 16 | 1.00 | 1.13 | 1.20 | 1.20 | 0.72 | 0.72 |
| 17 | 1.00 | 1.15 | 1.20 | 1.20 | 0.75 | 0.75 |
| 18 | 1.00 | 1.14 | 1.20 | 1.20 | 0.82 | 0.82 |
| 19 | 1.00 | 1.13 | 1.20 | 1.20 | 0.72 | 0.72 |
| 20 | 1.00 | 1.13 | 1.20 | 1.20 | 1.20 | 1.20 |
| AVE | 1.00 | 1.14 | 1.20 | 1.20 | 0.88 | 0.88 |

At the present time in 2008, most APD patients perform CCPD therapies and there is no UF limit that results in an automatic shorting of the next fill when a drain is not complete. Succeeding fills are always full if the minimum drain volume was achieved during the previous drain. A negative UF alarm is sounded if the accumulation of negative UF exceeds an alarm limit, typically set at 50% of the programmed fill volume. The tracking of negative UF is based solely upon the volume drained less the volume filled and does not account for ultra-filtration across the peritoneal membrane. The method described herein tracks the ratio of the volume drained to the prescribed fill volume. Per the discussion above for FIG. 11C, if this ratio exceeds 1.9 once in every twenty drains, or if the ratio exceeds 1.6 five times in every twenty drains, the system will suggest that the user Enable the negative UF limit algorithm to limit fill volumes and add cycles as necessary to reduce the magnitude and incidence of increased intra-peritoneal volume.

FIG. 11C illustrates how the system monitors CCPD drain ratios and uses the results to suggest when the user should enable the negative UF limit algorithm to limit IIPV. The system will lower the UF threshold for shorting fills to limit the incidence of IIPV and low drain alarms. The system will also suggest when the user should switch to a tidal therapy.

As described above for block 220, system 10 suggests activating the negative UF limit algorithm if a drain volume/fill volume ratio exceeds 1.9 during any of the Drains 2 through N drains (the last drain) in more than one per twenty therapies.

At block 216, system 10 suggests lowering the negative UF limit setting if a drain/fill volume exceeds 1.6 during the first drain through N drains (the last drain) more than x occurrences in y therapies, e.g., more than five times in twenty therapies. Other embodiments may use other limits, for the drain volume/fill volume ratio, for the number of therapies in which a particular high ratio is encountered, or for both.

At diamond 220, system 10 monitors the drain to fill volume ratio and also monitors the unused fluid/fill volume (FV) ratio and determines whether the unused fluid/FV exceeds a certain ratio in a number of cycles in a given therapy. For example, system 10 may set 40% (a ratio of 0.40) in any of cycles 2 through N−2 of N (that is, the second-next-to last, e.g., cycles 2-3 in a five-cycle therapy or cycles 2-4 in a six-cycle therapy). In another example, the system may use 50% (a ratio of 0.50) in cycles 2 through N−1 (next to last), e.g., cycles 2-4 in a five-cycle therapy or cycles 2-5 in a six-cycle therapy, for which an example is given in Table 9. Note that in Table 9, the UF/FV ratio for day 1 at cycle 2 is −0.27, which exceeds the negative 20% limit that was used when generating Table 9. Thus, the next cycle is shorted by 7%, leading to an Unused Fluid/FV for day 1, cycle 3, of −0.07. At cycle 3, the UF/FV ratio rises to −0.42, i.e., again negative UF. Cycle 4 is now shorted 29% (−0.29=−0.07−0.22 for Unused Fluid/FV at day 1, cycle 4, since −0.42−(−0.20)= −0.22). The result of Cycle 4 is still negative UF (−0.52) and cycle 5 is again shorted (−0.61 Unused Fluid/FV). Since 0.61 exceeds 0.50 (50%), the number of cycles is increased by 1 (adding a sixth cycle) and the target patient fill volume is decreased, so that the remainder of the dialysis fluid is used in the sixth cycle.

At block 254, using the 50% example and if unused fluid/FV exceeds 50%, system 10 increases the remaining number of cycles by 1 and distributes the remaining dwell time and remaining therapy volume evenly over the increased remaining number of cycles (see, e.g., in Table 9, day 1, number of cycles increased to six when the unused fluid/FV ratio exceeds 0.50 (actually 0.61) in the column for cycle 4. At blocks 228 and 244 after the next fill cycle, system 10 calculates the unused Fluid/FV ratio (remaining cycler fraction) to zero for a therapy with a cycle added.

Returning to diamond 244, if the unused fluid/FV ratio is less than 40%, the system instead moves to diamond 258 and through eventually to diamond 234 when all of the available fluid has been delivered. At diamond 234, system 10 monitors the frequency at which an increased number of cycles is needed to prevent fluid loss in excess of a given percentage A (e.g., 50%) of the fill volume. If the frequency is equal to or greater than 50% of the time (e.g., ten times or more over twenty therapies), system 10 at block 236 suggests that the patient be converted to a tidal therapy since the patient is already in effect performing an 85% tidal therapy. For example, switching to a 75% tidal therapy may be a more effective use of the fluid volume that is available while minimizing the magnitude of excess intra-peritoneal volume and reducing the frequency of low drain volume alarms.

At block 256, system 10 uses UF trending discussed below to monitor the 75% (or current) tidal therapy. At diamond 234, system 10 determines whether the frequency at which the patient's residual volume has to be offset over time is greater than a specified percentage of the time, e.g., 50% percent of the time. If so, system 10 suggests switching to a lower percentage, e.g., 65%, tidal therapy at block 242 for the next therapy. If the residual volume still has to be offset greater than a certain percentage, e.g., 50%, of the time, as determined at diamond 234, the loop continues to lower the tidal percentage until the residual drain volume is lowered to an acceptable level, at which time the method of logic flow diagram 200 ends. Tidal therapies are still effective with regard to solute removal for tidal percentages as low as about 50%. Ultra-filtration can be maintained at tidal percentages lower than 50%.

If a patient still has drain issues with a tidal percentage of around 50%, the patient is a candidate for multi-pass continuous flow peritoneal dialysis (Multi-Pass CFPD) as discussed in US Pat. Appl. Publ. 20040019320, which is hereby incorporated herein by reference. Multi-Pass CFPD continuously fills and drains the patient using either a dual lumen catheter as discussed in US Pat. Appl. Publ. 20030204162 and U.S. Pat. No. 6,976,973, both of which are hereby incorporated herein by reference. Alternatively, two single lumen catheters may be used. The patient is only drained to below the prescribed fill volume prior to the start of the Multi-Pass CFPD therapy and at the end of the Multi-Pass CFPD therapy. Low drain volume alarms are virtually eliminated. Check Patient line alarms can still occur if the patient line becomes kinked.

Optimizing Tidal Therapies Via UF Trending

As discussed above, there is a need for an automated peritoneal dialysis therapy that ensures the use of all of the prescribed dialysis solution, can finish on time, can minimize if not eliminate low drain volume alarms and can prevent the volume of fluid in the patient's peritoneum from exceeding the programmed fill volume by more than about the amount of expected ultrafiltration ("UF") obtained from the patient over one dwell cycle. Properly estimating a patient's UF for a given solution is therefore important. It is contemplated that system 10, instead of using predicted UF values, uses recently trended UF values for the same type of treatment using the same type of PD solution.

Figure 12:
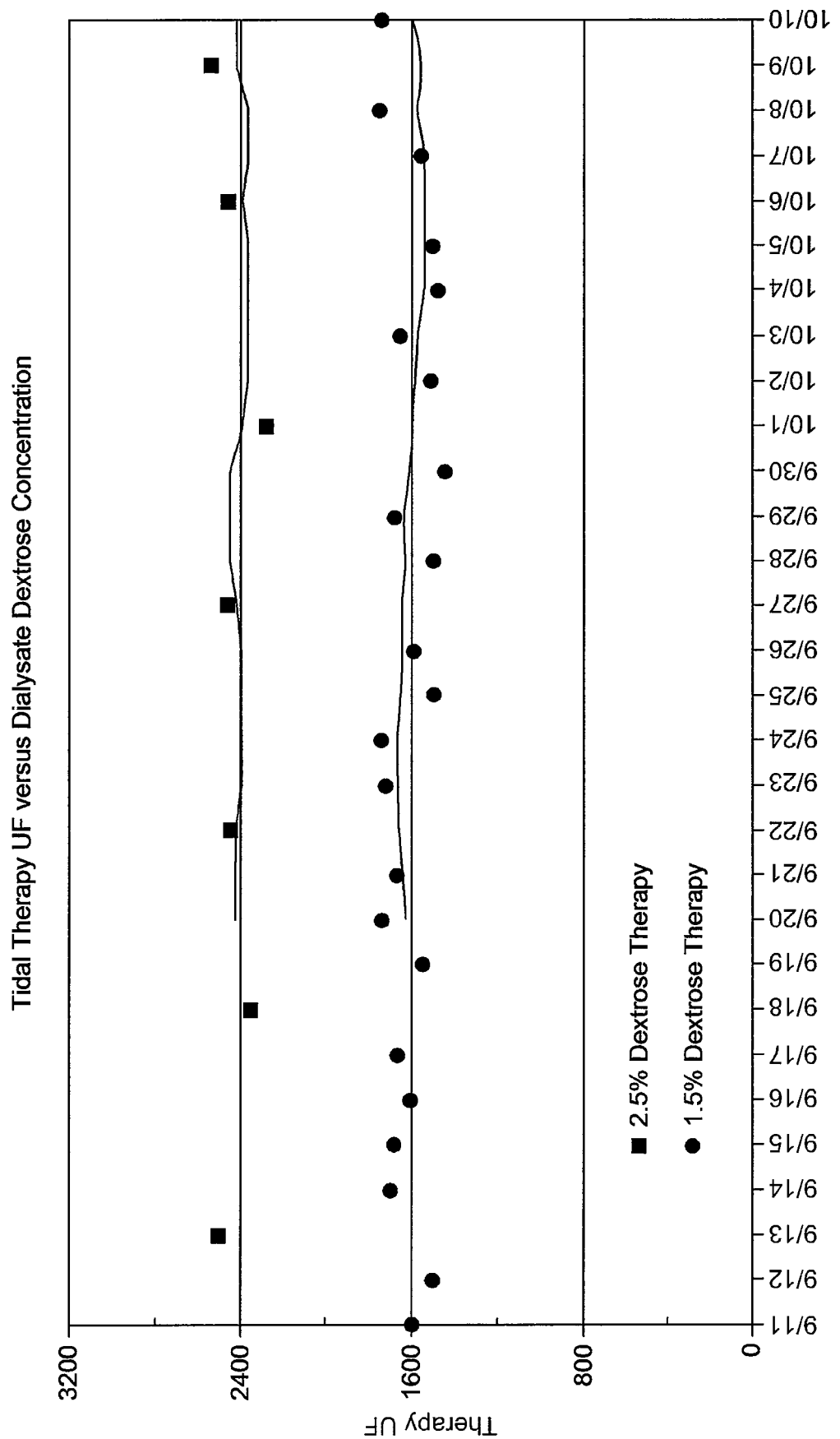
FIG. 12 is one example of a trend of UF removed from a patient over a number of treatment days, and for different dextrose level dialysates used, the trend used in combination with a tidal PD therapy.

Referring now to FIG. 12, a trend for a 50% tidal therapy with programmed UF based upon trending is shown for both 1.5% and 2.5% dextrose concentration dialysis solution types. The trended 50% therapy for the patient shows that about 2400 ml of UF is removed if that patient uses 2.5% dextrose and 1600 ml of UF is removed if that patient uses 1.5% dextrose.

The total UF is then divided out over the number of night therapy cycles (fills/dwells/drains) to determine the UF per cycle, e.g., four cycles resulting in 600 ml UF for 2.5% dextrose and 400 ml of UF for 1.5% dextrose. The values of 600 ml and 400 ml are added to the prescribed fill volumes to determine a patient's maximum allowable IPV in one embodiment. The maximum IPV is then used to determine the volume of residual fluid that should remain in the patient's peritoneum after a drain. For example, if the patient's maximum IPV is 2600 ml (2000 ml fill plus 600 ml UF), the residual volume for a fifty percent tidal drain should be 1300 ml. Just as important, the cycler of system 10 will attempt to remove 1300 ml over the drain.

Figure 17:
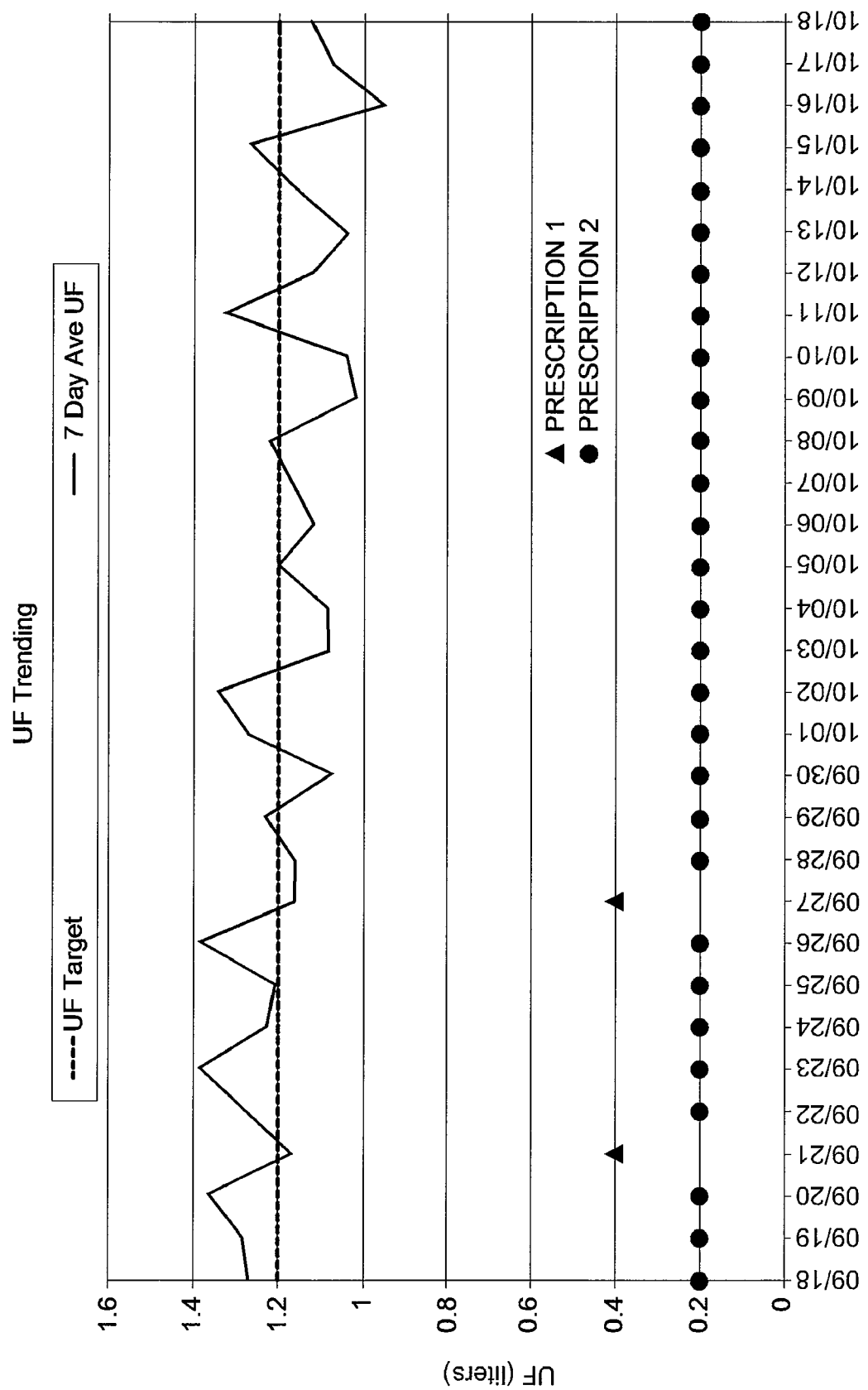
FIG. 17 is another example of a rolling average trend of UF removed from a patient over a number of treatment days.

FIG. 12 shows, for each dextrose level, each day's UF entry. System 10 in one embodiment determines the actual UF removed from the patient over the course of a night therapy (not counting last fill or day exchange). The actual UF measurement assumes a complete (to zero ml) drain prior to both the first fill and last or day fill (if performed). In this manner, System 10 knows how much fresh dialysate has been delivered to the patient and how much spent dialysate (including UF) has been removed from the patient over the nightly treatment. The difference is the night therapy UF, which is logged into data storage for the patient, the concentrate and therapy, and used to further update the trend. UF can be plotted as a single day (FIG. 12) or as a rolling average (FIG. 17). U.S. patent application Ser. No. 12/170,220 ("the Trending Application"), entitled "Dialysis System Having Trending and Alert Generation," filed Nov. 3, 2008, the pertinent portions of which are incorporated expressly herein by reference and relied upon, discloses different rolling average UF trends and trends using statistical process control ("SPC") for alarming/alerting. Such trends can be used alternatively or additionally to the single day trend shown in FIG. 12.

FIGS. 13, 14, 15 and 16 illustrate four different treatment scenarios. The continuous line indicates the volume of fluid that system 10 delivers and removes from the patient over time. The dashed line indicates the actual volume of fluid residing in the patient ("IPV") at any given point in time. The difference between the machine delivered/removed volume and the actual volume is the patient's UF. The dotted line indicates the actual UF removed from the patient over time.

Figure 13:
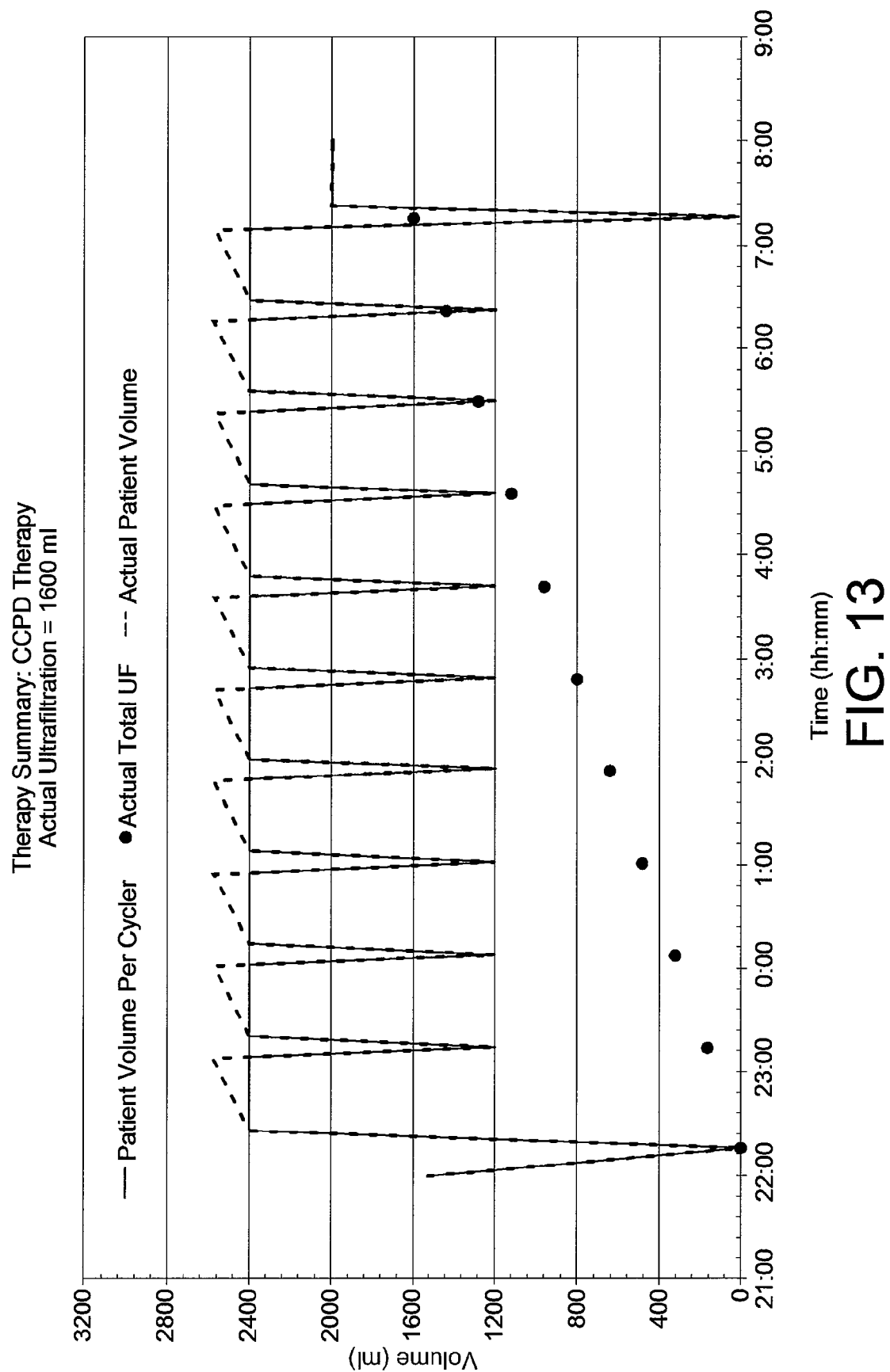
FIGS. 13 to 16 are IPV versus time graphs showing various examples of a tidal therapy performed using patient trended UF data.
Figure 14:
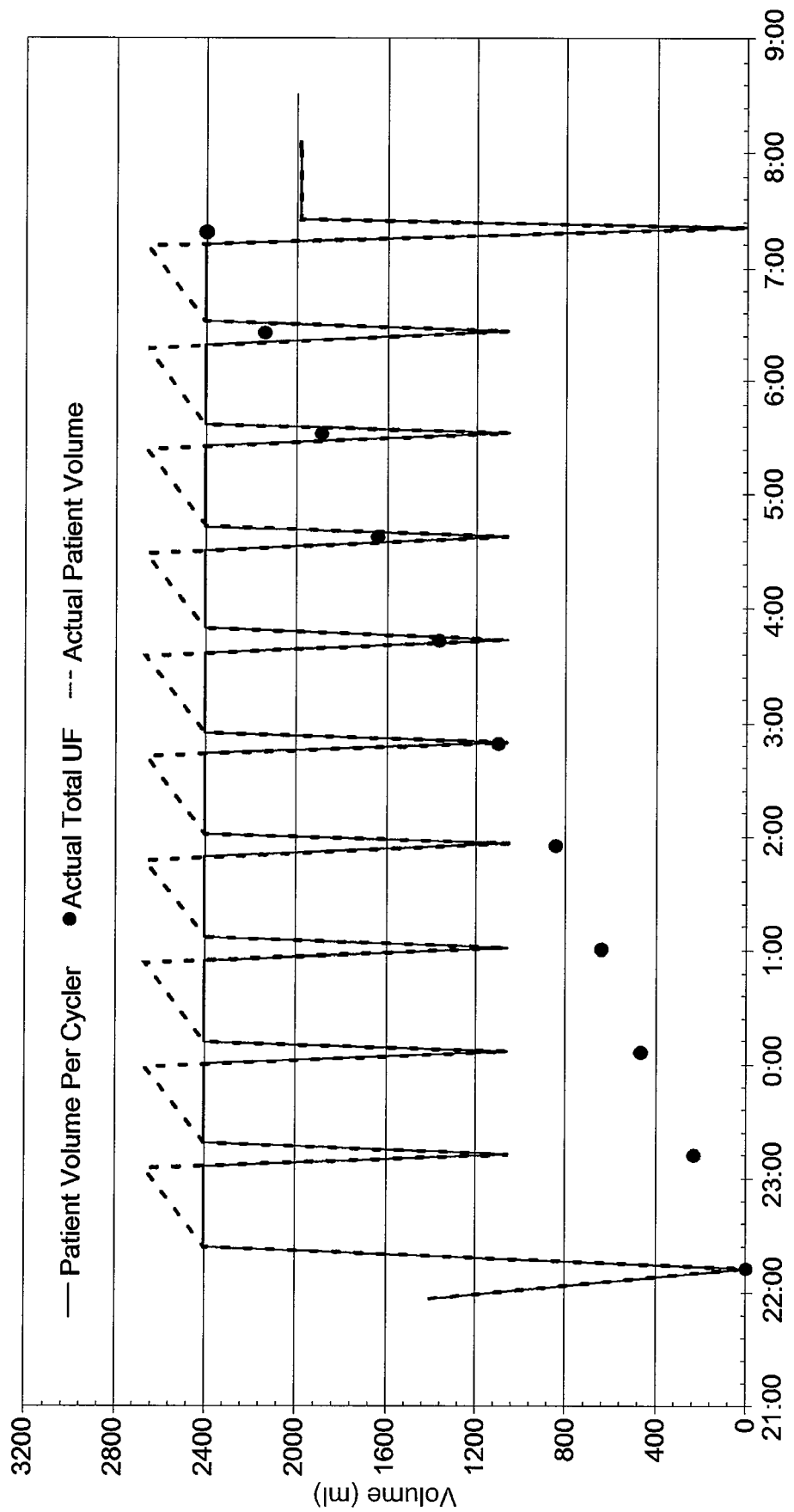

FIG. 13 illustrates a 50% tidal therapy using 1.5% dextrose dialysate. The trended 1600 ml total UF for such treatment is recalled from memory of system 10 and used to simulate the patient's actual IPV. The 1600 ml UF is split amongst ten treatments, yielding 160 ml removed per cycle as shown in FIG. 13. FIG. 14 illustrates a 50% tidal therapy using 1.5% dextrose dialysate. The trended 2400 ml total UF for this treatment is recalled from memory of system 10 and used to simulate the patient's actual IPV. The 2400 ml UF is also split amongst ten treatments, yielding 240 ml removed per cycle as shown in FIG. 14.

FIG. 15 again illustrates a 50% tidal therapy using 1.5% dextrose dialysate. The trended 1600 ml total UF for such treatment is recalled from memory of system 10 and used to simulate the patient's actual IPV. Here, however, the total UF removed is only 1280 ml, short by 320 ml. The 1280 ml UF is again split amongst ten treatments, yielding 128 ml removed per cycle as shown in FIG. 15. Because the predicted UF from the patient's actual trend set a good starting place, and because the 50% tidal therapy is forgiving in terms of having enough planned residual volume to accept lower than expected residual volumes (here due to less UF than expected), the treatment is able to use all of the prescribed solution, maintain the prescribed dwell times and finish therapy on time.

Figure 16:
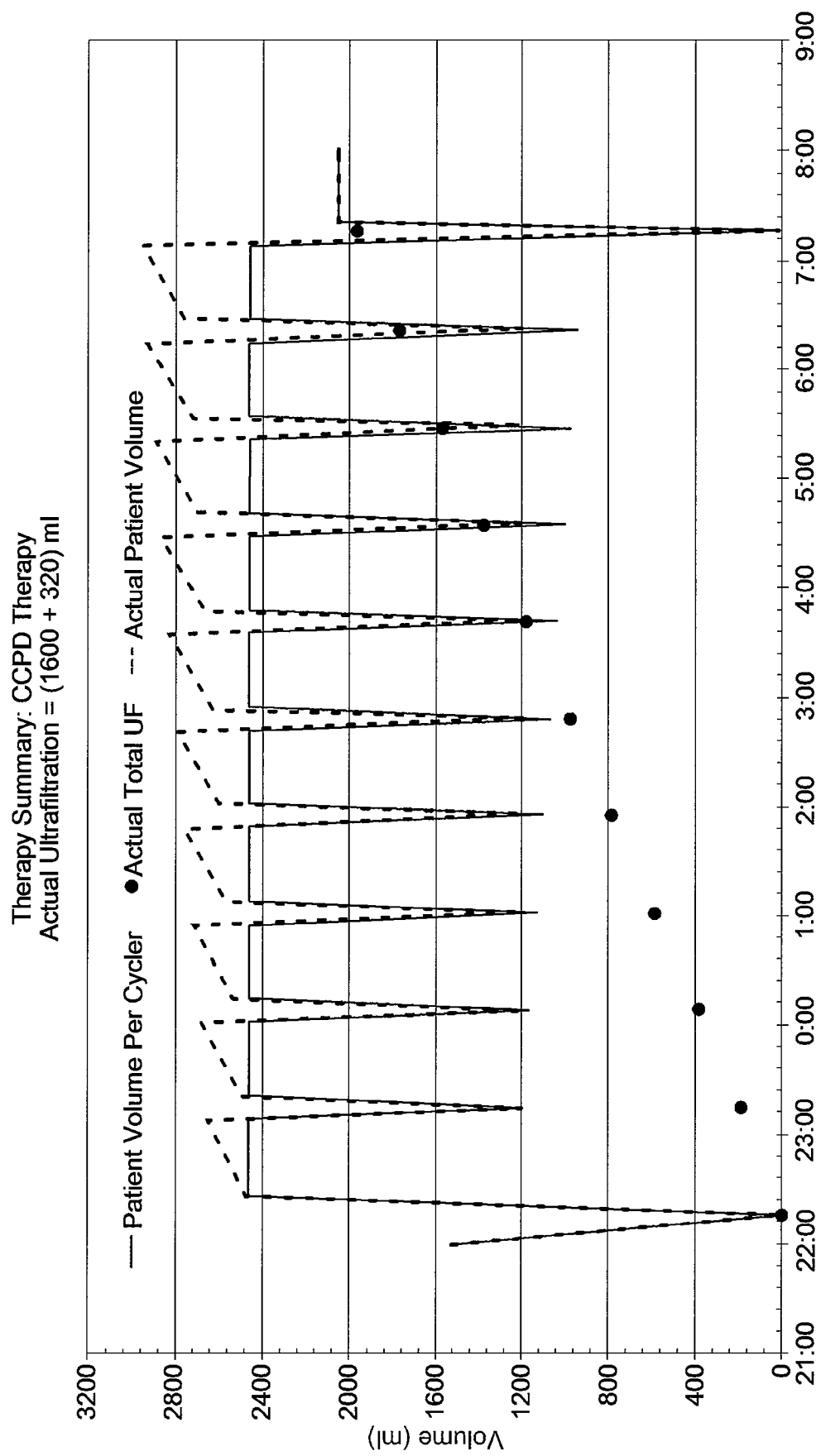

FIG. 16 again illustrates a 50% tidal therapy using 1.5% dextrose dialysate. The trended 1600 ml total UF for such treatment is recalled from memory of system 10 and used to simulate the patient's actual IPV. Here, however, the total UF removed is more than expected, 1920 ml, greater by 320 ml. The 1920 ml UF is again split amongst ten treatments, yielding 192 ml removed per cycle as shown in FIG. 16. Again, the predicted UF from the patient's actual trend set a good starting place. The 50% tidal therapy is forgiving in terms of setting the planned residual volume high enough so that the planned drain can take place each cycle, which at least does not add to the effect of the additional UF. The treatment is thus able to use all of the prescribed solution, maintain prescribed dwell times, and finish therapy on time.

In the therapies of FIGS. 15 and 16, all of the dialysis solution is used, the dwell times are as prescribed, the potential for low drain alarms is minimized and the maximum patient volume is limited to less than that with CCPD therapies. The trending of the UF (based upon osmotic concentration) accordingly allows tidal treatments to be used in a very advantageous manner.

In one embodiment, system 10 trends a running average of the patient's UF and displays same for both the patient and clinician. The displayed trended time interval can be varied from a week to a month to multiple months (see also Trending Application). The user in one embodiment can scroll forward or may scroll backward to see the results for the preceding ninety days. System 10 in one embodiment enables the user to select the prescription ID axis (e.g., via input device 22 (FIG. 1) or a touch screen operable with video monitor 20), after which system 10 changes the display to that shown in FIG. 12, in which two or more different prescriptions or dextrose levels are trended independently.

FIG. 17 shows which dialysate is used on a given day (prescription 1 or prescription 2), the desired UF volume, and a trended rolling seven day average actual UF. System 10 can therefore use as its predicted UF the previous day's UF volume (if the same therapy and dialysate is used) or an averaged UF data point for the same dialysate/treatment. As discussed in the Trending Application, the UF trends, e.g., FIGS. 12 and 17, may be maintained at the logic implementer of the cycler 12 or at a remote server, e.g., located at a dialysis clinic or doctor's office. In either case, networked communication can allow any one or more of the patient, clinician and doctor to view the UF trend.

As discussed, using trended UF values allows the programmed UF to be withdrawn during the tidal therapy to be predicted quite accurately. The actual patient volume ("IPV") will likewise trend very close to the IPV that the APD cycler 12 expects to be in the patient's peritoneum as illustrated in FIGS. 13 to 16. System 10 in one embodiment is programmed such that if the UF trend changes by more than a preset percentage, the system alerts the user so that he/she can consult a PD doctor or clinician. System 10 in one embodiment automatically adjusts the UF that is programmed for the osmotic agent being used to use the most recent UF trended data point.

Alternatively, the machine alerts the patent to make a change to the programmed UF, so that the user knows of the change. To this end, each osmotic agent or dextrose level dialysate can be associated with a different dialysate ID or number, which the patient enters into the system. System 10 then calls up a screen for the particular dialysate, so that the patient can make the machine suggested change. The Trending Application referenced above describes situations in which the patient's doctor or clinician is notified when the patient's UF trends too far away from an expected level for a particular dialysate.

It is important to drain the patient fully at the start of any APD therapy. This holds true for the 50% tidal therapy with UF based upon trending of multiple concentration osmotic agents. In the initial and final drains, however, the patient can be sitting up and will typically drain better, compared with draining when lying down in a supine position. The patient can also move around a little since he/she will be awake and is not inconvenienced when doing so.

System 10 in one embodiment knows how much fluid resides in the patient's peritoneum at the start of a therapy. The system remembers the type and volume that it filled the day before for a last fill. System 10 in one embodiment trends initial drain volumes and posts an alert if drain flow stops before the normal initial drain volume has been recovered knowing the previous day's last fill volume and dextrose level. System 10 can also query the user regarding any day exchange that the patient made the previous day not using machine 12 as a possible explanation for an abnormal initial drain.

Figure 18:
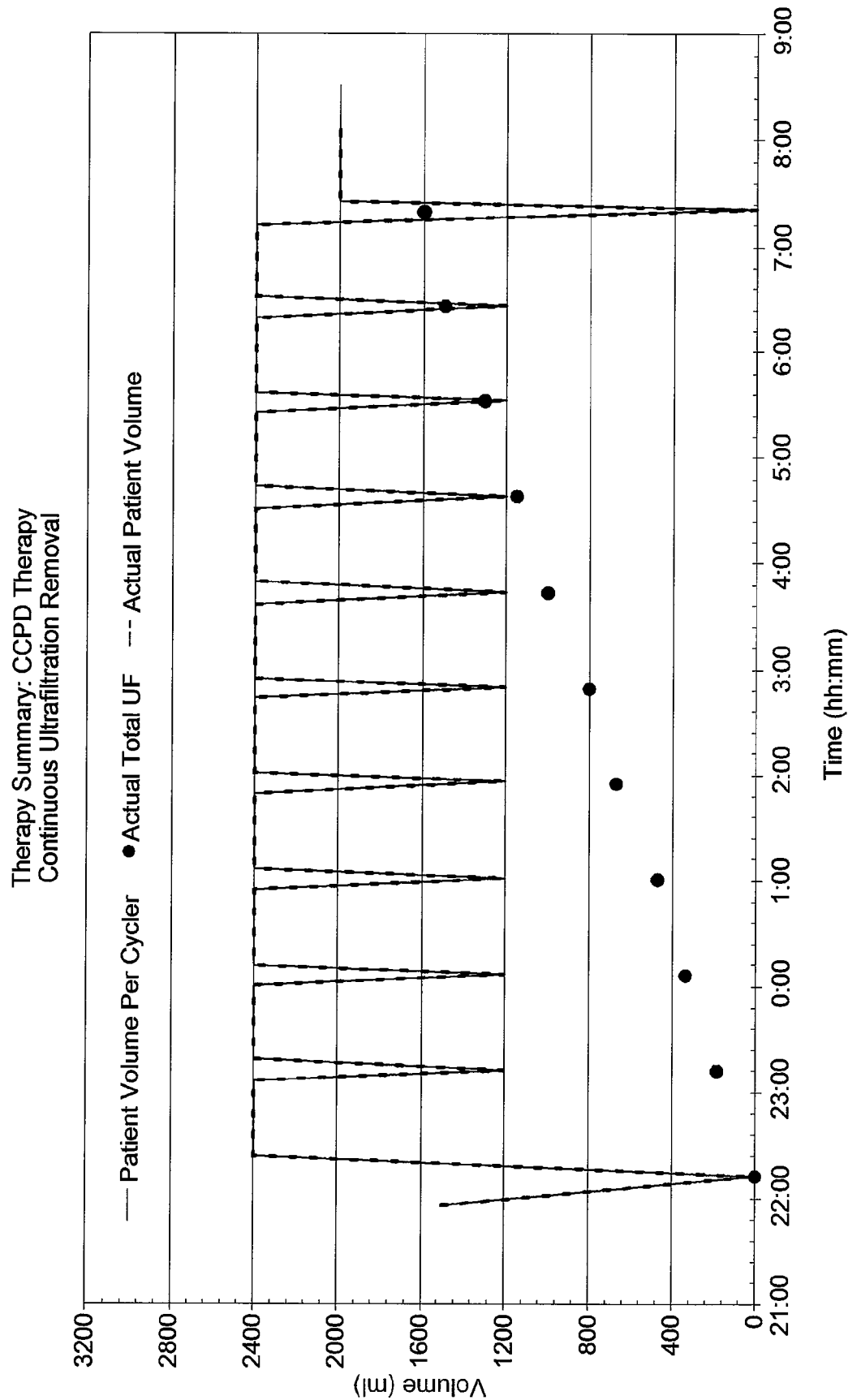
FIG. 18 is an IPV versus time graph showing one example of a tidal therapy performed using patient trended UF data, and in which UF is removed gradually from the patient over a dwell to limit the IPV.

FIG. 18 shows an alternative embodiment in which system 10 and machine 12 continuously remove UF during dwell so that the patient's IPV does not increase over the dwell. Here again, it is important to know the UF accurately for the patient and a particular dextrose level, in order to know how much fluid to remove from the patient over the dwell. The UF volume divided by the dwell time informs system 10 and cycler 12 of the proper flow rate at which to remove the UF volume from the patient.

While 50% tidal percentage with trended UF provides one very suitable therapy (see predicted results for different patients below), the percentage can be varied if desired or if a different percentage is predicted for a particular patient to have better clearance. For patients that typically drain well, the percentage can be higher, e.g., 65% or 75% and still allow prevent the vast majority of low drain alarms, prevent short fills, and complete therapy on time with the prescribed amount of dwell. Percentages below 50% are also possible.

Predicted Therapy Outcomes

Simulations were performed on APD Therapies (Tables 10 and 11) using PD prediction software called Renalsoft™, provided by the assignee of the present disclosure. The Trending Application referenced above discusses the prediction software in detail. The simulations were performed to show two different comparisons (i) 50% tidal (using trended UF prediction) versus standard APD Therapy (complete drains, no shorting of fills) and (ii) 85% tidal to simulate CCPD with 15% shorted next fills versus standard APD Therapy (complete drains, no shorting of fills). The software compared the therapies for the three patient body sizes and the four different PET categories, yielding twelve different patient types shown in Table 10.

TABLE 10

Definition of Patient Types

| Patient Type | Description: BSA Size and PET Category |
|---|---|
| 1 | BSA-Less Than-1.71-PET-HIGH |
| 2 | BSA-1.71-2.00-PET-HIGH |
| 3 | BSA-Greater Than-2.00-PET-HIGH |
| 4 | BSA-Less Than-1.71-PET-HIGH-AVE |
| 5 | BSA-1.71-2.00-PET-HIGH-AVE |
| 6 | BSA-Greater Than-2.00-PET-HIGH-AVE |
| 7 | BSA-Less Than-1.71-PET-LOW |
| 8 | BSA-Greater Than-2.00-PET-LOW |
| 9 | BSA-Less Than-1.71-PET-LOW-AVE |
| 10 | BSA-Less Than-1.71-PET-LOW-AVE |
| 11 | BSA-1.71-2.00-PET-LOW-AVE |
| 12 | BSA-Greater Than-2.00-PET-LOW-AVE |

As seen in Table 11, in all instances, the 50% tidal therapy resulted in higher creatinine clearances when compared to a standard CCPD therapy with full drains and no shorted fills. The results were consistent for both dry days and wet days. As shown, 50% tidal therapy based upon actual patient UF trending with both 1.5% and 2.5% dextrose dialysate offer superior clearances. And as discussed herein, 50% tidal therapy is shown to have fewer low drain volume alarms and better control of the volume of fluid in the patient when compared to conventional APD.

TABLE 11

Creatinine Clearance Increase (PerCent) for 50% Tidal over APD

| | No Last Fill = Dry Day | | | | Last Fill = Wet Day | | |
|---|---|---|---|---|---|---|---|
| Patient Type | 50% Tidal Creatinine Clearance L/wk/1.73 m² | Standard APD Creatinine Clearance L/wk/1.73 m² | Percent Increase | Patient Type | 50% Tidal Creatinine Clearance L/wk/1.73 m² | Standard APD Creatinine Clearance L/wk/1.73 m² | Percent Increase |
| 1 | 49.98 | 48.36 | 3.3% | 1 | 70.01 | 68.34 | 2.4% |
| 2 | 48.62 | 47.08 | 3.3% | 2 | 67.01 | 65.43 | 2.4% |
| 3 | 39.06 | 37.45 | 4.3% | 3 | 53.90 | 52.26 | 3.1% |
| 4 | 44.70 | 41.87 | 6.8% | 4 | 64.04 | 61.19 | 4.7% |
| 5 | 35.63 | 32.03 | 11.2% | 5 | 53.51 | 51.67 | 3.6% |
| 6 | 35.38 | 33.32 | 6.2% | 6 | 50.63 | 48.57 | 4.2% |
| 7 | 25.36 | 22.45 | 13.0% | 7 | 43.41 | 40.46 | 7.3% |
| 8 | 23.51 | 20.99 | 12.0% | 8 | 39.30 | 36.78 | 6.9% |
| 9 | 24.58 | 22.31 | 10.2% | 9 | 37.47 | 35.20 | 6.4% |
| 10 | 36.73 | 33.57 | 9.4% | 10 | 55.74 | 52.55 | 6.1% |
| 11 | 30.90 | 28.10 | 10.0% | 11 | 48.53 | 45.70 | 6.2% |
| 12 | 26.56 | 24.10 | 10.2% | 12 | 41.56 | 39.08 | 6.3% |

An alternative to the 50% tidal therapy is to short a subsequent fill in a CCPD therapy that experiences an incomplete drain when attempting to bring the patient's IPV to zero. The subsequent fill can be shorted by the amount that the previous drain was short. In this manner, system 10 limits the amount that the patient can be overfilled to the amount of fluid that has been ultrafiltered from the patient. Assuming, for example, that each drain is 15% short except for the last drain, the resulting change in creatinine clearance is shown in Table 12. For most patients, the clearances are reduced primarily because there is unused fluid left in the supply/heater bags at the end of the therapy. In the example illustrated below, 1080 ml out of a total therapy volume of 12000 ml (Dry Day) or 14000 ml (Wet Day) is not used.

The data in Table 12 predicts a reduced creatinine clearance when system 10 shorts succeeding fills by the amount that preceding drains fall short of recovering 100% of the previous fill volume. This is to be expected because some of the fresh dialysis solution was not used. Tables 10 and 11 show that a 50% tidal therapy is at least as effective as a properly performed APD CCPD therapy and does not run the risk of low drain alarms or fill shorts that the APD CCPD therapy runs.

Patient Recirculation

Single lumen patient lines have a recirculation volume (volume of fluid left in the patient line at the end of drain and returned at the start of the next fill) that reduces the therapeutic affect of the therapy. For example, if the internal volume of the patient line 38d (FIG. 1) is 42 ml and the fill volume is 1000 ml, 42/1000*100%=4.2% of the available fluid is wasted. Patients with larger fill volumes can use longer patient lines 38d without losing a larger percentage of their dialysis fluid. Patients with smaller fill volumes sometimes have to use shorter patient lines 38d with smaller inside diameters to avoid wasting a higher percentage of their dialysis solution.

TABLE 12

Creatinine Clearances for Smart APD (85% Tidal) Versus APD

| | No Last Fill = Dry Day | | | | Last Fill = Wet Day | | |
|---|---|---|---|---|---|---|---|
| Patient Type | 85% Tidal Creatinine Clearance L/wk/1.73 m² | Standard APD Creatinine Clearance L/wk/1.73 m² | Percent Change | Patient Type | 85% Tidal Creatinine Clearance L/wk/1.73 m² | Standard APD Creatinine Clearance L/wk/1.73 m² | Percent Change |
| 1 | 46.12 | 48.36 | −4.6% | 1 | 66.11 | 68.34 | −3.3% |
| 2 | 44.92 | 47.08 | −4.6% | 2 | 63.27 | 65.43 | −3.3% |
| 3 | 35.82 | 37.45 | −4.4% | 3 | 50.63 | 52.26 | −3.1% |
| 4 | 40.78 | 41.87 | −2.6% | 4 | 60.08 | 61.19 | −1.8% |
| 5 | 32.77 | 32.03 | 2.3% | 5 | 50.60 | 51.67 | −2.1% |
| 6 | 32.32 | 33.32 | −3.0% | 6 | 47.55 | 48.57 | −2.1% |
| 7 | 22.70 | 22.45 | 1.1% | 7 | 40.71 | 40.46 | 0.6% |
| 8 | 21.15 | 20.99 | 0.8% | 8 | 36.90 | 36.78 | 0.3% |
| 9 | 22.27 | 22.31 | −0.2% | 9 | 35.12 | 35.20 | −0.2% |
| 10 | 33.28 | 33.57 | −0.9% | 10 | 52.23 | 52.55 | −0.6% |
| 11 | 27.95 | 28.10 | −0.5% | 11 | 45.53 | 45.70 | −0.4% |
| 12 | 23.97 | 24.10 | −0.5% | 12 | 38.93 | 39.08 | −0.4% |

The 50% tidal therapy discussed herein will drain and fill moving a smaller solution volume when compared to a standard APD therapy. A patient with a 2000 ml fill volume on 50% tidal is accordingly wasting the same percentage of dialysis solution as a patient with a 1000 ml fill volume on full drain APD.

In one embodiment, system 10 addresses the recirculation issue by limiting the length of the standard patient line to about twenty-two feet instead of the thirty-three feet that currently can be used.

Alternately, patient line 38*d* is a dual lumen patient line, so that only the transfer set volume is recirculated. Dual lumen patient line 38*d* does not result in an increase in the size of the patient's transfer set. Using dual lumen patient line 38*d* allows the length of the line to be any desired, suitable length, and the same disposable set 30 (FIG. 1) and cassette 50 (FIG. 2) can be used for both the low fill mode and the standard fill mode. One suitable dual lumen patient line 38*d* and method therefore is disclosed in U.S. patent application Ser. No. 11/773,795, entitled, "Dialysis System Having Dual Patient Line Connection And Prime", filed Jul. 5, 2007, the relevant portion of which is incorporated herein by reference and relied upon.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An automated peritoneal dialysis system comprising:
at least one dialysis fluid pump configured to pump a dialysis fluid to and from a patient over a treatment, the treatment including a plurality of patient fills, dwells, and drains;
at least one conduit positioned and arranged to allow effluent dialysis fluid to be removed from the patient during the plurality of patient drains;
at least one processor; and
at least one memory device storing a plurality of instructions executed by the at least one processor to: (i) control the dialysis fluid pumped by the at least one dialysis fluid pump to and from a patient over the treatment and (ii) use at least one trended ultrafiltration ("UF") data point for the patient to determine an amount of effluent dialysis fluid to remove from the patient through the at least one conduit during at least one of the patient drains.

2. The dialysis system of claim 1, wherein the trended UF data point is an averaged UF data point.

3. The dialysis system of claim 1, the trended UF data point obtained from a trend maintained by one of the at least one processor/memory device and a remote server in communication with the logic implementer.

4. The dialysis system of claim 1, wherein the trended UF data point is a most recent data point on a trend of multiple UF data points.

5. The dialysis system of claim 1, wherein the trended UF data point is specific to a particular dialysis fluid.

6. The dialysis system of claim 1, the at least one processor/memory device configured to use the at least one UF data point with a programmed fill volume to determine the amount of effluent dialysis fluid to remove.

7. The dialysis system of claim 6, wherein the at least one processor/memory device is configured to determine the amount of effluent dialysis fluid to remove as a percentage of at least one of the UF data point plus the programmed fill volume.

8. The dialysis system of claim 7, wherein the percentage is set low enough to ensure that the amount of effluent dialysis fluid can be removed in each of a plurality of patient drains.

9. The dialysis system of claim 6, wherein the at least one processor/memory device is configured to determine the amount of the effluent dialysis fluid to remove by adding the UF data point to the programmed fill volume.

10. The dialysis system of claim 1, wherein the at least one processor/memory device is configured to (i) determine an actual amount of UF removed over the treatment and (ii) use the actual amount removed to update a UF trend including the UF data point.

11. The dialysis system of claim 1, which includes an initial drain in which the UF data point is not used to determine an amount of effluent dialysis fluid removed from the patient.

12. An automated peritoneal dialysis system comprising:
at least one dialysis fluid pump configured to pump a dialysis fluid to and from a patient over a treatment, the treatment including a plurality of patient fills, dwells and drains;
at least one dialysis fluid conduit constructed and arranged to allow effluent dialysis fluid to be removed from the patient during the plurality of patient drains;
at least one processor; and
at least one memory device storing a plurality of instructions executed by the at least one processor to: (i) control the dialysis fluid pumped by the at least one dialysis fluid pump to and from a patient over the treatment, (ii) access a trend of ultrafiltration data points for the patient, and (iii) use at least one of the UF data points to predict the patient's intra-peritoneal volume ("IPV") at an end of at least one of the plurality of patient dwells to determine at least one of (a) a subsequent fill volume, and (b) a subsequent drain volume.

13. The dialysis system of claim 12, the UF data point used being at least one of a (i) a most recent UF data point; and (ii) an averaged UF data point.

14. The dialysis system of claim 12, the at least one processor/memory device further configured to update the UF trend based on actual UF removed over the treatment.

15. The dialysis system of claim 12, the at least one processor/memory device configured to add a measured patient fill amount to the at least one UF data point to determine the IPV.

16. The dialysis system of claim 12, the at least one processor/memory device further configured to subtract a measured patient drain amount from the IPV to determine a residual amount of effluent left within the patient after a drain.

17. An automated peritoneal dialysis system comprising:
at least one dialysis fluid pump configured to pump a dialysis fluid to and from a patient over a treatment, the treatment including a plurality of patient fills, dwells and drains;

at least one conduit positioned and arranged to allow effluent fluid to be removed from the patient during at least one of the patient drains;
at least one processor; and
at least one memory device storing a plurality of instructions executed by the at least one processor to: (i) control the dialysis fluid pumped by the at least one dialysis fluid pump to and from a patient over the treatment, (ii) access a trend of ultrafiltration data points for the patient, and (iii) use one of the UF data points in a tidal treatment having a reduced drain volume to predict a residual volume of effluent fluid left in the patient's peritoneum after at least one of the plurality of patient drains.

18. The dialysis system of claim 17, the at least one processor/memory device configured to add a measured fill amount to the UF data point to determine an intra-peritoneal volume ("IPV") for the patient and then subtract a measured drain amount to determine the residual volume.

* * * * *